US008715645B2

(12) United States Patent
Bellgrau et al.

(10) Patent No.: US 8,715,645 B2
(45) Date of Patent: May 6, 2014

(54) VIRAL VECTORS ENCODING APOPTOSIS-INDUCING PROTEINS AND METHODS FOR MAKING AND USING THE SAME

(75) Inventors: Donald Bellgrau, Denver, CO (US); Richard C. Duke, Denver, CO (US); Jerome B. Schaack, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 722 days.

(21) Appl. No.: 10/825,282

(22) Filed: Apr. 14, 2004

(65) Prior Publication Data

US 2004/0224389 A1 Nov. 11, 2004

Related U.S. Application Data

(63) Continuation of application No. 09/456,357, filed on Dec. 8, 1999, now abandoned.

(60) Provisional application No. 60/134,416, filed on May 17, 1999.

(51) Int. Cl.
*A01N 63/00* (2006.01)

(52) U.S. Cl.
USPC ........................................................ 424/93.6

(58) Field of Classification Search
None
See application file for complete search history.

(56) References Cited

U.S. PATENT DOCUMENTS

| | | | | |
|---|---|---|---|---|
| 5,109,850 | A | 5/1992 | Blanco et al. | |
| 5,183,058 | A | 2/1993 | Janese | |
| 5,219,740 | A | 6/1993 | Miller et al. | 435/49.6 |
| 5,283,058 | A | 2/1994 | Faustman | 435/49.6 |
| 5,563,039 | A | 10/1996 | Goeddel et al. | 435/7.1 |
| 5,712,115 | A | 1/1998 | Hawkins et al. | 435/69.1 |
| 5,747,245 | A | 5/1998 | Reed et al. | 435/6 |
| 5,747,645 | A | 5/1998 | Sprecher | 530/350 |
| 5,750,653 | A | 5/1998 | Chu et al. | 530/350 |
| 5,756,086 | A | 5/1998 | McClelland et al. | 424/93.2 |
| 5,756,466 | A | 5/1998 | Bemis et al. | 514/18 |
| 5,759,536 | A | 6/1998 | Bellgrau et al. | |
| 5,760,180 | A | 6/1998 | Nicholson et al. | 530/350 |
| 5,763,223 | A | 6/1998 | Wiley et al. | 435/69.5 |
| 5,770,690 | A | 6/1998 | Bitler et al. | 530/324 |
| 5,786,173 | A | 7/1998 | Alnemri et al. | 435/69.1 |
| 5,869,315 | A | 2/1999 | Talanian et al. | 435/226 |
| 5,897,992 | A | 4/1999 | Fearnhead et al. | 435/29 |
| 6,325,999 | B1 | 12/2001 | Bellgrau et al. | |
| 6,391,612 | B1 | 5/2002 | Bruder et al. | |
| 2002/0155602 | A1 | 10/2002 | Bruder et al. | |

FOREIGN PATENT DOCUMENTS

| | | |
|---|---|---|
| EP | 675 200 A1 | 10/1995 |
| WO | WO 95/13293 | 5/1995 |
| WO | WO 95/18819 | 7/1995 |
| WO | WO-95/32627 A1 | 12/1995 |
| WO | WO 96/25501 | 8/1996 |
| WO | WO 99/13073 | 3/1999 |

OTHER PUBLICATIONS

Goncalves, Bioessays. 27(5):506-517, 2005.*
Juengst, BMJ, 326:1410-11, 2003.*
Rosenberg et al, Science 287:1751, 2000.*
Touchette, Nat. Med. 2(1) 7-8, 1996.*
Couzin et al, Science 307:1028, 2005.*
Check Nature 422:7, 2003.*
Greenman et al, Nature 446:153-158, 2007.*
Arai et al PNAS 94(25):13862-13867, 1997.*
Metastatic Cancer Fact Sheet by National Cancer Institute May 23, 2011.*
Salup et al, J Urol. 134(6):1236-41, 1985.*
Aslakson, C. et al., "Selective events in the metastatic process defined by analysis of the sequential dissemination of the subpopulationof a mouse mammary tumor", 1992, Cancer Res. vol. 42:pp. 1399-1405.*
Schmidt, M. et al., "Suppression of metastasis formation by a recombinant single chain antibody-toxin targetted to full-length and oncogenic variant EGF receptors", 1998, Oncogene, vol. 18; pp. 1711-1721.*
Xie, K. et al., "Abrogation of tumorigenicity and metastasis of murine and human tumor cells by transfection with the murine IFN-beta Gene: possible role of NO", 1997, CLin. Cancer Res., vol. 3; pp. 2283-2294.*
Abbas, 1996, *Cell*, 84:655-657.
Allison et al., 1997, *PNAS*, 94:3943-3947.
Arai et al., 1997, *Proc. Natl. Acad. Sci. USA*, 94:13862-13867.
Bellgrau and Selawry, 1990, *Transplantation*, 50:654-657.
Bellgrau et al., 1995, *Nature*, 377:630-632.
Byrne et al., 1997, *Transplantation*, 63:149-155 (abstract).
Chervonsky et al., 1997, *Cell*, 89:17-24.
Dorling et al., 1994, *Current Opin. Immunol.*, 6:765-769.
Fabre J.W., 1995, *Nat. Med.*, 1:403-404.
Hammer et al., 1986, *J. Animal Sci.*, 63:269-278 (abstract).
Hedlund et al., 1999, *Cell Death Differentiation*, 6:175-182.
Houdebine, 1994, *J. Biotechnol.*, 34:269-287 (abstract).
Iannaccone et al., 1994, *Dev. Biol.*, 163:288-292 (abstract).
Itoh et al., 1993, *J. Immunol.*, 151:621-627.
Jaenisch, 1988, *Science*, 240:1463-1474.
Johnstone & Thorpe, 1987, "Immunochemistry in Practice," by Blackwell Scientific Publications, Oxford, pp. 30-47.
Larregina et al., 1998, *Gene Therapy*, 5:563-568.
Lau et al., 1996, *Science*, 273:109-112.
Leff, 1995, *BioWorld Today*, 6(201):1-2.
Lee et al., 1994, *FASEB J.*, 8(5):A770.
Lo et al., 1991, *Eur. J. Immunol.*, 21:1001-1006 (abstract).
London et al., 1990, *Transplantation*, 49:1109-1113.
Lynch et al., 1994, *Immunity*, 1:131-136.

(Continued)

*Primary Examiner* — Michael Burkhart
(74) *Attorney, Agent, or Firm* — Morrison & Foerster LLP

(57) ABSTRACT

This invention discloses a novel method for propagation of viral vectors encoding proteins that induce apoptosis. The invention also discloses viral vectors produced by such methods and cells transfected with such vectors. Also disclosed are methods for suppressing T-lymphocyte-mediated graft rejection, for suppressing T-lymphocyte-mediated disease and for inducing apoptosis in cancer cells.

3 Claims, 5 Drawing Sheets

(56) References Cited

OTHER PUBLICATIONS

Mariani et al., 1995, *J. Immunol. Meth.*, 193:63-70.
Muruve et al., 1997, *Human Gene Therapy*, 8:955-963.
Nagata, 1996, *Nature Medicine*, 2:1306-1307.
Nagata et al., 1995, *Science*, 267:1449-1456.
Naji et al., 1976, *J. Surg. Res.*, 20:161-267.
Naji et al., 1981, *Science*, 213:1390-1392.
Ogasawara et al., 1993, *Nature*, 364:806-809.
Owen-Schaub et al., 1992, *Cellular Immunology*, 140:197-205.
Petrovsky et al., 2002, *Ann. NY. Acad. Sci.*, 958:204-208.
Selawry et al., 1985, *Diabetes*, 34:1019-1024.
Selawry et al., 1987, *Diabetes*, 36:1067.
Selawry et al., 1991, *Transplantation*, 52:846-850.
Selawry et al., 1993, *Cell Transplantation*, 2:123-129.
Shinoura et al., 1998, *Human Gene Ther.*, 9:2683-2689.
Suda et al., 1993, *Cell*, 75:1169-1178.
Suda et al., 1994, *J. Exp. Med.*, 179:873-879.
Takahashi et al., 1994, *Cell*, 76:969-976.
Takahashi et al., 1994, *International Immunology*, 6(10):1567-1574.
Tanaka et al., 1997, *J. Immunol.*, 158:2303-2309.
Vaux, 1995, *Nature*, 377:576-577.
Walker et al., 1983, *Nature*, 306:557-561.
Watson et al., 1987, *Molecular Biology of the Gene*, p. 313.
Wickelgren, 1996, *Science*, 273, col. 1, 3d paragraph.
Zhang et al., 1997, *J. Clin Invest.* 100:1951-1957.
Zhang et al., 1998, *J. Virol.*, 72(3):2483-2490.
U.S. Appl. No. 08/250,478, filed May 27, 1994, Bellgrau et al.
U.S. Appl. No. 09/456,357, filed Dec. 8, 1999, Bellgrau et al.
Anderson, W. French , Human Gene Therapy, Nature vol. 392, Supp, Apr. 30, 1998.
Friedmann, Theodore , Principles for Human Gene Therapy Studies, vol. 287, Mar. 2000.
Johnstone & Thorpe, "Immunochemistry in Practice", by Blackwell Scientific Publications, Oxford, (1987) pp. 30-47.
Lynch, et al., "Fas and FasL in the homeostatic regulation of immune responses,"Immunology Today, vol. 16, No. 12, Dec. 1995, pp. 569-574.
Mountz, "Autoimmune disease," Arthritis & Rheumatism, vol. 37, No. 10, Oct. 1994, pp. 1415-1420.
Nagata et al. "The Fas Death Factor," (1995) Science 267:1449-1456.
Nagata, "Fas and Fas Ligand: A Death factor and its receptor," Adv. Immunol. vol. 57, 1994, pp. 129-144.
Nagata, Shigekazu et al, The Fas Death Factor, Science, vol. 267, Mar. 10, 1995, pp. 1449-1456.
Smith et al., "The TNF Receptor Superfamily of Cellular and Viral Proteins: Activation, Costimulation, and Death," Cell, vol. 76, 959-962, Mar. 25, 1994.
Suda & Nagata, "Purification and Characterization of the Fas-ligand that induces Apoptosis," J. Exp. Med. vol. 179, Mar. 1994, pp. 873-879.
Varmus, Harold , Gene therapy: Not ready for prime time, Nature Medicine, vol. 2, Jan. 1, 1996.
Verma, Inder M. et al, Gene therapy promises, problems and prospects, Nature vol. 389, Sep. 18, 1997.
Verma, Inder M. , "Gene Therapy: beyond 2000," Molecular Therapy vol. 1, No. 6, Jun. 2000.
Notice of Reasons for Rejections for Japanese Application No. 08-501092, dated Nov. 25, 2005.
Notice of Reasons for Rejections for Japanese Application No. 08-501092, dated Sep. 26, 2006.
Decision to Grant a Patent for Japanese Patent Application No. Hei 8-501092, dated Mar. 23, 2007.
Official Action for European Application No. 95921459.4, dated Jun. 5, 2003.
Official Action for European Application No. 95921459.4, dated Feb. 17, 2004.
Official Action for European Application No. 95921459.4, dated Feb. 10, 2006.
Official Action for Canadian Patent Application No. 2,189,778, dated Sep. 25, 2009.
Official Action for Canadian Patent Application No. 2,189,778, dated Jan. 3, 2008.
Official Action for Australian Patent Application No. 26535/95, dated Jan. 2, 1998.
Official Action for Australian Patent Application No. 26535/95, dated May 27, 1999.
Notice of Acceptance for Australian Patent Application No. 26535/95, dated Nov. 24, 1999.
Supplementary European Search Report for European Application No. 95921459.4, dated Apr. 3, 1998.
Supplementary European Search Report for European Application No. 95921459.4, dated Apr. 22, 1999.
International Preliminary Examination Report for International (PCT) Application No. PCT/US95/06742, mailed Sep. 3, 1996.
International Search Report for International (PCT) Application No. PCT/US95/06742, mailed Aug. 5, 1995.
Written Opinion for International (PCT) Application No. PCT/US95/06742, mailed Aug. 5, 1995.
Kang et al., "Fas ligand expression in islets of Langerhans does not confer immune privilege and instead targets them for rapid destruction," 1997, Nature Med. 3:738-743.

* cited by examiner

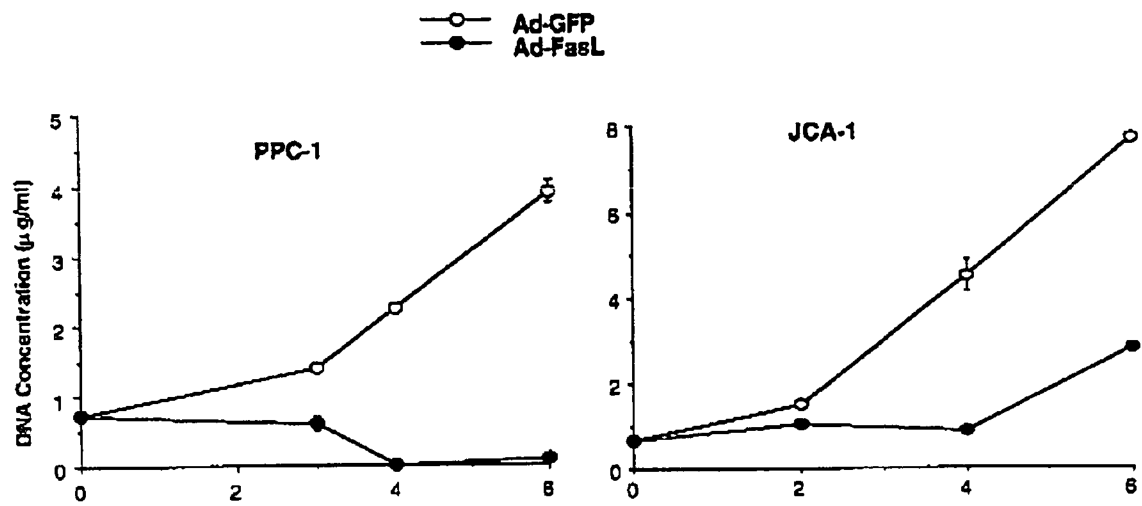
FIG. 4A
FIG. 4B
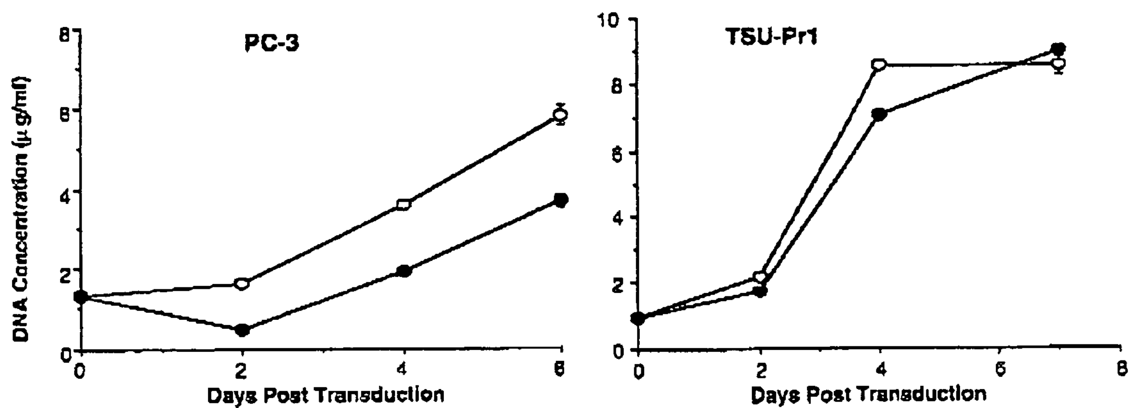
FIG. 4C
FIG. 4D

VIRAL VECTORS ENCODING APOPTOSIS-INDUCING PROTEINS AND METHODS FOR MAKING AND USING THE SAME

CROSS-REFERENCE TO RELATED APPLICATIONS

This application is a continuation of U.S. patent application Ser. No. 09/456,357, filed Dec. 8, 1999, which claims priority under 35 U.S.C. §119(e) from U.S. Provisional Application Ser. No. 60/134,416, filed May 17, 1999, entitled "Product for Production of Apoptosis-Inducing Proteins and Uses Therefor".

FIELD OF THE INVENTION

The present invention generally relates to a method for propagating viral vectors encoding proteins that induce apoptosis, and to products and methods related to the used of such viral vectors. In particular, the present invention relates to methods of using viral vectors of the present invention in methods for suppressing T-lymphocyte-mediated graft rejection and T-lymphocyte-mediated disease and for inducing apoptosis in cancer cells.

BACKGROUND OF THE INVENTION

Apoptosis is a regulated form of cell death that is necessary for normal cell function and development. The regulation of apoptosis in a cell is mediated by diverse signals and complex interactions of many different cellular gene products. Dysregulation of apoptosis can cause or contribute to a variety of diseases and conditions. However, having the ability to induce apoptosis in target cells in certain disease states would be extremely advantageous. Over the past several years, numerous gene products which modulate the apoptotic process have been identified. The discovery of such gene products presents opportunities to intervene in normal and abnormal cellular processes and regulate cell death for therapeutic purposes.

Fas is one such gene product. Fas (CD95/APO-1) is a transmembrane glycoprotein that is related to the receptors for tumor necrosis factor and nerve growth factor (Itoh et al., 1991, *Cell* 66:23-243; Oehm et al., 1992, *J. Biol. Chem.* 267:10709-10715). Upon being cross-linked with agonistic anti-Fas antibodies or Fas ligand (FasL), Fas initiates a complex signal transduction pathway that, in sensitive cell types, ultimately ends in apoptotic cell death. The Fas/FasL pathway is probably best recognized for its role in the downregulation of expanded clonal T lymphocyte populations. In this system, Fas is upregulated within a few hours of T cell activation (Miyawaki et al., 1992, *J. Immunol.* 149:3753-3758). Several days later, Fas becomes functional and if the cells continue to be stimulated through the antigen receptor, FasL is also upregulated (Owen-Schaub et al., 1992, *Cell. Immunol.* 140: 197-205; Suda et al., 1993, *Cell* 75:1169-1178), and the majority of activated cells undergo apoptosis, allowing the immune system to return to its normal resting size and repertoire.

In related U.S. Pat. No. 5,759,536, the present inventors disclosed that a factor released by testicular Sertoli cells, which is responsible for the protection of the intratesticular islet allografts and xenografts against rejection, is the Fas ligand. U.S. Pat. No. 5,759,536 disclosed the use of Fas ligand to suppress graft rejection, to suppress T lymphocyte-mediated disease, and to suppress T lymphocyte-mediated disease recurrence. Fas ligand mediates its effect by interacting with Fas. As discussed in detail in U.S. Pat. No. 5,759,536, a major problem associated with transplantation of any tissue is immune-mediated graft rejection in which the recipient's T-lymphocytes recognize donor histocompatibility antigens as foreign. Current regimes for transplanting many tissues and organs require lifelong administration of immunosuppressive drugs. These drugs have serious side-effects and can cause increased susceptibility to infection, renal failure, hypertension, and tumor development. Fas ligand/Fas-mediated apoptosis provided a novel solution to these problems.

In addition to regulating immune responses, Fas and its ligand are likely to play a role in other systems as well. For example, the testes and placenta, both of which are known to be immune-privileged tissues, express FasL (Xerri et al., 1997, *Mol. Pathol.* 50:87-91). Additionally, Fas and FasL have been found to be coexpressed in a few epithelial tissues that are marked by apoptotic cell turnover, such as the uterus and prostate (Leithauser et al., 1993, *Lab. Invest.* 69:415-429; French et al., 1996, *J Cell. Biol.* 133:335-343; and Xerri et al., 1997, supra). Both of these tissues are steroid-dependent and undergo apoptosis within 24-48 h after hormone depletion (Issacs et al., 1992, *J. Androl.* 19:457-464; Rotello et al., 1992, *Am. J. Pathol.* 140:449-456). Interestingly, the apoptosis that occurs in response to steroid depletion has recently been shown to require sufficient Fas expression (Suzuki et al., 1996, *EMBO. J.* 15:211-215; Suzuki et al., 1996, *Oncogene* 13:31-37). These data support a role for the Fas signaling pathway in the normal renewal of the uterine and prostatic epithelium.

In addition to the in vivo data above, several laboratories have recently demonstrated a potential role for Fas-dependent apoptosis in human prostate cancer (PC) cell lines (Rokhlin et al., 1997, *Cancer Res.* 57:1756-1758; Uslu et al., 1997, *Clin. Cancer Res.* 3:963-972; Hedlund et al., 1998, *Prostate* 36:92-101). Although Fas expression has proved to be a common feature of the cell lines studied, contradictory results were reported with regard to their apoptotic potentials. This may be due to the use of different agonistic anti-Fas antibodies among laboratories, or to the different experimental conditions that were employed. Taken as a whole, these studies indicated that the apoptotic potential of cells expressing Fas may not be sufficient to enable the widespread use of Fas ligand as a therapeutic agent.

In addition, the ability to produce Fas ligand in a form and quantity which is readily useable for both in vitro and in vivo scientific and clinical protocols has been a problem experienced by several researchers. In particular, production of viral vectors encoding apoptosis-inducing proteins such as Fas ligand has met with limited success, due to massive death of the cells used to package and/or deliver such vector and/or unsuitably low viral production (Larregina et al., 1998, *Gene Therapy* 5:563-568; Muruve et al., 1997, *Hum. Gene. Ther.* 8:955-963; Arai et al., 1997, *PNAS USA* 94:13862-13867; Kang et al., 1997, *Nature Med.* 3:738-743). Such problems are particularly apparent when efforts have been made to scale up production of the vector. This problem of autocrine regulation can be generally extended to other apoptosis-inducing proteins. Therefore, although Fas ligand and/or other apoptosis-inducing proteins appear to be ideal candidates for various therapeutic protocols, including suppression of graft rejection, suppression of T-lymphocyte-mediated disease, and treatment of cancers, unexpected problems with the production and use of such proteins have hindered efforts to design useful therapeutic strategies using such agents.

Therefore, there is a need in the art for a safe and effective agent, such as a construct encoding Fas ligand and/or other apoptosis-inducing proteins, which is capable of inducing apoptosis in a desired target cell.

SUMMARY OF THE INVENTION

One embodiment of the present invention relates to a method to propagate a recombinant viral vector comprising a nucleic acid sequence encoding an apoptosis-inducing protein. The method includes the step of culturing an isolated cell transfected with: (a) a recombinant nucleic acid molecule comprising a nucleic acid sequence encoding a protein that inhibits apoptosis operatively linked to a transcription control sequence; and, (b) a recombinant viral vector comprising a nucleic acid sequence encoding a protein that induces apoptosis operatively linked to a transcription control sequence. The isolated cell is cultured under conditions effective to propagate the recombinant viral vector. In one embodiment, the method additionally includes the step of recovering the recombinant viral vector from the isolated cell. Preferably, the isolated cell is a mammalian cell.

In one embodiment, the recombinant nucleic acid molecule of (a) is contained within the recombinant viral vector of (b). In this aspect, the nucleic acid sequence of (a) and the nucleic acid sequence of (b) can be operatively linked to different transcription control sequences or to the same transcription control sequences. In one aspect, the nucleic acid sequence of (a) and the nucleic acid sequence of (b) are separated by an internal ribosome entry site (IRES).

The protein that inhibits apoptosis can include inhibitors of caspase-8 family activation and inhibitors of caspase-9 family activation. In one embodiment, the protein that inhibits apoptosis is a protein having biological activity of a protein which includes, but is not limited to, cowpox virus caspase inhibitor (CrmA), baculovirus p35, inhibitor of apoptosis protein (IAP), dominant negative Fas-associating death domain-containing protein (dominant negative FADD), dominant negative Fas, FADD-like ICE inhibitory protein (FLIP), Bcl-2, Bcl-$X_L$, and adenovirus E1B-19K protein. Preferred nucleic acid sequences encoding a protein that inhibits apoptosis encode a protein comprising an amino acid sequence selected from the group of SEQ ID NO:38, SEQ ID NO:40, SEQ ID NO:42, SEQ ID NO:44, SEQ ID NO:46, SEQ ID NO:48, SEQ ID NO:50, and positions 80-208 of SEQ ID NO:14. Preferred nucleic acid sequences encoding a protein that inhibits apoptosis include SEQ ID NO:37, SEQ ID NO:39, SEQ ID NO:41, SEQ ID NO:43, SEQ ID NO:45, SEQ ID NO:47, SEQ ID NO:49, and positions 367-753 of SEQ ID NO:13. In a preferred embodiment, the protein that inhibits apoptosis is a protein having CrmA biological activity.

The protein that induces apoptosis can include, but is not limited to a protein that has biological activity of a protein selected from the group consisting of Fas ligand, Fas, Fas-associating death domain-containing protein (FADD), Fas-associated death domain-like IL-1β converting enzyme (FLICE), tumor necrosis factor (TNF), TWEAK/Apo3L, TRAIL/Apo2L, Bax, Bid, Bik, Bad, Bak, and RICK. Preferred proteins that induces apoptosis comprise an amino acid sequence selected from the group of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34 and SEQ ID NO:36. Preferred nucleic acid sequences encoding a protein that induces apoptosis is selected from the group consisting of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33 and SEQ ID NO:35.

In one embodiment, the recombinant viral vector is packaging deficient. In another embodiment, the recombinant viral vector is replication deficient. The recombinant viral vector is preferably from a virus including, but not limited to, alphaviruses, poxviruses, adenoviruses, herpesviruses, lentiviruses, adeno-associated viruses, vaccinia viruses, baculoviruses, parvoviruses and retroviruses. In a preferred embodiment, the recombinant viral vector is from an adenovirus. In one aspect, the recombinant viral vector comprises a human adenovirus 5 construct under the control of a CMV immediate early promoter. Such a human adenovirus 5 construct can be replication deficient. In another embodiment, the recombinant viral vector comprises a nucleic acid sequence represented by at least a portion of SEQ ID NO:4.

Preferably, the present method results in the isolated cell producing at least about $1\times10^8$ plaque forming units (pfu) of the recombinant viral vector per ml of supernatant isolated from the cell, and more preferably, at least about $5\times10^8$ pfu, and more preferably, at least about $1\times10^9$ pfu of the recombinant viral vector per ml of supernatant isolated from the cell.

Another embodiment of the present invention relates to an isolated cell, wherein the cell is transfected with: (a) a recombinant nucleic acid molecule comprising a nucleic acid sequence encoding a protein that inhibits apoptosis operatively linked to a transcription control sequence; and, (b) a recombinant viral vector comprising a nucleic acid sequence encoding a protein that induces apoptosis operatively linked to a transcription control sequence. In one embodiment, the recombinant nucleic acid molecule of (a) is contained within the recombinant viral vector of (b). In this aspect, the nucleic acid sequence of (a) and the nucleic acid sequence of (b) can be operatively linked to different transcription control sequences. Alternatively, the nucleic acid sequence of (a) and the nucleic acid sequence of (b) can be separated by an internal ribosome entry site (IRES). Other preferred embodiments of such a recombinant viral vector and recombinant molecule are as disclosed above.

Another embodiment of the present invention relates to a recombinant viral vector for inducing apoptosis in cells transfected with the vector. The viral vector comprises a recombinant virus comprising: (a) an isolated nucleic acid sequence encoding a protein that inhibits apoptosis operatively linked to a transcription control sequence; and, (b) an isolated nucleic acid sequence encoding a protein that induces apoptosis operatively linked to a transcription control sequence. In one embodiment, the nucleic acid sequence of (a) and the nucleic acid sequence of (b) are operatively linked to different transcription control sequences. In another embodiment, the nucleic acid sequence of (a) and the nucleic acid sequence of (b) are separated by an internal ribosome entry site (IRES). Other preferred embodiments of such a recombinant viral vector and recombinant molecule are as disclosed above. In one embodiment, the recombinant viral vector comprises a nucleic acid sequence represented by at least a portion of SEQ ID NO:4.

Another aspect of the present invention relates to a recombinant viral vector comprising: (a) an isolated human adenovirus 5 construct encoded by a nucleic acid sequence comprising at least a portion of SEQ ID NO:4; and, (b) a recombinant nucleic acid molecule comprising a nucleic acid sequence encoding Fas ligand or a biologically active fragment thereof, operatively linked to a transcription control sequence. More particular aspects of the viral vector and recombinant nucleic acid molecule have been disclosed above.

Yet another embodiment of the present invention relates to a method of suppressing T-lymphocyte-mediated graft rejection in a recipient mammal, the method comprising introducing into the mammal a pharmaceutically acceptable carrier comprising a recombinant viral vector comprising a nucleic acid sequence encoding a protein that induces apoptosis operatively linked to a transcription control sequence, wherein the recombinant viral vector expresses the protein that induces apoptosis. The pharmaceutically acceptable carrier can further comprise a recombinant nucleic acid molecule comprising a nucleic acid sequence encoding a protein that inhibits apoptosis operatively linked to a transcription control sequence. In this aspect, the recombinant nucleic acid molecule comprising a nucleic acid sequence encoding a protein that inhibits apoptosis can be contained within the recombinant viral vector. In this aspect, the nucleic acid sequence encoding a protein that inhibits apoptosis and the nucleic acid sequence encoding a protein that induces apoptosis can be operatively linked to different transcription control sequences or alternatively, the nucleic acid sequence encoding a protein that inhibits apoptosis and the nucleic acid sequence encoding a protein that induces apoptosis can be separated by an internal ribosome entry site (IRES).

In one embodiment, the pharmaceutically acceptable carrier is an isolated cell that is transfected with the recombinant nucleic acid molecule and the recombinant viral vector and/or a pharmaceutically acceptable excipient. In one aspect, the isolated cell is a cell of the graft. In another embodiment, the cell is not part of the graft. In another embodiment, the cell is an islet cell.

Another embodiment of the present invention relates to a method of inducing apoptosis in cancer cells of a recipient mammal, comprising introducing into the mammal a recombinant viral vector comprising: (a) a recombinant nucleic acid molecule comprising a nucleic acid sequence encoding a protein that inhibits apoptosis operatively linked to a transcription control sequence; and, (b) a recombinant viral vector comprising a nucleic acid sequence encoding a protein that induces apoptosis operatively linked to a transcription is control sequence. The protein that induces apoptosis is expressed by a cell at or adjacent to a site of the cancer, and the expression of the protein at the site of the cancer is sufficient to produce a result selected from the group of: reduction of tumor size, elimination of tumor cells at the site; prevention of tumor growth at the site and prevention of metastases from the tumor cells. The cancer can include, but is not limited to, lung cancer, brain cancer, prostate cancer, lymphoma and leukemia.

Yet another embodiment of the present invention relates to a method of suppressing a T-lymphocyte-mediated disease in a recipient mammal, the method comprising introducing into the mammal a pharmaceutically acceptable carrier comprising a recombinant viral vector comprising a nucleic acid sequence encoding a protein that induces apoptosis operatively linked to a transcription control sequence, wherein the recombinant viral vector expresses the protein that induces apoptosis. In this embodiment, the pharmaceutically acceptable carrier can further comprise a recombinant nucleic acid molecule comprising a nucleic acid sequence encoding a protein that inhibits apoptosis operatively linked to a transcription control sequence. In this aspect, the recombinant nucleic acid molecule comprising a nucleic acid sequence encoding a protein that inhibits apoptosis can be contained within the recombinant viral vector. The nucleic acid sequence encoding a protein that inhibits apoptosis and the nucleic acid sequence encoding a protein that induces apoptosis can be operatively linked to different transcription control sequences or alternatively, the nucleic acid sequence encoding a protein that inhibits apoptosis and the nucleic acid sequence encoding a protein that induces apoptosis can be separated by an internal ribosome entry site (IRES). The pharmaceutically acceptable carrier can be an isolated cell that is transfected with the recombinant nucleic acid molecule and the recombinant viral vector and/or a pharmaceutically acceptable excipient. In this embodiment of the invention, the T lymphocyte-mediated disease can include, but is not limited to, rheumatoid arthritis, insulin-dependent diabetes mellitus, multiple sclerosis, lupus erythematosus, myasthenia gravis, and graft versus host reactions.

BRIEF DESCRIPTION OF THE DRAWINGS OF THE INVENTION

FIG. 4A is a line graph showing the effect of Ad-FasL transduction on short-term growth curves of prostate cancer cell line PPC-1.

FIG. 4B is a line graph showing the effect of Ad-FasL transduction on short-term growth curves of prostate cancer cell line JCA-1.

FIG. 4C is a line graph showing the effect of Ad-FasL transduction on short-term growth curves of prostate cancer cell line PC-3.

FIG. 4D is a line graph showing the effect of Ad-FasL transduction on short-term growth curves of prostate cancer cell line TSU-Pr1.

DETAILED DESCRIPTION OF THE INVENTION

Figure 1A:
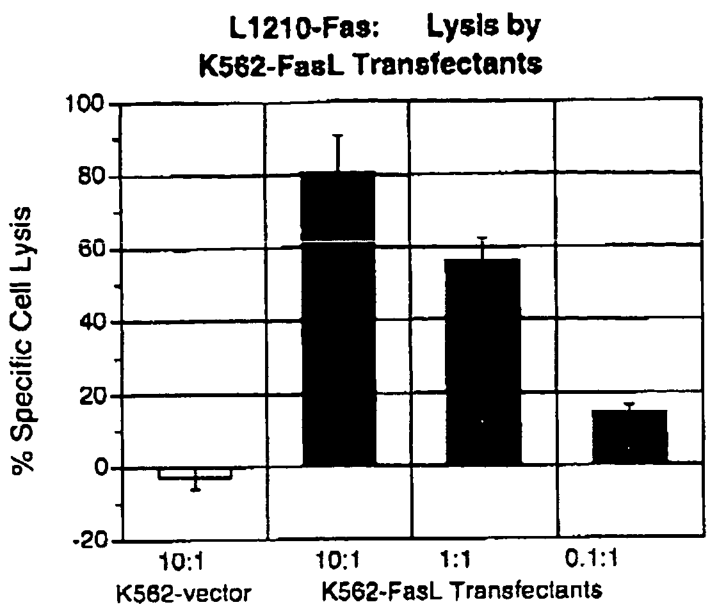
FIG. 1A is a bar graph illustrating that K562-hFasL induces lysis of L1210-Fas in a dose-dependent fashion.

The present invention is generally related to the present inventors' discovery of a novel system for the propagation of viral vectors wherein autocrine regulation by production of the protein is problematic. Specifically, the present invention is related to the discovery that it is possible to successfully produce and propagate viral vectors encoding apoptosis-inducing proteins in significant quantities without destroying the production cell line or experiencing problems with production levels that have been observed prior to the present invention. The present invention relates to the use of a combination of a novel viral delivery vector encoding an apoptosis-inducing protein and an isolated nucleic acid molecule encoding an apoptosis-inhibiting protein to propagate the viral vector encoding the apoptosis-inducing protein. In addition, the present invention relates to the use of the viral vector encoding an apoptosis-inducing protein, alone or combined with an isolated nucleic acid molecule encoding an apoptosis-inhibiting protein, in a product and method to suppress graft rejection, to suppress T-lymphocyte mediated diseases, and to treat cancers.

Several laboratories have reported on the apoptotic potentials of human prostate cancer (PC) cell lines in response to crosslinking of Fas (CD95/APO-1) with agonistic anti-Fas antibodies. As discussed above, however, contradictory results have been reported with regard to their apoptotic potentials. Moreover, soluble FasL, while once appearing to be a desirable means of using Fas ligand as a therapeutic tool, is now known to sometimes be ineffective for the induction of apoptosis in a Fas-bearing cell in at least some scenarios (Tanaka et al., 1998*, J Exp. Med.* 187:1205-1213). In addition, while researchers have focused considerable effort on the production of viral vectors encoding Fas ligand and other apoptosis-inducing proteins for use in suppression of graft rejection, tumor reduction, or suppression of T-lymphocyte-mediated disease, problems with massive cell death of the packaging or delivery cell lines and/or inadequate viral titers have shed doubt on the ability of such vectors to realistically be used in therapeutic methods. Some researchers have proposed potential solutions to the problem of producing viral vectors expressing Fas ligand. For example, Arai et al., 1997, supra describe the use of soluble caspase inhibitor, N-benzyloxycarbonyl-Val-Ala-Asp-fluoromethyketone, in the cell culture medium, and/or use of a Fas-ligand resistant clone of 293 cells to produce Fas ligand-viral vectors. Kanagae et al. suggest cotransfecting production cell lines with a second vector which regulates the expression of the gene of interest by inducing or inhibiting expression on demand (Kanagae et al, 1995*, Nuc. Acids Res.* 23:3816-3821). Yoshida et al. have suggested the use of an inducible promoter to produce other problematic cytotoxic products (VSVG protein) by a viral vector (Yoshida et al., 1995*, Biochem. Biophys. Res. Commun.* 232:379-382). These methods, however, are either inadequate, more time consuming and difficult, or are less effective than the method discovered by the present inventors and described herein. Moreover, the method and constructs of the present invention result in the production of a vector which can be used in vivo without additional manipulations of the subject which would be required by the other methods.

The present inventors have developed a viral vector system which employs cells transfected with both a viral vector encoding an apoptosis-inducing protein and an isolated nucleic acid molecule encoding an apoptosis-inhibiting protein, to enable the propagation of viral vectors encoding such apoptosis-inducing proteins, as well as the subsequent use of the vectors to express the proteins wherein such propagation and production is typically problematic. By way of example, the present inventors have developed a novel adenoviral expression system for FasL by a viral construct and have employed 293 cells that stably express CrmA, a Cowpox virus inhibitor of apoptosis, to propagate the viral construct. The present inventors have further determined the effects of FasL when expressed internally by cell lines. The vectors described herein can be used in a variety of methods as described generally for the apoptosis-inducing protein, Fas ligand, in U.S. Pat. No. 5,759,536, which is incorporated herein by reference in its entirety.

The present inventors have also re-evaluated the apoptotic potentials of seven human prostate cancer (PC) cell lines using the natural Fas ligand (FasL) in place of agonistic antibody. First, PC cell lines were tested in a standard cytotoxicity assay with a transfected cell line that stably expresses human FasL. The present inventors' data demonstrate that viral vectors encoding Fas ligand can be efficiently and effectively produced in significantly high titers in multiple cell types without destroying the producing cell line. In addition, the present inventors have discovered that the apoptotic potentials of PC cell lines have been greatly underestimated in previous studies utilizing agonistic anti-Fas antibodies. The present inventors' data further demonstrate that internally expressed Fas ligand is more effective than exposure of cellular Fas to an external source of Fas ligand. Lastly, adenoviral-mediated expression of FasL prevented growth and induced regression of two human PC cell lines in immunodeficient mice. These in vivo results illustrate a use for adenovirus encoding apoptosis-inducing proteins such as FasL as a gene therapy for diseases such as PC, and illustrate another means of administering FasL to a patient to suppress graft rejection and/or T-lymphocyte mediated disease as disclosed in U.S. Pat. No. 5,759,536.

During the course of the present inventors' research, Arai and colleagues addressed similar questions regarding the effects of FasL expression on the growth of colon cancer cell lines in mice (Arai et al., 1997, ibid.). Overall, their findings strongly support the therapeutic potential of FasL transgene expression in causing the regression of tumors. Furthermore, their data suggest that this favorable response is not only observed in cell lines that undergo apoptosis in response to FasL expression in vitro. In fact, tumor regression also occurs in a Fas-negative (and FasL-insensitive) cell line, and regression is associated with a marked infiltration by neutrophils, many of which appear apoptotic. However, Arai and colleagues did not address the issue of how to produce a viral vector encoding Fas ligand in a manner that results in propagation of a vector in sufficient quantities and in a form that is readily administered to a patient for the treatment of cancer (e.g., in the absence of other manipulations of the patient and/or vector). Subsequent to the present invention, Shinoura and colleagues confirmed the present inventors' results for production of viral vector encoded Fas ligand and Fas by describing another adenoviral vector-Fas ligand construct and an adenoviral vector-Fas construct, both of which were successfully constitutively produced at high titers by using CrmA-transfected 293 cells (Shinoura et al., 1998*, Human Gene Therapy* 9:2683-2689). The results of Shinoura et al. confirm the present inventors' discovery that a biological system using CrmA-transfected cells is useful for producing viral vectors encoding apoptosis-inducing proteins.

The present inventors' discovery of the novel biological system for the propagation of viral vectors encoding apoptosis-inducing proteins is extremely valuable for its application to the suppression of graft rejection, the suppression of T-lymphocyte mediated diseases, and the treatment of cancers, since now the production of such viral vectors in high titers is possible.

Reference will now be made in detail to useful embodiments of the invention, which, together with the following examples and claims, serve to explain the principles of the invention. It is to be understood that this invention is not limited to the specific examples described, and as such may, of course, vary. it is also to be understood that the terminology used herein is with the purpose of describing particular embodiments only, and is not intended to limit the scope of the invention which will be limited only by the amended claims. In addition, discussion of various embodiments of the invention is made with particular reference to Fas ligand, although it is to be understood that Fas ligand serves as an exemplary apoptosis-inducing protein, and that other apoptosis-inducing proteins are encompassed by the present invention and the discussion relates also to such proteins.

Unless defined otherwise, all technical and scientific terms used herein have the same meaning as commonly understood by one of ordinary skill in the art. Although any methods and materials similar to or equivalent to those described herein can be used in the practice or testing of the invention, the preferred methods and materials are now described. All publications mentioned herein are incorporated herein by reference to describe and disclose specific information with which the reference was cited in connection.

One embodiment of the present invention relates to a method to propagate a recombinant viral vector comprising a nucleic acid sequence encoding an apoptosis-inducing protein, to the recombinant viral vectors produced by such a method and to isolated cells transfected with such recombinant viral vectors. Specifically, this method of the present invention includes the step of culturing an isolated cell (also referred to herein as a production cell line) that has been cotransfected with: (a) a recombinant nucleic acid molecule comprising a nucleic acid sequence encoding a protein that inhibits apoptosis operatively linked to a transcription control sequence; and, (b) a recombinant viral vector comprising a nucleic acid sequence encoding a protein that induces apoptosis operatively linked to a transcription control sequence. The step of culturing is performed under conditions that are effective to propagate the recombinant viral vector (discussed in detail below). The method can additionally include the step of recovering the recombinant viral vector from the isolated cell, although in certain aspects of the present invention, it is desirable to use the transfected isolated cell in a therapeutic composition or method, as discussed below. Cell lines and/or other pharmaceutically acceptable carriers which contain the recombinant viral vector comprising a nucleic acid sequence encoding an apoptosis-inducing protein, alone or in combination with a recombinant nucleic acid molecule comprising a nucleic acid sequence encoding an apoptosis-inhibiting protein, can be used in a therapeutic composition for suppressing T-lymphocyte-mediated graft rejection, for suppressing T-lymphocyte-mediated disease in a recipient mammal, and/or for inducing apoptosis in cells of a mammal, such as in cancer cells. These embodiments are discussed in detail below.

According to the present invention, the term "apoptosis" is defined as a regulated form of cell death that is necessary for normal cell function and development. As used herein, apoptosis refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing), typically, although not always, with engulfment of intact cell fragments ("apoptotic bodies") by phagocytic cells. Apoptosis differs from necrosis in which cells swell and eventually rupture. For a detailed background review of apoptosis and the cellular and biochemical events involved in the regulation of apoptosis, see, for example, Duke et al., 1996, *Sci. Am.* 275:80-87, which is incorporated herein by reference in its entirety.

Apoptosis can be determined by any suitable method, including by determining the extent of a morphological change in a cell. Such a morphological change can include, for example, progressive contraction of cell volume with the preservation of the integrity of cytoplasmic organelles and condensation of chromatin. Additionally, such a method can include determining the extent of DNA cleavage by gel electrophoresis, cell cycle analysis, or in situ tailing or nick translation. Additionally, such a method can include assessing membrane permeability by using dyes that bind RNA or DNA or Annexin V. Such assays for apoptosis are well known in the art; a few are described below.

For example, apoptosis of a cell can be assessed by using DNA binding dyes. These dyes are used to stain live cells for subsequent microscopic analysis or for subsequent flow cytometric analysis. When used for microscopic analysis of live cells, this technique assays nuclear morphology and membrane permeability. It provides one of the best ways of assessing apoptotic morphology in a quantitative manner and of discriminating live from dead cells and apoptotic from necrotic cells. When used for flow cytometric analysis, this technique assays membrane permeability. These dyes also bind DNA and are widely used to assay stages of the cell cycle by flow cytometry. Resting cells contain a 2N amount of DNA and form a "G1" peak, while cells in mitosis contain a 4N amount of DNA and form a 'G2' peak. DNA binding dyes have also been used at lower concentrations in fixed cells to identify an apoptotic sub-G1 peak below the resting G1 peak. This lower peak may be due to loss of DNA fragments with apoptosis or to altered conformation of apoptotic DNA. DNA laddering assays endonucleolytic cleavage of DNA into 200 base pair multimers. The scatter changes technique identifies apoptotic cells by their decreased forward scatter (due to cell shrinkage) and their increased side scatter (due to DNA condensation). This technique is easy; quantitative; can be done retrospectively on any cell sample that has been analyzed flow cytometrically, since all samples are routinely analyzed for forward and side scatter; can be done on fresh or fixed cells, and; can be done in conjunction with cell surface phenotyping or with immunofluorescent labeling of an intracellular marker. TUNEL or in situ nick translation takes advantage of the classic feature of apoptosis, DNA fragmentation. The enzyme terminal deoxynucleotidyl transferase (TdT) adds labeled nucleotides to the ends of nicked DNA. The label is then revealed in different ways depending on the application; a radioactive label allows development of grains over cells in fixed tissue, while a biotin-avidin conjugate allows immunohistochemical labeling of cells in tissue or flow cytometric analysis of cells in suspension. This technique is quantitative and allows for concurrent phenotyping of cells and for analysis of expressed RNAs by in situ hybridization.

According to the present invention, an "apoptosis-inducing protein" or "protein that induces apoptosis" is any protein which is directly associated with inducing (e.g., causing, upregulating, initiating, propagating, increasing, or enhancing) the biological process of apoptosis in a cell. As used herein and discussed in detail below, an apoptosis-inducing protein can include a biologically active homologue of a naturally occurring apoptosis-inducing protein. Apoptosis-inducing proteins can include cellular receptors and ligands which, through ligation of such proteins, initiate apoptosis by, for example, transduction of a signal into a cell which activates other proteins in the apoptotic signal transduction pathway of the cell; and intracellular mediators of apoptotic events in the cell (e.g., DNA cleavage, condensation of chromatin), including cytoplasmic mediators involved in the formation of "death inducing complexes", apoptosis-initiating members of the caspase family which are recruited and activated by the cytoplasmic mediators, and apoptosis-effector caspases, which are recruited and activated by the initiator caspases.

Many of these apoptosis-inducing proteins are known and described in detail in the art (See, for example, the review by Duke et al., 1996, supra). Studies with inhibitors, dominant negative mutants of apoptosis-inducing molecules, and the phenotypes of transgenic ablated mice with defects in apoptosis-inducing molecules have elucidated two distinct pathways of initiator caspase activation in apoptosis. One pathway involves apoptosis induced by the tumor necrosis factor receptor (TNFR) family of molecules whose cytoplasmic domains contain a "death domain" (DD). This family, which includes TNF-R1, Fas (CD95/Apo1), DR3 (Apo3), and DR4/DR5, all utilize caspase-8 as an initiator caspase. Upon crosslinking with their respective ligands (TNF, FasL, Apo3L/TWEAK and Apo2L/TRAIL), DD regions are brought into close proximity with one another initiating the formation of a "death-inducing complex" (DIC). The first molecule to bind to the clustered DD regions is a molecule called FADD (Fas-associated death domain; also called Mort-1). FADD contains a "death effector domain" (DED; also called a caspase recruitment domain or CARD) which recruits and binds the proform of caspase-8 (also called FLICE - Fas-like ICE). The pro-caspase-8 molecules recruited by the aggregated FADD molecules oligomerize and become activated through self-cleavage. Activated caspase-8 is then able to cleave the proform of the initiator caspase-9 leading to a cascade of cleavage and activation of downstream effector caspases.

The second pathway of initiator caspase activation also involves assembly of a death-inducing complex involving proteins with CARD domains. Activation of this pathway occurs through many signals including some of those that are described below. While the signals that appear to induce this pathway are quite diverse, including some that require de novo protein synthesis, mitochondria are the targets for each inducer. In brief, a very early event in this pathway involves changes in mitochondria which include release of cytochrome c, loss of mitochondrial transmembrane potential and altered redox potential. Of these, the role of cytochrome c in activation of caspases has received the greatest attention.

Cytochrome c that is released from mitochondria binds to Apaf-1, a CARD-containing, "apoptosis protease activating factor." Cytochrome c binding allows Apaf-1 molecules to self-associate and bind to the CARD domain of pro-caspase-9 forming what is called an "apoptosome". As with caspase-8 activation, activation of caspase-9 in the apoptosome is thought to occur due to aggregation of the zymogens. Pro-caspase-9 then autocleaves and initiates the downstream effector caspase activation cascade resulting in apoptosis.

According to the present invention, an "apoptosis-inhibiting protein" or "protein that inhibits apoptosis" is any protein which is directly associated with inhibiting (e.g., preventing, downregulating, halting, attenuating, or decreasing) the biological process of apoptosis in a cell. As used herein and discussed in detail below, an apoptosis-inhibiting protein can include a biologically active homologue of a naturally occurring apoptosis-inhibiting protein. Apoptosis-inhibiting protein include proteins that inhibit the signal transduction by apoptosis-inducing receptor/ligand interactions, proteins that inhibit the aggregation of death domains and recruitment of such proteins into death inducing complexes; proteins that inhibit the recruitment of initiator caspases, proteins that inhibit the activation of initiator caspases, and proteins that inhibit the recruitment and/or activation of effector caspases.

Many of these apoptosis-inhibiting proteins, and the mechanisms by which they act are known and described in detail in the art (See, for example, review by Duke, 1999, ibid.). For example, the TNFR family pathway does not require de novo protein synthesis in order to initiate apoptosis. In fact, protein synthesis inhibitors actually augment the response following receptor ligation. This appears to be due to loss of labile inhibitors. One group of such labile inhibitors are called FLIPs (FADD-like ICE inhibitory protein; also called CLARP, Casper, I-FLICE, FLAME-1, $CASH_L$ and MRIT). FLIPs have a DED/CARD domain but lack the catalytic domain of other caspases. Thus they act as decoys and either slow or block formation of the death-inducing complex. FLIPs are inactivated by a kinase called RICK (RIP-like interacting CLARP kinase) which interacts with FLIP via, not surprisingly, a DED/CARD domain.

Over-expression of members of the Bcl-2 family of proteins such as Bcl-2, $BCl-X_L$, and Mcl-1 abrogate cytochrome c release and inhibit apoptosis. Members of the Bcl-2 family are anchored in the outer mitochondrial membrane, as well as in the endoplasmic reticulum and nuclear envelope, and all can form both homodimers and heterodimers with some or all of the other members, as well as with many proteins in the apoptosis-inducing pathways. In general, heterodimerization of an apoptosis-inducing protein with an apoptosis-inhibiting protein appears to abrogate the function of both proteins. In contrast, a preponderance of homodimers will shift the cell either toward or away from undergoing apoptosis.

One way that this might work is suggested by recent results studying the role of the tumor suppressor gene product Akt-1 (also called protein kinase B). Many molecules including insulin-like growth factor-1 (IGF-1) and focal adhesion kinase (FAK, see below) positively regulate Akt-1. Akt-1 appears to inhibit apoptosis by two mechanisms. First, it upregulates $BCl-X_L$. Second it directly phosphorylates Bad. Phosphorylated Bad forms a complex with a molecule called 14-3-3 which prevents Bad from forming a heterodimer with either $Bcl-X_L$ or Bcl-2, thereby allowing these molecules to block apoptosis.

A general scheme is arising which suggests that the anti-apoptotic members prevent Apaf-1 from forming a complex with caspase-9, in effect by segregating Apaf-1 away. By forming heterodimers with the anti-apoptotic members, some of the pro-apoptotic members (e.g., Bik) can dislodge Apaf-1 allowing it to self-associate and participate in caspase-9 activation. The pro-apoptotic Bax molecule can act directly on mitochondria to release cytochrome c. Cytochrome c release from mitochondria can also be induced by the pro-apoptotic Bid molecule following its cleavage by active caspase-8; thereby linking the TNF-R and mitochondrial pathways.

Figure 5:
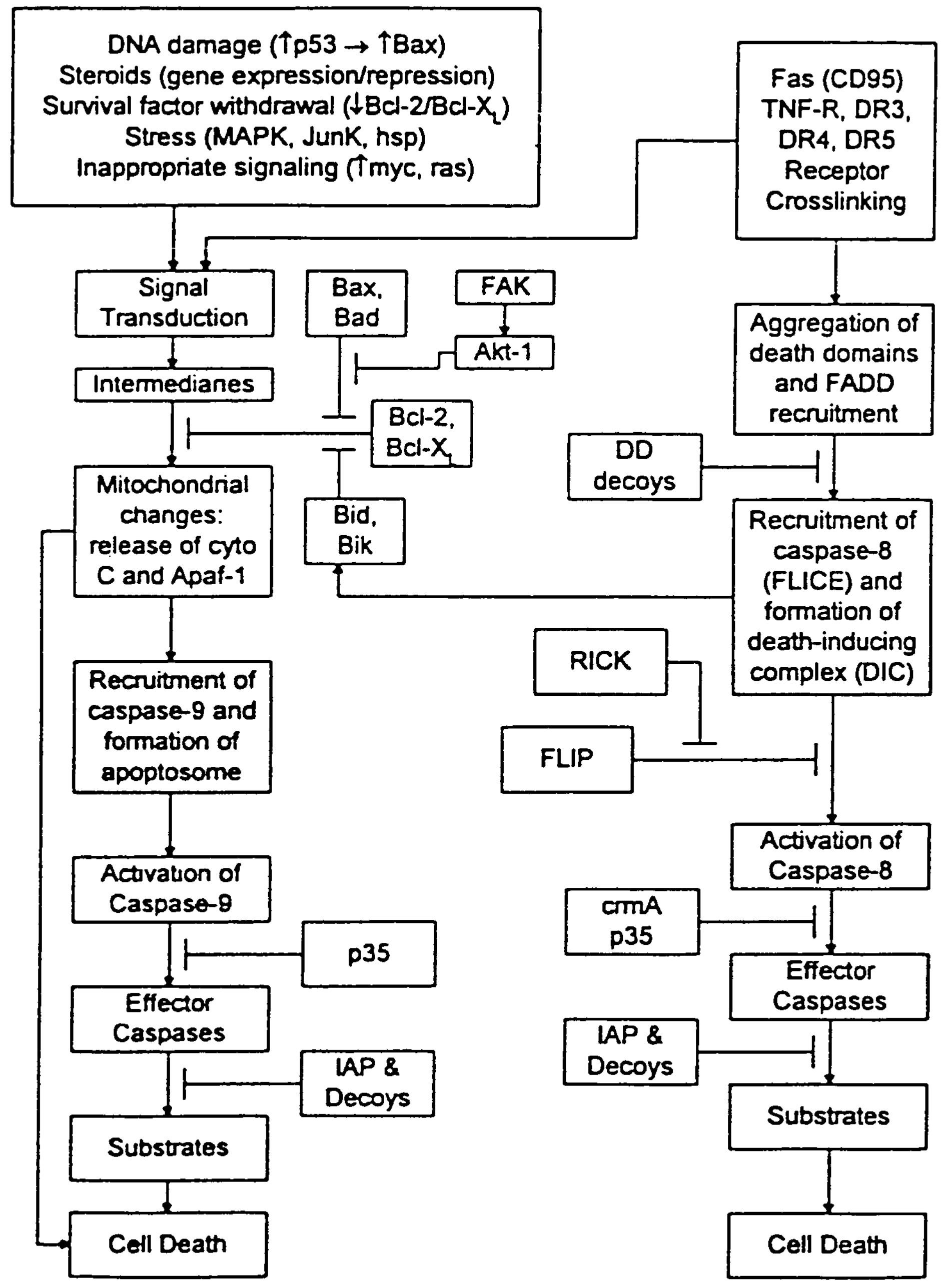
FIG. 5 is a schematic drawing showing the interactions of various apoptosis-inducing proteins and apoptosis-inhibiting proteins.

FIG. 5 is a schematic drawing showing the points of interaction of various apoptosis-inducing proteins and apoptosis-inhibiting proteins in both the caspase-8 and the caspase-9 pathways. All such proteins are encompassed by the present invention for use in the production/propagation of a recombinant viral vector according to the present invention.

Preferred apoptosis-inducing proteins to be encoded by a recombinant viral vector according to the present invention include, but are not limited to, Fas ligand, Fas, tumor necrosis factor (TNF), tumor necrosis factor receptor (TNFR), Fas-associating death domain-containing protein (FADD), Fas-associated death domain-like IL-1β, converting enzyme (FLICE), (TWEAK/Apo3L, Apo3, tumor necrosis factor-related apoptosis inducing ligand (TRAIL/Apo2L), Apo2, Bax, Bid, Bik, Bad, Bak, RICK, caspase-9, caspase-3, caspase-4, caspase-5, caspase-6, caspase-7, caspase-10, Apaf-1, cytochrome c, YAMA or biologically active homologues thereof (defined below). Members of the caspase-8 family of proteins include, but are not limited to, TNF, TNFR1, Fas ligand, Fas, Apo2, TRAIL, Apo3, TWEAK, FADD, FLICE, and caspases 3, 4, 5, 6, 7, 10, etc. Members of the caspase-9 family of proteins include, but are not limited to, cytochrome c, Apaf-1 (apoptosis protease activating protein), caspase-9 and caspases 3, 4, 5, 6, 6, 10, etc. Particularly preferred apoptosis-inducing proteins to be encoded by a recombinant viral vector according to the present invention include, but are not limited to, Fas ligand, Fas, tumor necrosis factor (TNF), Fas-associating death domain-containing protein (FADD), Fas-associated death domain-like IL-1β converting enzyme (FLICE), TWEAK/Apo3L, TRAIL/Apo2L, Bax, Bid, Bik, Bad, Bak, and RICK. The nucleic acid and amino acid sequences for these proteins in various mammalian species are known in the art, and many are disclosed herein. It is noted, however, that all of the nucleic acid and amino acid sequences of apoptosis-inducing and apoptosis-inhibiting proteins disclosed herein can be obtained from a public database such as Genbank.

A particularly preferred apoptosis-inducing protein to be encoded by a recombinant viral vector of the present invention is Fas ligand or a biologically active fragment thereof. For example, the nucleic acid sequence encoding a human Fas ligand protein is represented herein as SEQ ID NO:5. SEQ ID NO:5 encodes an amino acid sequence represented herein as SEQ ID NO:6. The nucleic acid sequence encoding a rat Fas ligand protein is represented herein as SEQ ID NO:7. SEQ ID NO:7 encodes an amino acid sequence represented herein as SEQ ID NO:8. The nucleic acid sequence encoding a mouse Fas ligand protein is represented herein as SEQ ID NO:9. SEQ ID NO:9 encodes an amino acid sequence represented herein as SEQ ID NO:10.

Nucleic acid and amino acid sequences for other apoptosis-inducing proteins discussed above are also known in the art, and a number of them are listed herein, although this list is not intended to be inclusive of sequences encompassed by the present invention. For example, the nucleic acid sequence encoding a human Fas protein is represented herein as SEQ ID NO:11. SEQ ID NO:11 encodes an amino acid sequence represented herein as SEQ ID NO:12. As discussed above, Fas (CD95/APO-1) is a transmembrane glycoprotein that is related to the receptors for tumor necrosis factor and nerve growth factor. Upon being cross-linked with agonistic anti-Fas antibodies or Fas ligand (FasL), Fas initiates a complex signal transduction pathway that, in sensitive cell types, ultimately ends in apoptotic cell death.

The nucleic acid sequence encoding a human FADD protein is represented herein as SEQ ID NO:13. SEQ ID NO:13 encodes an amino acid sequence represented herein as SEQ ID NO:14. Fas-associating death domain-containing protein (FADD), also known as MORT1, is a cytosolic adaptor protein which is critical for signaling from CD95 (Fas) and certain other members of the tumor necrosis family. Fan et al. recently demonstrated that oligomerization of the death effector domain of FADD is sufficient to trigger apoptosis (Fan et al., 1999*, Hum. Gene Ther.* 10:2273-2285). The nucleic acid sequence encoding human FLICE is represented herein as SEQ ID NO:15. SEQ ID NO:15 encodes an amino acid sequence represented herein as SEQ ID NO:16. Fas-associated death domain-like IL-1β converting enzyme (FLICE) is also referred to as caspase-8, MACH or Mch5. FLICE is a cysteine protease that interacts with FADD and plays a critical role in the Fas signaling pathway. Nucleic acid sequences encoding other human apoptosis-inducing proteins, and the amino acid sequences encoded thereby include, but are not limited to, for example, tumor necrosis factor (TNF) (SEQ ID NO:17/SEQ ID NO:18=nucleic acid sequence/amino acid sequence); TWEAK (SEQ ID NO:19/SEQ ID NO:20); TRAIL (SEQ ID NO:21/SEQ ID NO:22); Apo2L (SEQ ID NO:23/SEQ ID NO:24); Bax (SEQ ID NO:25/SEQ ID NO:26); Bid (SEQ ID NO:27/SEQ ID NO:28); Bik (SEQ ID NO:29/SEQ ID NO:30); Bad (SEQ ID NO:31/SEQ ID NO:32); Bak (SEQ ID NO:33/SEQ ID NO:34); and RICK (SEQ ID NO:35/SEQ ID NO:36).

In a preferred embodiment of the present invention, a recombinant viral vector of the present invention comprises a nucleic acid sequence that encodes an apoptosis-inducing protein having an amino acid sequence selected from the group of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, and biologically active homologues thereof. In another embodiment, a recombinant viral vector of the present invention comprises a nucleic acid sequence selected from the group of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or homologues of such sequences that encode a protein having apoptosis-inducing biological activity.

Preferred apoptosis-inhibiting proteins to be encoded by a recombinant nucleic acid molecule according to the present invention include, but are not limited to, Cowpox virus caspase inhibitor (CrmA), baculovirus p35, inhibitor of apoptosis protein (IAP), dominant negative FADD, dominant negative Fas, FLIP, Bcl-2, Bcl-$X_L$, adenovirus E1B- 19K protein, or biologically active homologues thereof (defined below). Of this list of proteins, CrmA, baculovirus p35 and IAP are inhibitors of caspase activity; dominant negative FADD, dominant negative Fas, and FLIP are inhibitors of caspase-8 activation; and Bcl-2, Bcl-$X_L$, and adenovirus E1B-19K protein are inhibitors of caspase-9 activation. A particularly preferred apoptosis-inhibiting protein for use in the present invention is CrmA. Nucleic acid and amino acid sequences for such apoptosis-inhibiting proteins are known in the art, and a number of them are listed herein, although this list is not intended to be inclusive of sequences encompassed by the present invention.

For example, the nucleic acid sequence encoding CrmA is represented herein as SEQ ID NO:37. SEQ ID NO:37 encodes an amino acid sequence represented herein as SEQ ID NO:38. Nucleic acid molecules encoding crmA and homologues thereof are described in PCT Publication WO 96/25501, ibid. Cowpox virus caspase inhibitor, or CrmA, is a protein that can inhibit Fas- and TNF-mediated apoptosis. Nucleic acid sequences encoding other apoptosis-inhibiting proteins, and the amino acid sequences encoded thereby include, but are not limited to, for example, human inhibitor of apoptosis protein (IAP) (SEQ ID NO:39/SEQ ID NO:40=nucleic acid sequence/amino acid sequence); human dominant negative Fas (SEQ ID NO:41/SEQ ID NO:42; or alternatively, a truncated naturally occurring Fas where at least a portion of the "death domain" from nucleotide positions 1029-1199 of SEQ ID NO:11 or amino acid positions 279-335 of SEQ ID NO:12 are removed); human FLIP (SEQ ID NO:43/SEQ ID NO:44); human Bcl-2 (SEQ ID NO:45/SEQ ID NO:46); human Bcl-$X_L$ (SEQ ID NO:47/SEQ ID NO:48); adenovirus E1B-19K (SEQ ID NO:49/SEQ ID NO:50) and human dominant negative FADD (truncated version of naturally occurring FADD comprising nucleotide positions 367-753 of SEQ ID NO:13 and amino acid positions 80-208 of SEQ ID NO:14).

In a preferred embodiment of the present invention, a recombinant nucleic acid molecule comprising a nucleic acid sequence that encodes an apoptosis-inhibiting protein encodes a protein comprising an amino acid sequence selected from the group of SEQ ID NO:38, SEQ ID NO:39, SEQ ID NO:40, SEQ ID NO:42, SEQ ID NO:44, SEQ ID NO:46, SEQ ID NO:48, SEQ ID NO:50, amino acid positions 80-208 of SEQ ID NO:14, and biologically active homologues thereof. In another embodiment, a recombinant nucleic acid molecule comprising a nucleic acid sequence encoding an apoptosis-inhibiting protein is selected from the group of SEQ ID NO:37, SEQ ID NO:39, SEQ ID NO:41, SEQ ID NO:43, SEQ ID NO:45, SEQ ID NO:47, SEQ ID NO:49, nucleotide positions 367-753 of SEQ ID NO:13, or homologues of such sequences that encode a protein having apoptosis-inducing biological activity.

According to the present invention, an isolated, or biologically pure, protein, is a protein that has been removed from its natural milieu. As such, "isolated" and "biologically pure" do not necessarily reflect the extent to which the protein has been purified. An isolated protein, as used herein with regard to apoptosis-inhibiting proteins and/or apoptosis-inducing proteins, is preferably produced using recombinant DNA technology. As used herein, reference to a particular protein (e.g., an apoptosis-inducing protein or an apoptosis-inhibiting protein) includes a full-length protein or any homologue of such a protein. Protein homologues are variants of a naturally occurring protein in which at least one or a few, but not limited to one or a few, amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue includes at least one epitope capable of eliciting an immune response against the corresponding naturally occurring protein and/or has a biological activity of the corresponding naturally occurring protein. To be "capable of eliciting an immune response" indicates that when the homologue is administered to an animal as an immunogen, using techniques known to those skilled in the art, the animal will produce a humoral and/or cellular immune response against at least one epitope of the naturally occurring protein. To have "biological activity of the naturally occurring protein" indicates that the protein is sufficiently structurally similar to the corresponding naturally occurring protein such that the protein has biological activity substantially similar to the naturally occurring protein. The biological activity of a protein can include the ability of a protein to bind to another protein or molecule, to activate another molecule, to become activated, and/or to perform the naturally occurring function of the protein in a cell or biological system. The biological activity of the apoptosis-inducing and apoptosis-inhibiting proteins disclosed herein can be measured using methods known in the art. For example, CrmA biological activity can be measured by its ability to inhibit Fas-induced or TNF-induced apoptosis in an in vitro assay, for example, as described in PCT Publication No. WO 96/25501, which is incorporated herein by reference in its entirety. It is to be understood that the biological activity of a homologue of the preset invention is a qualitative, rather than a quantitative, characteristic, in that a protein homologue having the biological activity of a naturally occurring protein function as the naturally occurring protein (e.g., inhibiting or inducing apoptosis in a cell), but can do so at a greater, equal or lesser measurable degree than the naturally occurring protein.

In one embodiment, the minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Apoptosis-inducing protein homologues of the present invention have the ability to induce apoptosis in a cell under suitable conditions as described herein and/or are capable of eliciting an immune response against a naturally occurring apoptosis-inducing protein. Apoptosis-inhibiting protein homologues of the present invention have the ability to inhibit apoptosis in a cell under suitable conditions as described herein and/or are capable of eliciting an immune response against a naturally occurring apoptosis-inhibiting protein.

In one embodiment, a homologue of an apoptosis-inducing or apoptosis-inhibiting protein of the present invention comprises an amino acid sequence comprising at least about 6, and more preferably at least about 12 and more preferably at least about 24 contiguous amino acid residues of an amino acid sequence of a naturally occurring (i.e., wild-type) protein. In another embodiment, a homologue is encoded by a nucleic acid sequence comprising at least about 18, and more preferably at least about 36, and even more preferably at least about 72 contiguous nucleotides of a nucleic acid sequence encoding a naturally occurring protein.

Protein homologues can be the result of natural allelic variation or natural mutation. According to the present invention, protein homologues can also be produced using techniques known in the art including, but not limited to, direct modifications to the protein or modifications to the gene encoding the protein using, for example, classic or recombinant DNA techniques to effect random or targeted mutagenesis.

It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. According to the present invention, a nucleic acid molecule encoding a given protein (e.g., a Fas ligand protein) can include an isolated natural gene, a portion of such a gene or a homologue thereof, the latter of which is described in more detail below. As used herein, a nucleic acid molecule can include one or more regulatory regions, full-length or partial coding regions, or combinations thereof. The minimal size of such a nucleic acid molecule is the minimal size that can form a stable hybrid with a naturally occurring gene under stringent hybridization conditions. An isolated nucleic acid molecule can be obtained from its natural source either as an entire (i.e., complete) gene or a portion thereof capable of forming a stable hybrid with that gene. An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode the desired protein which is useful in the present invention or to form stable hybrids under stringent conditions with natural gene isolates.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, stringent hybridization and washing conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M $Na^+$) at a temperature of between about 30° C. and about 45° C., more preferably, between about 38 ° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 TO 9.62.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of the naturally occurring protein, ability to selectively bind to immune serum, ability to bind to glutathione), by hybridization with the naturally occurring gene, and/or by the desired biological activity.

The present invention also includes nucleic acid molecules encoding an apoptosis-inhibiting protein or an apoptosis-inducing protein that have been modified to accommodate codon usage properties of the cells in which such nucleic acid molecules are to be expressed.

Knowing the nucleic acid sequences of certain nucleic acid molecules useful in the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain similar nucleic acid molecules from other mammals, particularly since, as described in detail in the Examples section, knowledge of a nucleic acid molecule from one species (e.g., rat Fas ligand) enables the isolation of the corresponding nucleic acid molecule from another species (e.g., human Fas ligand). Such nucleic acid molecules can be obtained in a variety of ways including screening appropriate expression libraries with antibodies against the protein encoded by the desired nucleic acid molecule; traditional cloning techniques using oligonucleotide probes, such as those of the present invention for Fas ligand, to screen appropriate libraries or DNA; and PCR amplification of appropriate libraries or DNA using oligonucleotide primers.

The present invention also includes a recombinant vector, which can be any vector capable of enabling recombinant production of a protein and/or which can deliver the nucleic acid molecule into a host cell. Such a vector contains heterologous nucleic acid sequences (e.g., nucleic acid sequences that are not naturally found adjacent to the nucleic acid molecule to be expressed). The vector can be either RNA or DNA, either prokaryotic or eukaryotic, and typically is a virus or a plasmid. Recombinant vectors can be used in the cloning, sequencing, and/or otherwise manipulating of nucleic acid molecules useful in the present invention. Preferred recombinant vectors are capable of replicating when transformed into a suitable host cell. As used herein, a recombinant vector which is linked to a nucleic acid sequence encoding the desired protein (e.g., an apoptosis-inhibiting protein or an apoptosis-inducing protein) can be referred to herein as either a recombinant vector or a recombinant molecule. Recombinant viral vectors of the present invention are described in detail below.

A recombinant molecule of the present invention is a molecule that can include at least one of any nucleic acid molecule encoding an apoptosis-inhibiting protein or a nucleic acid molecule encoding an apoptosis-inducing protein operatively linked to at least one of any transcription control sequence capable of effectively regulating expression of the nucleic acid molecule(s) in the cell to be transformed, examples of which are disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

The recombinant nucleic acid molecule comprising a nucleic acid sequence encoding an apoptosis-inhibiting protein and the recombinant viral vector comprising a nucleic acid sequence encoding an apoptosis-inducing protein can either be separate molecules, both of which are introduced into the production cell line, or alternatively, the recombinant nucleic acid molecule comprising a nucleic acid sequence encoding an apoptosis-inhibiting protein can be contained within (i.e., is a portion of) the recombinant viral vector that comprises a nucleic acid sequence encoding an apoptosis-inducing protein. In this latter instance, the nucleic acid sequence encoding an apoptosis-inhibiting protein can be operatively linked to either the same transcription control sequence as the nucleic acid sequence encoding an apoptosis-inducing protein, or to a different transcription control sequence. In one embodiment, when the two nucleic acid sequences are operatively linked to the same transcription control sequence, the nucleic acid sequence encoding an apoptosis-inhibiting protein and the nucleic acid sequence encoding an apoptosis-inducing protein are separated in the recombinant viral vector by an internal ribosome entry site (IRES) (described in detail below).

Therefore, one embodiment of the present invention relates to a recombinant viral vector for inducing apoptosis in cells infected by the vector. The vector includes: (a) a nucleic acid sequence encoding an apoptosis-inhibiting protein operatively linked to a transcription control sequence and (b) a nucleic acid sequence encoding an apoptosis-inducing protein operatively linked to a transcription control sequence. The nucleic acid sequences of (a) and (b) can be operatively linked to the same or different transcription control sequences, and when linked to the same transcription control sequence, are preferably separated by an IRES.

In a recombinant molecule of the present invention, including a recombinant viral vector, nucleic acid molecules are operatively linked to expression vectors containing regulatory sequences such as transcription control sequences, translation control sequences, origins of replication, and other regulatory sequences that are compatible with the recombinant cell and that control the expression of nucleic acid molecules of the present invention and/or the propagation of the recombinant viral vector, when applicable. In particular, recombinant molecules of the present invention include nucleic acid sequences that are operatively linked to one or more transcription control sequences. The phrase "operatively linked" refers to linking a nucleic acid sequence to a transcription control sequence in a manner such that the molecule is able to be expressed when transfected (i.e., transformed, transduced, infected or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rmB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, α-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Particularly preferred transcription control sequences include tissue-specific promoters (e.g., insulin promoters, α-myosin heavy chain promoter and endothelin promoter) and enhancers, as well as lymphokine-inducible promoters (e.g., promoters inducible by interferons or interleukins) and constitutively active promoters (e.g., β-activin promoter and ubiquitin promoter). Transcription control sequences of the present invention can also include naturally occurring transcription control sequences naturally associated with the protein to be expressed prior to isolation.

According to the present invention, a recombinant molecule can be dicistronic. A cistron refers to a unit of DNA that is capable of encoding an amino acid sequence having a naturally-occurring biological function. A dicistronic plasmid refers to a plasmid containing two cistrons. Preferably, a dicistronic recombinant molecule of the present invention comprises an internal ribosome entry site (IRES) element to which eukaryotic ribosomes can bind (see, for example, Jang et al., *J. Virol.* 62:2636-2643, 1988; Pelletier et al. *Nature* 334:320-325, 1988; Jackson, *Nature* 353:14-15, 1991; Macejek et al., *Nature* 353:90-94, 1991; Oh et al., *Genes & Develop.* 6:1643-1653, 1992; Molla et al., *Nature* 356:255-257, 1992; and Kozak, *Crit. Rev. Biochem. Molec. Biol.* 27(4, 5):385-402, 1992).

Recombinant molecules of the present invention may also (a) contain secretory signals (i.e., signal segment nucleic acid sequences) to enable an expressed protein to be secreted from the cell that produces the protein and/or (b) contain fusion sequences which lead to the expression of nucleic acid molecules as fusion proteins. Eukaryotic recombinant molecules may include intervening and/or untranslated sequences surrounding and/or within the nucleic acid sequences of nucleic acid molecules. Suitable signal segments include any signal segment capable of directing the secretion of a given protein. Preferred signal segments include, but are not limited to, tissue plasminogen activator (t-PA), interferon, interleukin, growth hormone, histocompatibility and viral envelope glycoprotein signal segments.

The method of the present invention is used for propagation of a recombinant viral vector comprising a nucleic acid sequence encoding an apoptosis-inducing protein. Such a vector includes a recombinant molecule of the present invention that is packaged in a viral coat and that can be expressed in an animal or recombinant cell after administration. Preferably, the viral vector is capable of being propagated (e.g., replicated and packaged) when introduced into an appropriate host cell (e.g., a production cell line). In one embodiment, the recombinant viral vector is packaging- and/or replication-deficient. A number of recombinant viral vectors can be used, including, but not limited to, those based on alphaviruses, poxviruses, adenoviruses, herpesviruses, lentiviruses, adeno-associated viruses, vaccinia viruses, baculoviruses, parvoviruses and retroviruses. Particularly preferred viral vectors are those based on adenoviruses, adeno-associated viruses and lentiviruses. When introduced into a production cell line that is capable of replicating and packaging the viral vector (e.g., a cell that has been transformed with or naturally carries viral genes required for replication and/or packaging of a virus from which the viral vector is derived), the recombinant viral vector is propagated. Moreover, when infected into a recipient host cell under the appropriate conditions according to the present invention, a recombinant viral vector of the present invention can direct the production of the encoded apoptosis-inducing protein. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Wash. D.C., 1998, pp. 555!-590, the entirety of which is incorporated herein by reference. One viral vector for use in the present invention is a human adenovirus 5 construct under the control of a CMV immediate early promoter. A viral vector encoding a Fas ligand protein is described in detail in the Examples section, and comprises a nucleic acid sequence that comprises at least a portion of a nucleic acid sequence represented herein by SEQ ID NO:4. Referring to SEQ ID NO:4, the CMV immediate early promoter, coding sequence, SV40 small t intron and SV40 polyA can be inserted between nucleotides 454 and 455. Therefore, a viral vector encoding Fas ligand protein can include all or a sufficient portion of SEQ ID NO:4 (e.g., sufficient to produce a recombinant viral vector according to the present invention), with the promoter, coding sequence and other required regulatory sequences, such as the SV40 sequences referenced above, inserted at the above-designated position.

An adenoviral vector is one preferred vector for use in the present methods. An adenoviral vector infects a wide range of nondividing human cells and has been used extensively in live vaccines without adverse side effects. Adenoviral vectors do not integrate into the host genome, and therefore, gene therapy using this system requires periodic administration, although methods have been described which extend the expression time of adenoviral transferred genes, such as administration of antibodies directed against T cell receptors at the site of expression (Sawchuk et al., 1996, *Hum. Gene. Ther.* 7:499-506). It is noted, however, that for use in the therapeutic methods of the present invention as described below, it is typically not necessary that the expression of the apoptosis-inducing protein by the viral vector be long-term, and in fact, short term expression is typically preferred. More particularly, expression of an apoptosis-inducing protein in the methods of the present invention (e.g., for the induction of tolerance and/or elimination of targeted host lymphocytes or for cancer therapy) is preferably accomplished by short term exposure of the target cells to the protein. Such short term exposure is sufficient to be effective for induction of apoptosis in a target cell (and/or tolerance, in the case of lymphocytes), and minimizes potential undesirable side effects of having an apoptosis-inducing protein available in a patient, which would increase with long-term expression.

The efficiency of adenovirus-mediated gene delivery can be enhanced by developing a virus that preferentially infects a particular target cell. For example, a gene for the attachment fibers of adenovirus can be engineered to include a DNA element that encodes a protein domain that binds to a cell-specific receptor. Examples of successful in vivo delivery of genes has been demonstrated and are discussed in more detail below.

Yet another type of viral vector is based on adeno-associated viruses, which are small, nonpathogenic, single-stranded human viruses. This virus can integrate into a specific site on chromosome 19. This virus can carry a cloned insert of about 4.5 kb, and has typically been successfully used to express proteins in vivo from 70 days to at least 5 months. Demonstrating that the art is quickly advancing in the area of gene therapy, however, a recent publication by Bennett et al. reported efficient and stable transgene expression by adeno-associated viral vector transfer in vivo for greater than 1 year (Bennett et al., 1999, *Proc. Natl. Acad. Sci. USA* 96:9920-9925). As discussed above, however, the methods of the present invention do not typically require long-term expression, and so any of the viral vectors described herein would be sufficient for use in the therapeutic methods of the present invention.

When it is desired to have a nucleic acid sequence inserted into the host genome for long term expression, a retroviral vector can be packaged in the envelope protein of another virus so that it has the binding specificity and infection spectrum that are determined by the envelope protein (e.g., a pseudotyped virus). In addition, the envelope gene can be genetically engineered to include a DNA element that encodes and amino acid sequence that binds to a cell receptor to create a recombinant retrovirus that infects a specific cell type. Expression of the gene (e.g., a Fas ligand gene) can be further controlled by the use of a cell or tissue-specific promoter. Retroviral vectors have been successfully used to transfect cells with a gene which is expressed and maintained in a variety of ex vivo systems.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., Shine-Dalgarno sequences), modification of nucleic acid molecules to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

According to the method of the present invention, a recombinant viral vector comprising a nucleic acid molecule encoding an apoptosis-inducing protein can be propagated by culturing a production cell line, also referred to generally as an isolated cell, that has been transfected with a recombinant nucleic acid molecule encoding an apoptosis-inducing protein operatively linked to a transcription control sequence, and with a recombinant viral vector comprising a recombinant nucleic acid molecule comprising a nucleic acid sequence encoding a protein that induces apoptosis in a cell. An isolated cell transfected with a recombinant viral vector and/or other recombinant nucleic acid molecule can also generally be referred to as a recombinant cell. As used herein, an isolated cell which is used to propagate a recombinant viral vector, can also be referred to as a production cell or cell line, and an isolated cell that is used to produce an apoptosis-inducing protein (such as in a therapeutic method of the present invention) can be referred to as a host cell. In some instances, a production cell and a host cell are the same cell. For example, the production cell line can also be capable of expressing the apoptosis-inducing protein under conditions effective to produce the protein, if desired (e.g., when administered to a patient to suppress graft rejection). Alternatively, the propagated viral vector can be recovered from the production cell line and transfected into another suitable host cell where the apoptosis-inducing protein can be expressed. An isolated cell that is used to carry a recombinant vector or molecule to an appropriate in vitro or in vivo site can also be referred to as a pharmaceutically acceptable carrier. Transfection of a recombinant nucleic acid molecule or a recombinant viral vector into a cell can be accomplished by any method by which a nucleic acid molecule can be inserted into the cell. Transfection techniques include, but are not limited to, transformation, electroporation, microinjection, lipofection, adsorption, infection and protoplast fusion. In the case of a recombinant viral vector, the host cell is preferably transfected by infection.

A host cell that has been transfected with a recombinant nucleic acid molecule and/or a recombinant viral vector can be referred to herein as a recombinant cell. A recombinant cell may remain unicellular or may grow into a tissue, organ or a multicellular organism. Preferably, a recombinant cell of the present invention is suitable for propagating the recombinant viral vector encoding an apoptosis-inducing protein. Such a cell is typically referred to herein as a production cell, and for some viral vectors, is referred to as a packaging cell line. Transfected nucleic acid molecules of the present invention can remain extrachromosomal or can integrate into one or more sites within a chromosome of the transfected (i.e., recombinant) cell in such a manner that their ability to be expressed is retained.

Suitable cells to transfect for the method of propagating a viral vector according to the present invention include any isolated cell that can be transfected with a recombinant nucleic acid molecule and a recombinant viral vector, and which can replicate the viral vector. For example, packaging cell lines are specialized cells in that they have additionally been transfected with or naturally contain viral genes which allow the transfected viral vector to be propagated. Isolated production cells can be either untransfected cells or cells that are already transfected with at least one nucleic acid molecule. Isolated cells of the present invention can be any cell capable of producing a recombinant protein and/or capable of propagating a recombinant viral vector and include mammalian, bacterial, fungal (including yeast), parasite, insect, other animal and plant cells. In one embodiment of the present invention, preferred production cells include bacterial, insect and mammalian cells. Particularly preferred production cells include embryonal kidney cells, such as the 293 cell line described in the Examples section. 293 (ATCC Accession No. CRL-1573) has been transformed by the E1 region of the adenovirus 5 chromosome and is therefore useful for propagating viral vectors derived from adenoviruses.

In one embodiment of the present invention, and particularly, therapeutic methods of the present invention, a suitable cell to be transfected with a recombinant viral vector encoding an apoptosis-inducing protein includes host cells (e.g., cells which are to be the final recipient of or the carrier of the recombinant viral vector), such as any mammalian cells which are useful and desirable as a transplantable graft (e.g., an insulin-producing beta cell). Such a host cell can also be a part of an organ which is to be transplanted (e.g., a kidney having multiple cells transformed with Fas ligand). Additionally, such a host cell can be any cell which is transplanted in conjunction with another non-transformed cell or organ (i.e., a fibroblast cell which has been transformed to express Fas ligand that is transplanted with a non-transformed beta cell or a kidney comprising non-transformed cells). In certain embodiments, discussed below, such a host cell can also be transfected with a recombinant nucleic acid molecule encoding an apoptosis-inhibiting protein as described herein.

Effective conditions for propagation of a recombinant viral vector and/or effective conditions to produce an apoptosis-inducing protein include, but are not limited to, appropriate media, bioreactor, temperature, pH and oxygen conditions that permit viral propagation and/or protein production. Similarly, effective conditions for induction of apoptosis in a cell include, but are not limited to, the presence of a required cofactor or receptor for induction of apoptosis, and culture or environmental conditions which allow apoptosis to occur. An effective medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the isolated cell. Such culturing conditions are well within the expertise of one of ordinary skill in the art. Examples of suitable conditions are included in the Examples section.

Depending on the vector and host system used for production, resultant recombinantly produced proteins may either remain within the isolated cell (i.e., be expressed internally); be secreted into the culture medium; be secreted into a space between two cellular membranes, such as the periplasmic space in *E. coli*; or be retained on the outer surface of a cell or viral membrane.

The phrase "recovering the viral vector" or "recovering the protein" refers simply to collecting the whole culture medium containing the viral vector and/or protein and need not imply additional steps of separation or purification. Recombinant viral vectors can be recovered from production cells using a variety of standard techniques, including but not limited to lysis, centrifugation, and chromatography. Apoptosis-inducing proteins can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Using the production method of the present invention, a viral vector encoding an apoptosis-inducing protein according to the present invention can be replicated to a viral titer of at least about $1\times10^8$ pfu per ml of supernatant isolated from the cell (i.e., using standard methods for isolating virus from a production cell line) and more preferably at least about $5\times10^8$ pfu per ml of supernatant isolated from the cell, and even more preferably at least about $1\times10^9$ pfu per ml of supernatant isolated from the cell, and even more preferably at least about $5\times10^9$ pfu per ml of supernatant isolated from the cell, and even more preferably at least about $1\times10^{10}$ pfu per ml of supernatant isolated from the cell, without damaging or destroying the production cell (i.e., the packaging cell line).

The recombinant viral vector of the present invention, isolated cells transfected with such a recombinant viral vector, and the method of propagating such a recombinant viral vector, are useful in embodiments of the present invention related to therapeutic methods of preventing and treating diseases and conditions including graft rejection, cancer and T-lymphocyte mediated diseases. Accordingly, another embodiment of the present invention relates to a method of suppressing T-lymphocyte-mediated graft rejection in a recipient mammal. The method comprises introducing into the mammal a pharmaceutically acceptable carrier comprising a recombinant viral vector comprising a nucleic acid sequence encoding a protein that induces apoptosis operatively linked to a transcription control sequence. In one embodiment of this method, the pharmaceutically acceptable carrier can additionally comprise a recombinant nucleic acid molecule comprising a nucleic acid sequence encoding a protein that inhibits apoptosis operatively linked to a transcription control sequence. In this embodiment, the nucleic acid sequence encoding the apoptosis-inhibiting protein is preferably contained within the recombinant viral vector, although the recombinant nucleic acid molecule can be administered as a separate molecule, particularly when delivered to a cell by ex vivo methods. When the nucleic acid sequence encoding the apoptosis-inhibiting protein is within the recombinant viral vector, the nucleic acid sequence encoding this protein and the nucleic acid sequence encoding the apoptosis-inducing protein can be operatively linked to the same or different transcription control sequences, and when linked to the same transcription control sequence, are preferably separated by an IRES. Such vectors, recombinant molecules, apoptosis-inducing proteins and apoptosis-inhibiting proteins have been described above. In one embodiment, the apoptosis-inducing protein is Fas ligand.

In one embodiment, the pharmaceutically acceptable carrier is an isolated cell that is transfected with the recombinant viral vector, alone or in combination with the recombinant nucleic acid molecule encoding an apoptosis-inhibiting protein. In this embodiment, the cell preferably has the characteristics of a suitable host cell of the present invention as described above. Specifically, the cellular carrier should be capable of expressing the apoptosis-inducing protein and, when included, the apoptosis-inhibiting protein. According to the present invention, the apoptosis-inhibiting protein is included in the pharmaceutically acceptable carrier when it is desirable to protect the carrier cell from undergoing apoptosis. In one embodiment, the cellular carrier is capable of expressing the apoptosis-inducing protein at the site of transplantation. In one embodiment, the carrier cell is a part of a graft to be transplanted in a recipient, although the cell does not necessarily need to be a part of the graft (e.g., the cell can be a heterologous cell that is associated with the graft ex vivo for the purposes of providing an apoptosis-inducing protein to protect the graft). In the former embodiment, the transplanted tissue itself functions as a source of an apoptosis-inducing protein, which in a preferred embodiment, is Fas ligand. In this embodiment, transplanted tissue is obtained from a non-human animal is transfected with the recombinant viral vector encoding the apoptosis-inducing protein and in some embodiments, with a recombinant nucleic acid molecule encoding an apoptosis-inhibiting protein. As discussed above, the recombinant nucleic acid molecule encoding an apoptosis-inhibiting protein can be contained within the recombinant viral vector, or can be transfected as a separate nucleic acid molecule. The transfected cells maintain their ability to express biologically active apoptosis-inducing protein when transplanted into the recipient host animal. The invention includes the transplant of apoptosis-inducing protein-expressing tissue alone (e.g., transplant of transgenic islet cells into a diabetic patient) or transplantation of apoptosis-inducing protein-expressing autologous tissue along with non-manipulated donor tissue (e.g., transplant of a non-transgenic islet cells to a patient in need thereof with apoptosis-inducing protein-expressing tissue to the graft site, thereby creating an artificial immunologically-privileged site). In this latter case, the transplanted apoptosis-inducing protein-expressing tissue functions to suppress rejection of the transplanted islet cells. Preferred methods of administering such a pharmaceutically acceptable carrier are discussed in detail below.

According to the present invention, donor tissue may he obtained from the same or a different species as the recipient mammal. The term “donor tissue”, includes cells and organs from a donor mammal, including but not limited to islet cells, kidney, heart, liver, lung, brain, and muscle tissue. In one embodiment, the donor tissue may be obtained from any mammal, and preferably pigs. Pigs offer many advantages for use as organ and cell donor animals. For example, many porcine organs, such as the heart and kidney, are of a similar size to human organs. In another embodiment of the present invention, allogeneic cells (i.e., cells derived from a source other than a patient, but that are histotype compatible with the patient) or autologous cells (i.e., cells isolated from a patient) are transfected with recombinant viral vector described herein. Such cells can then be referred to as a portion of a therapeutic composition for suppressing graft rejection in the mammal. Such a therapeutic composition is then administered to a patient by any suitable means of administration, including, but not limited to, intradermal, intravenous or subcutaneous injection, or direct injection at the site of transplantation during transplant surgery.

In one embodiment, the pharmaceutically acceptable carrier can include a liposome which contains the recombinant viral vector and delivers the vector to a suitable site in a host recipient. According to the present invention, a liposome pharmaceutically acceptable carrier comprises a lipid composition that is capable of delivering a recombinant nucleic acid molecule or viral vector of the present invention to a suitable cell and/or tissue in a mammal. A liposome pharmaceutically acceptable carrier of the present invention comprises a lipid composition that is capable of fusing with the plasma membrane of the target cell to deliver the recombinant nucleic acid molecule and/or viral vector into a cell. A liposome pharmaceutically acceptable carrier of the present invention can be modified to target a particular site in a mammal (i.e., a targeting liposome), such as the site of transplantation, thereby targeting and making use of a nucleic acid molecule of the present invention at that site. Suitable modifications include manipulating the chemical formula of the lipid portion of the pharmaceutically acceptable carrier. Manipulating the chemical formula of the lipid portion of the pharmaceutically acceptable carrier can elicit the extracellular or intracellular targeting of the pharmaceutically acceptable carrier. For example, a chemical can be added to the lipid formula of a liposome that alters the charge of the lipid bilayer of the liposome so that the liposome fuses with particular cells having particular charge characteristics. Other targeting mechanisms include targeting a site by addition of exogenous targeting molecules to a liposome such as an antibody, soluble receptor or ligand, incorporated with the liposome, to target a particular cell or tissue to which the targeting molecule can bind. Targeting liposomes are described, for example, in Ho et al., 1986, *Biochemistry* 25: 5500-6; Ho et al., 1987 a, *J Biol Chem* 262: 13979-84; Ho et al., 1987b, *J Biol Chem* 262: 13973-8; and U.S. Pat. No. 4,957,735 to Huang et al., each of which is incorporated herein by reference in its entirety). Alternatively, the route of administration, as discussed below, can be used to target a specific cell or tissue. For example, intravenous delivery of cholesterol-containing cationic liposomes has been shown to preferentially target pulmonary tissues (Liu et al., *Nature Biotechnology* 15:167, 1997), and effectively mediate transfer and expression of genes in vivo. Additionally, a recombinant nucleic acid molecule can be selectively (i.e., preferentially, substantially exclusively) expressed in a target cell by selecting a transcription control sequence, and preferably a promoter, which is selectively induced in the target cell and remains substantially inactive in non-target cells.

A liposome pharmaceutically acceptable carrier is preferably capable of remaining stable in a mammal for a sufficient amount of time to deliver a nucleic acid molecule of the present invention to a preferred site in the mammal. A liposome pharmaceutically acceptable carrier of the present invention is preferably stable in the mammal into which it has been administered for at least about 30 minutes, more preferably for at least about 1 hour and even more preferably for at least about 24 hours. A preferred liposome pharmaceutically acceptable carrier of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes commonly used in, for example, gene delivery methods known to those of skill in the art. Preferred liposome pharmaceutically acceptable carriers comprise multilamellar vesicle (MLV) lipids and extruded lipids. Methods for preparation of MLV's are well known in the art. According to the present invention, "extruded lipids" are lipids which are prepared similarly to MLV lipids, but which are subsequently extruded through filters of decreasing size, as described in Templeton et al., 1997, *Nature Biotech.,* 15:647-652, which is incorporated herein by reference in its entirety. Small unilamellar vesicle (SUV) lipids can also be used in the composition and method of the present invention. In one embodiment, liposome pharmaceutically acceptable carriers comprise liposomes having a polycationic lipid composition (i.e., cationic liposomes) and/or liposomes having a cholesterol backbone conjugated to polyethylene glycol.

Preferably, the transfection efficiency of a nucleic acid: liposome complex of the present invention is at least about 1 picogram (pg) of protein expressed per milligram (mg) of total tissue protein per microgram (μg) of nucleic acid delivered. More preferably, the transfection efficiency of a nucleic acid:liposome complex of the present invention is at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered.

In another embodiment of the present invention, pharmaceutically acceptable carrier can include a pharmaceutically acceptable excipient. As used herein, a pharmaceutically acceptable excipient refers to any substance suitable for delivering a therapeutic composition useful in the method of the present invention to a suitable in vivo site. In some embodiments, a recombinant viral vector can be administered directly to a mammal in the presence of a pharmaceutically acceptable excipient and in the absence of any additional carriers. Suitable excipients of the present invention include excipients or formularies that assist with the transport of cells and/or recombinant molecules to a site. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol.

The pharmaceutically acceptable carrier may be administered by a number of methods known in the art. In one embodiment of the invention, a pharmaceutically acceptable carrier comprising a recombinant viral vector of the present invention is administered in an effective amount to a mammal sufficient to prevent a T-lymphocyte-mediated transplant rejection or disease recurrence. The therapeutic or pharmaceutical composition of the invention may be administered in a variety of ways, including by in vivo or ex vivo delivery methods, as described below.

Ex vivo refers to performing part of the regulatory step outside of the mammal, such as by transfecting a population of cells removed from a mammal with a recombinant viral vector of the present invention under conditions such that the protein(s) encoded by the vector is subsequently expressed by the transfected cell, and returning the transfected cells to the mammal. As used herein, the term "transfection" can be used in a broad sense to refer to any method of introducing a molecule into a cell. Methods to achieve transfection include, but are not limited to, standard transfection, electroporation, microinjection, lipofection, adsorption, viral infection (e.g., transduction), naked DNA injection, protoplast fusion, and transformation. Ex vivo methods are particularly suitable when the pharmaceutically acceptable carrier is a cell, and most particularly, when the cell is part of a graft, such as a tissue or whole organ.

A pharmaceutically acceptable carrier is administered to a mammal in a fashion to enable expression of the apoptosis-inducing protein as a biologically active protein in the mammal receiving a transplant. A pharmaceutically acceptable carrier can be administered to an animal in a variety of methods including, but not limited to, local administration of the composition into a site in an animal (e.g., injection locally within the area of a transplant); ex vivo administration (e.g., transfecting the graft cells which are to be transplanted, and/or transfecting other non-graft cells to be transplanted with the graft), peripheral administration, and systemic administration.

One method of local administration is by direct injection. Direct injection techniques are particularly useful for suppressing graft rejection by, for example, injecting the composition into the transplanted tissue. Preferably, a recombinant viral vector of the present invention alone, or contained within a pharmaceutically acceptable carrier is administered by direct injection into or locally within the area of a transplanted tissue. Administration of a composition locally within the area of a transplanted tissue refers to injecting the composition centimeters and preferably, millimeters within the transplanted tissue. A preferred transplanted tissue to inject includes discrete organs, including, but not limited to kidney, lung, liver, and pancreas.

Preferred methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. Intravenous, intraperitoneal, and intramuscular administrations can be performed using methods standard in the art. Aerosol delivery can also be performed using methods standard in the art (see, for example, Stribling et al., *Proc. Natl. Acad. Sci.* USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Various methods of administration of a recombinant viral vector disclosed herein have been shown to be effective for delivery of a nucleic acid molecule to a target cell, whereby the nucleic acid molecule transfected the cell and was expressed. In many studies, successful delivery and expression of a heterologous gene was achieved using preferred pharmaceutically acceptable carriers and routes of administration of the present invention. All of the publications discussed below and elsewhere herein with regard to gene delivery and pharmaceutically acceptable carriers are incorporated herein by reference in their entirety. For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome pharmaceutically acceptable carrier, whereby the encoded proteins were expressed in tissues of the animal, and particularly in pulmonary tissues. Liu et al., 1997, ibid. demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811:299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480*; Bordignon et al.,* 1995, *Science* 270: 470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al., 1999, ibid. demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis.

Therapeutic compositions of the present invention can be administered to any animal, preferably to mammals, and more preferably to humans.

Example 1 describes the transplantation of rat islet cells into the renal subcapsular space of diabetic PVG rats. Pumps dispensing saline (controls) or purified Fas ligand (experimentals) are implanted in proximity to the graft site.

As an alternative to administration of an apoptosis-inducing protein to the graft site via the recombinant viral vector disclosed herein, transplant tissue can be grown in transgenic animals which have been genetically altered to contain the Fas ligand gene sequence. Such transgenic animals can be made by standard transgenic techniques (Example 2). Example 3 describes transplantation of islet cells from transgenic rats wherein the transplanted tissue itself is an endogenous source of Fas ligand.

In one embodiment, pharmaceutically acceptable carrier of the present invention is administered by injection or by continuous infusion from an implanted pump. Other appropriate administration forms are envisioned. For example, semipermeable implantable membrane devices that are useful as means for delivering drugs or medications are known. The encapsulation of cells that secrete neurotransmitter factors, and the implantation of such devices into the brain of patients suffering from Parkinson's disease has been described (See for example, U.S. Pat. Nos. 4,892,538; 5,011,472; 5,106,627).

An effective administration protocol (i.e., administering a therapeutic composition in an effective manner) comprises suitable dose parameters and modes of administration that result in suppression of graft rejection and/or treatment of a disease. Effective dose parameters and modes of administration can be determined using methods standard in the art for a particular transplant or disease. Such methods include, for example, determination of survival rates, side effects (i.e., toxicity) and survival of graft/progression or regression of disease. In particular, the effectiveness of dose parameters and modes of administration of a therapeutic composition of the present invention when treating a T-lymphocyte-mediated disease (discussed below) can be determined by assessing response rates. Such response rates refer to the percentage of treated patients in a population of patients that respond with either partial or complete remission of the disease. The effectiveness of dose parameters and modes of administration of a therapeutic composition of the present invention when suppressing or preventing graft/transplant rejection can be determined by assessing the survival of the graft over time.

In accordance with the present invention, a suitable single dose size is a dose that is capable of suppressing or preventing graft rejection when administered one or more times over a suitable time period. Doses can vary depending upon the disease being treated.

A suitable single dose of a recombinant viral vector encoding an apoptosis-inducing protein in a pharmaceutically acceptable carrier to administer to an animal to suppress or prevent graft rejection, is an amount capable of reducing, and preferably eliminating, destruction of the graft following transfection of the recombinant molecules into cells at or near the graft site. A preferred single dose of a therapeutic composition to treat graft rejection is from about 100 μg to about 2 milligrams (mg) of total recombinant molecules, more preferably from about 150 μg to about 1 mg of total recombinant molecules, and even more preferably from about 200 μg to about 800 μg of total recombinant molecules.

It will be obvious to one of skill in the art that the number of doses administered to an animal is dependent upon the response of an individual patient to the treatment, as well as other factors, such as whether the patient has a disease which will affect graft survival (e.g., an autoimmune disease). Thus, it is within the scope of the present invention that a suitable number of doses includes any number required to allow graft survival. A preferred protocol is monthly administrations of single doses (as described above) for up to about 1 year. A preferred number of doses of a therapeutic composition comprising pharmaceutically acceptable carrier comprising a recombinant viral vector in order to suppress graft rejection is from about 1 to about 10 administrations per patient, preferably from about 2 to about 8 administrations per patient, and even more preferably from about 3 to about 5 administrations per patient. Preferably, such administrations are given once every 2 weeks until signs of graft survival are measured, then once a month until it is determined that treatment can be decreased or eliminated.

A preferred number of doses of a pharmaceutically acceptable carrier comprising a recombinant viral vector of the present invention in order to suppress graft rejection, is from about 2 to about 10 administrations patient, more preferably from about 3 to about 8 administrations per patient, and even more preferably from about 3 to about 7 administrations per patient. Preferably, such administrations are given once every 2 weeks signs of graft survival are measured, then once a month until it is determined that treatment can be decreased or eliminated.

In one embodiment of the method to suppress T-lymphocyte mediated graft rejection, the apoptosis-inducing protein is Fas ligand. One aspect of the present invention generally relates to the use of Fas ligand to suppress T-lymphocyte-mediated immune responses, including rejection of transplanted tissue. Such a method is disclosed in related U.S. Pat. No. 5,759,536, which is incorporated herein by reference in its entirety. Such immune responses include those directed against autologous tissue in autoimmune conditions, as well as immune responses against autologous, allogeneic or xenogeneic tissue transplanted into patients in need of such tissues (e.g., transplants of porcine islet cells into patients who have or are at risk of developing diabetes mellitus). The present invention also relates to the use of Fas ligand to prevent T-lymphocyte-mediated disease recurrence and to treat T-lymphocyte-mediated primary disease (i.e., a T-lymphocyte mediated autoimmune disease). The methods of the invention involve providing an amount of Fas ligand effective to suppress T-lymphocyte-mediated rejection of transplanted tissue, disease recurrence, and/or primary disease.

Prior to the present invention, it was known that several immunologically privileged sites in mammals allow prolonged survival of transplanted allografts. The remarkable survival of islet allografts and xenografts transplanted into abdominal testes has been reported (Selawry et al, 1985, *Diabetes,* 34:1019-1024; Bellgrau et al., 1990, *Transplantation,* 50:654-657; Selawry et al., 1987, *Diabetes,* 36:1061-1067). For example, it has been shown that an unknown factor or factors released by testicular Sertoli cells appears to be responsible for the protection of the intratesticular islet allografts and xenografts against rejection (Selawry et al., 1991, *Transplantation,* 52:846-850). This unknown factor(s) has been reported to inhibit the production of IL-2 in vitro.

In addition, Sertoli cells have been used to establish an immunologically privileged site in vivo in the renal subcapsular space (Selawry et al., 1993, *Cell Transplantation,* 2:123-129). Briefly, diabetic PVG rats received rat islet cell grafts with and without Sertoli cells and with and without cyclosporine (CsA). The results showed that 70%-100% of the recipient rats receiving islet cells alone, islet cells and CsA, or islet cells and Sertoli enriched cells, remained hyperglycemic. In contrast, prolonged normoglycemia in excess of 100 days was achieved in rats receiving a combination of islet cells, Sertoli enriched cells, and CsA.

The present inventors discovered for the first time that the factor released by testicular Sertoli cells which is responsible for the protection of the intratesticular islet allografts and xenografts against rejection is the Fas ligand. It was not until the discovery of this heretofore unknown mechanism of T-lymphocyte suppression in an immunopriveleged site that the novel, site-specific, and highly effective methods for suppressing T-lymphocyte mediated graft rejection, T-lymphocyte-mediated disease recurrence, and T-lymphocyte-mediated primary disease by providing exogenous Fas ligand were appreciated.

The Fas ligand, which is the naturally occurring ligand of Fas, was recently purified and identified as a 40 kD membrane glycoprotein (Suda et al., 1993, *Cell,* 75:1169-1178). The purified Fas ligand exhibits cytolytic activity against cells expressing Fas. Prior investigators, however, failed to appreciate that Fas ligand is responsible for the absence of T-lymphocyte responses in "immunopriveleged sites", and that exogenous expression of Fas ligand by transfected cells or by delivery of Fas ligand to a cell via a viral vector is a safe and effective means of suppressing T-lymphocyte mediated graft rejection and/or treating T-lymphocyte mediated primary disease and disease recurrence. Instead, prior investigators cautioned against therapies designed to ligate Fas on cells in vivo, in view of studies which showed that administration of anti-Fas antibody in vivo to an animal was lethal (Ogasawara et al., 1993, *Nature,* 364:806-809). Similarly, other investigators suggested that soluble Fas ligand may contribute to human disease in a similar manner as the above-referenced anti-Fas antibody (Suda et al., 1993, supra).

Prior to identification of the Fas ligand, it was known that ligation of Fas on the surface of lymphocytes which were activated chronically with IL-2 in vitro (i.e., artificially and non-specifically activated) resulted in apoptosis of the cell expressing Fas (Owen-Schaub, 1992, *Cell. Immunol.,* 140: 197-205). These studies, however, failed to show that induction of apoptosis occurred in freshly isolated lymphocytes, in cultured non-activated lymphocytes, or in early activated lymphocytes, and suggested that Fas was not the sole mediator of this apoptotic cell death. Other studies added to the confusion as to whether normally activated T cells are primed for Fas-mediated killing (Klas et al., 1993, *Int. Immunol.,* 5:625-630). It was not until the present invention that it was demonstrated that ligation of Fas by its natural ligand, the Fas ligand, in vivo is sufficient to cause apoptotic death in cells bearing Fas, including normally activated T cells.

Furthermore, as discussed above, the present inventors are the first to appreciate that Fas ligand, provided exogenously (e.g., delivered and/or expressed by a viral vector), is safe and effective in vivo for suppressing T-lymphocyte-mediated graft rejection. Prior to the present invention, many proposed therapies for suppressing graft rejection involved down-regulating, eliminating or masking molecules on the surface of cells in a graft to prevent recognition of the graft by T-lymphocytes directed against the graft (See, for example, Faustman et al., 1994, U.S. Pat. No. 5,283,058). In contrast, the methods of the present invention involve purposefully expressing and/or upregulating the expression of a molecule (i.e., Fas ligand) on the surface of cells in the graft or in cells cotransplanted with the graft, in order that the Fas ligand will specifically interact with T-lymphocyte's directed against the graft.

In activation of the immune system, T-lymphocytes (i.e., T cells) are presented with a foreign antigen. A T cell response occurs when a T cell receptor (TCR) recognizes an antigenic peptide (e.g., a foreign antigen) bound to an MHC protein, thereby altering the activity of the T cell bearing the TCR. As used herein, a "T cell response" can refer to the activation, induction of anergy, or death of a T cell that occurs in response to an interaction between a molecule on the T cell with another molecule. As used herein, "activation" of a T cell refers to induction of signal transduction pathways in the T cell resulting in production of cellular products (e.g., interleukin-2) by that T cell. Activated T-lymphocytes further respond by differentiating into effector cells, and the effector cells then clear the foreign antigen. "Anergy" refers to the diminished reactivity by a T cell to an antigen. As used herein, "T cell death" refers to the permanent cessation of substantially all functions of the T cell. One type of T cell death is apoptosis.

In rejection of an allograft, the immune system of the recipient animal has not previously been primed to respond because the immune system for the most part is only primed by environmental antigens. In other words, tissues from other members of the same species have not been presented in the same way that, for example, viruses and bacteria have been presented. In the case of allograft rejection, immunosuppressive regimens are typically designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence the immune system is already at the effector stage. The Fas ligand is able to suppress the immune response to both allografts and xenografts because lymphocytes activated and differentiated into effector cells express Fas, and thereby are susceptible to the Fas ligand.

According to the present invention, the terms "graft" and "transplant" can be used interchangeably. Similarly, a graft can be transplanted into a recipient, and a transplant can be grafted into a recipient.

A reaction or disease is considered to be T-lymphocyte-mediated when T-lymphocytes are required in mediating the reaction or disease effect. Where cells of the tissue for transplantation (the "donor" tissue) bear on their surfaces foreign histocompatibility antigens, these antigens cause cytotoxic T-lymphocyte activation in recipients, terminating in donor cell destruction after several sequential activation stems. The cascade is initiated by conjugate formation between the antigen-specific T-cell receptor on host T-lymphocytes and the major histocompatibility antigens on the donor cell. Conjugate formation is followed by T-lymphocyte-mediated activation, resulting in donor cell death. This process can eventually result in rejection even in intra-species transplantation. According to the invention, this problem is addressed by suppressing the T-lymphocyte response prior to the stage where donor cell destruction is initiated.

The Fas ligand may be used to treat chronic transplant rejection. It is recognized by the art that most transplants undergo a chronic graft destructive process. The mechanism of chronic transplant rejection differs from conventional allograft immunity and conventional immunosuppression has been ineffective in its treatment. Chronic draft rejection may be treated with the Fas ligand, resulting in successful engraftment for longer periods of time and allowing donor tissue to be used for new recipients.

The Fas ligand may also be used to treat acute graft rejection. Treatment with the Fas ligand should provide a more specific treatment for activated cells, that is, for cells attacking the transplant tissue, not all the T-lymphocytes present in the immune system.

This invention addresses that need by providing methods which allow the use of non-human tissue for transplantation into a human patient in need thereof. The method of the invention prevents rejection of xenogeneic tissue. The invention thus permits not just intra-species transplantation of tissues and organs, but xenografts as well, opening up the possibility of "farming" of donor organs and tissues in non-human mammals for transplantation into human patients. In the case of xenografts, this invention may be practiced along with other methods for masking, modifying, or eliminating undesirable antigens on the surface of donor cells, such as the method described in U.S. Pat. No. 5,283,058, which is incorporated herein by reference in its entirety.

Another embodiment of the present invention relates to a method of inducing apoptosis in cells of a recipient mammal. In particular, this method is useful for inducing apoptosis in a particular cell population to be eliminated, such as cancer cells at a site of a cancer (e.g., a tumor). The method comprises introducing into the mammal a pharmaceutically acceptable carrier which comprises a recombinant viral vector comprising a nucleic acid sequence encoding an apoptosis-inducing protein. In one embodiment, the pharmaceutically acceptable carrier comprises: a) a recombinant nucleic acid molecule comprising a nucleic acid sequence encoding a protein that inhibits apoptosis; and (b) a recombinant viral vector comprising a nucleic acid sequence encoding an apoptosis-inducing protein. In this embodiment, the recombinant nucleic acid molecule of (a) is preferably contained within the recombinant viral vector, although the recombinant nucleic acid molecule can be administered as a separate molecule. When the nucleic acid sequence encoding the apoptosis-inhibiting protein is within the recombinant viral vector, the nucleic acid sequence encoding this protein and the nucleic acid sequence encoding the apoptosis-inducing protein can be operatively linked to the same or different transcription control sequences, and when linked to the same transcription control sequence, are preferably separated by an IRES.

Preferably, the recombinant viral vector is delivered to a target cell which is at or adjacent to the site of the cancer, or in one embodiment, the pharmaceutically acceptable carrier is a cell which in transfected with the recombinant viral vector and delivered to the site of the cancer. Therefore, the recombinant viral vector can be propagated in the carrier cell and released at the site of the cancer to infect cancer cells and cause apoptosis in the cancer cells, the recombinant viral vector can be expressed directly in cancer cells or cells adjacent to the cancer cells, or the recombinant viral vector can be expressed by the carrier cell and interact with cancer cells to cause apoptosis. The present inventors have found that the recombinant viral vector encoding an apoptosis-inducing protein is effective to induce apoptosis in tumor cells at the site of delivery, even though some of the tumor cells are not infected with the vector. The presence of the apoptosis-inhibiting protein in the vector may protect a carrier cell in some embodiments, and in other embodiments, such protein may attenuate the apoptotic response so that apoptosis is controlled and limited to tumor cells. This method of the present invention can be used to treat any cancer, and cancers into which the recombinant viral vector is easily introduced are particularly preferred. Such cancers include, but are not limited to, prostate cancer, lung cancer, brain cancer, lymphoma (e.g., Sezary Syndrome, mycosis fungoides, T cell lymphoma), leukemia, and metastatic cancers which reside in these tissues (e.g., a liver cancer that has metastasized to the lung).

In this embodiment of the present invention, the preferred recombinant viral vectors are derived from any of the viral vectors disclosed previously herein. In the case of lymphomas and leukemias, the recombinant viral vector is preferably from a lentivirus. In this embodiment, the vectors are preferably administered systemically. In other types of cancer, preferred routes of administration are those routes which most directly deliver the recombinant viral vector to the site of cancer with limited exposure to other tissues. For example, a recombinant viral vector of the present invention is preferably delivered to lung cancers by aerosol or intratracheal delivery, and the vector is preferably delivered to brain cancers by direct injection into the tumor.

Yet another embodiment of the present invention relates to methods for suppressing a T-lymphocyte-mediated disease in a recipient mammal. This method includes introducing (i.e., administering) into a mammal a pharmaceutically acceptable carrier comprising a recombinant viral vector comprising a nucleic acid sequence encoding a protein that induces apoptosis operatively linked to a transcription control sequence. In one embodiment of this method, the pharmaceutically acceptable carrier can additionally comprise a recombinant nucleic acid molecule comprising a nucleic acid sequence encoding a protein that inhibits apoptosis operatively linked to a transcription control sequence. In this embodiment, the nucleic acid sequence encoding the apoptosis-inhibiting protein is preferably contained within the recombinant viral vector, although the recombinant nucleic acid molecule can be administered as a separate molecule, particularly when delivered to a cell by ex vivo methods. When the nucleic acid sequence encoding the apoptosis-inhibiting protein is within the recombinant viral vector, the nucleic acid sequence encoding this protein and the nucleic acid sequence encoding the apoptosis-inducing protein can be operatively linked to the same or different transcription control sequences, and when linked to the same transcription control sequence, are preferably separated by an IRES. Such vectors, recombinant molecules, apoptosis-inducing proteins and apoptosis-inhibiting proteins have been described above. When a recombinant nucleic acid molecule encoding an apoptosis-inhibiting protein is included, the method has the advantage of protecting a cell which expresses the apoptosis-inducing protein from elimination itself. In a preferred embodiment, the apoptosis-inducing protein is Fas ligand. For example, lymphocytes activated by disease as well as by the introduction of foreign grafts express Fas, and therefore, are susceptible to treatment with Fas ligand. In general terms, the Fas ligand as an immunosuppressive agent is most active against a primed or activated immune system. The primed or activated immune system may he associated with disease conditions in which either T-lymphocytes or B-lymphocytes are activated. Activated T-lymphocytes are associated with disease in graft versus host reactions (e.g., bone marrow transplantation) and most forms of autoimmunity, including but not restricted to, multiple sclerosis, rheumatoid arthritis, lupus, and myasthenia gravis. Fas expressing leukemia may also be susceptible to treatment with the Fas ligand, since Fas is expressed by B- and T-lymphocyte tumors.

In order to treat an animal with a T-lymphocyte-mediated disease, a pharmaceutically acceptable carrier of the present invention is administered to the animal in an effective manner such that the composition is capable of treating that disease. For example, a recombinant viral vector of the present invention, when administered to an animal in an effective manner, is able to suppress effector cell immunity in a manner that is sufficient to alleviate the disease afflicting the animal. According to the present invention, treatment of a disease refers to alleviating a disease and/or preventing the development of a secondary disease (e.g., recurring disease) resulting from the occurrence of a primary disease.

Such a therapeutic composition of the present invention is particularly useful for the treatment of autoimmune diseases, including but not limited to, insulin dependent diabetes mellitus, multiple sclerosis, systemic lupus erythematosus, myasthenia gravis, rheumatoid arthritis, psoriasis, polyarteritis, immune mediated vasculitides, immune mediated glomerulonephritis, inflammatory neuropathies and sarcoidosis.

A single dose of recombinant viral vector to administer to an animal to treat an autoimmune disease is from about 0.1 μg to about 200 μg of total recombinant molecules per kilogram (kg) of body weight, more preferably from about 0.5 μg to about 150 μg of total recombinant molecules per kg of body weight, and even more preferably from about 1 μg to about 10 μg of total recombinant molecules per kg of body weight. The number of doses of the recombinant viral vector to be administered to an animal to treat an autoimmune disease is an injection about once every 6 months, more preferably about once every 3 months, and even more preferably about once a month.

A pharmaceutically acceptable carrier of the present invention can be administered to treat an autoimmune disease by any method and dose previously disclosed herein for administration of a viral vector and/or pharmaceutically acceptable carrier of the present invention. In one embodiment, the pharmaceutically acceptable carrier is administered by local administration, preferably direct injection at the site of the autoimmune response. Although the pharmaceutically acceptable carrier and viral vector can be designed to have prolonged expression (e.g., weeks to months) at the site of treatment, prolonged expression is not required to have a therapeutic effect and in some instances, short-term expression is preferred. Other preferred routes and protocols of administration have been previously described in detail herein.

The invention may be used to treat a number of human disease conditions resulting from destruction of endogenous cells, such as the destruction of insulin producing pancreatic islet beta cells in diabetes. An important feature of the invention is that it makes possible the use of non-human mammals as tissue and organ donors for human patients. The above methods describe the use of the invention to treat diabetic human patients by transplantation of xenogeneic islet cells. The xenogeneic islet cells may be obtained for example, normal or transgenic pigs expressing the Fas ligand protein. Example 4 describes transplantation of transgenic porcine islet cells into a diabetic human patient.

Transgenic Animals

Preferably, a transgenic non-human animal of the present invention is a mammal including, but not limited to, farmed mammals, primates and rodents. In one embodiment, a preferred transgenic non-human animal of the present invention is a rodent, and even more preferably, a rat or a mouse. In another embodiment, a preferred transgenic non-human animal is a mammal which can be used to provide donor organs and/or tissues to a human patient, including, but not limited to, primates and pigs.

According to the present invention, a transgenic non-human animal is a non-human animal which includes a recombinant nucleic acid molecule (i.e., transgene) that has been introduced into the genome of the non-human animal at the embryonic stage of the non-human animal's development. As such, the transgene will be present in all of the germ cells and somatic cells of the non-human animal. Methods for the introduction of a transgene into a mouse embryo, for example, are known in the art and are described in detail in Hogan et al., "Manipulating the Mouse Embryo. A Laboratory Manual", Cold Spring Harbor press, Cold Spring Harbor, N.Y., 1986, which is incorporated by reference herein in its entirety. For example, a recombinant nucleic acid molecule (i.e., transgene) can be injected into the male pronucleus of a fertilized mouse egg to cause one or more copies of the recombinant nucleic acid molecule to be retained in the cells of the developing mouse. A mouse retaining the transgene, also called a "founder" mouse, usually transmits the transgene through the germ line to the next generation of mice, establishing transgenic lines. According to the present invention, a transgenic mouse also includes all progeny of a transgenic mouse that inherit the transgene.

Transgene sequences can be cloned using a standard prokaryotic cloning system, and the transgene products can excised from the prokaryotic vector, purified, and injected into the pronuclei of fertilized eggs from the desired transgenic animal. Stable integration of the transgene into the genome of the transgenic embryos allows permanent transgenic animal lines to be established.

The method of the invention may also be used to prevent a recurring disease which resulted in destruction of endogenous tissue. For example, disease recurrence mediated by T-lymphocytes directed to islet β cell antigens results in destruction of grafted islet cells. Therefore, providing Fas ligand to the graft site prevents recurrence of diabetes and allows normoglycemia to be achieved in recipient mammals by suppressing the. immune response directed to islet β cell antigens.

The following examples are provided for the purposes of illustration and are not intended to limit the scope of the present invention.

EXAMPLES

Example 1

The following examples demonstrates suppression of T-lymphocyte-mediated rejection of transplanted tissue by administration of Fas ligand.

Islet Preparation. Freshly isolated islet cells from a rat are prepared according to known methods. See, for example, London et al. (1990) Transplantation 49:11091113. Under appropriate circumstances, islet cells may be pretreated prior to transplantation to conceal (,"mask") donor antigens or modify graft immunogenicity by methods known in the art, for example, those described in U.S. Pat. No. 5,283,058, Purified Fas Ligand. Purified Fas ligand may be obtained from a mammalian source or produced in vitro as a recombinant protein. In one embodiment of the invention, purified Fas ligand is obtained from a naturally occurring source. A simple method for large scale purification of Fas ligand from cultured cells has been reported (Suda & Nagata (1994) supra) . Briefly, cells expressing Fas ligand are cultured and harvested. A solubilized membrane fraction is purified by affinity purification, and the Fas ligand eluted as described by Suda & Nagata (1994), supra.

In another embodiment, Fas ligand is produced by recombinant DNA methods, utilizing the genes coding for Fas ligand. Expression of a recombinant rat Fas ligand has been obtained (Suda et al. (1993) Cell 75:IIG9-1178). The amino acid sequences of many proteins are highly conserved across a variety of mammalian species. As a consequence of the conservation of the nucleotide sequences there is considerable conservation of the nucleotide sequences of the genes that encode these proteins. Therefore, it is generally true that the gene encoding the Fas ligand in one mammalian species can cross-hybridize (i.e. form a stable double-stranded DNA hybrid) with the genes encoding that factor in other mammalian species under appropriate annealing conditions. This property may he used to identify cloned human DNA segments that include the gene for Fas ligand. For example, the human gene encoding the Fas ligand may be identified by screening a human genomic library using a $^{32}$P-labeled probe derived from the rat cDNA sequence of the Fas ligand (Suda et al. (1993) supra. Suitable host cells transformed with a vector containing DNA encoding the human Fas ligand are cultured under conditions for amplification of the vector and expression of the Fas ligand, and Fas ligand is harvested.

Bioassay of Fas Ligand. The biological activity of purified Fas ligand is assessed in vitro with the, cytotoxicity assay described by Suda & Nagata (1994) supra.

Transplantation of Rats and Administration of Purified Fas Ligand. Diabetic PVG rats are grafted with islet cells and implanted with pumps dispensing saline (controls) or purified Fas ligand (experimental) as follows. Diabetic PVG rats are anesthetized with methoxyflurane USP and the left flank opened to expose the kidney. Islets cells (10 islets/g of body weight) are injected under a renal capsule as described by Selawry & Cameron (1993) supra. A pump programmed to dispense either saline or purified Fas ligand over an empirically-determined period of time is implanted under the renal capsule. Cyclosporine (CsA) may be injected subcutaneously 25 mg/kg per day for a seven day period.

Recipient rats are evaluated for plasma glucose levels. Urine volumes and urine glucose contents are obtained and determined as described (Selawry & Cameron (1993) supra. Recipient rats receiving Fas ligand become normoglycemic over a prolonged period of time.

Example 2

The following example demonstrates production of transgenic mammals containing DNA encoding the Fas ligand.

A transgenic rat whose germ cells and somatic cells contain the Fas ligand gene is produced by methods known in the art. See, for example, U.S. Pat. No. 4,736,866 describing production of a transgenic mammal, herein incorporated by reference. Generally, the DNA sequence encoding the Fas ligand is introduced into the animal, or an ancestor of the animal, at an embryonic stage (preferably at the one-cell, or fertilized oocyte, stage, and generally not later than about the 8-cell stage). There are several methods known to the art of introducing a foreign gene into an animal embryo to achieve stable expression of the foreign gene. One method is to transfect the embryo with the gene as it occurs naturally, and select transgenic animals in which the foreign gene has integrated into the chromosome at a locus which results in its expression. Other methods involve modifying the foreign gene or its control sequences prior to introduction into the embryo. For example, the Fas ligand gene may be modified with an enhanced, inducible, or tissue-specific promoter.

Tissues of transgenic rats are analyzed for the presence of Fas ligand, either by directly analyzing RNA, by assaying the tissue for Fas ligand, or by assaying conditioned medium for the secreted Fas ligand. For example, cells obtained from the transgenic rat are cultured in the presence of $^{35}$S-methionine, the supernatant subjected to immunoprecipitation with antibodies to Fas ligand. Precipitated proteins are resolved by reducing SDS-polyacrylamide gel electrophoresis, and visualized by autoradiography. Conditioned medium may also be tested for in vitro cytotoxic activity by the method of Suda & Nagata (1994), supra, or by performing chromium release assays as described in Example 10.

Example 3

The following example shows transplantation of transgenic islet cells expressing the Fas ligand.

Islet cells are obtained from the transgenic rat of Example 2 and grafted into diabetic PVG rats by the methods described in Example 1. Recipient rats, evaluated as described above, achieve normoglycemia for prolonged periods of time.

Example 4

The following example demonstrates the transplantation of transgenic porcine islet cells into a human diabetic patient.

A transgenic pig is obtained all of whose germ cells and somatic cells contain a recombinant DNA sequence encoding human Fas ligand. The human Fas ligand DNA sequence was introduced into the pig by methods known to the art. Islet cells are obtained from the transgenic pig by the methods described in Example 2 and are grafted into diabetic human patient by methods known in the art. The human patient, evaluated appropriately, achieves normoglycemia for prolonged periods of time.

Example 5

The following example demonstrates production of Fas ligand mRNA by isolated Sertoli cells.

cDNA synthesis. Total RNA from purified rat Sertoli cells was isolated from cell pellets by the method of Chomczynski and Sacchi (1987) Anal. Biochem. 162:156. The RNA (5 μg) was first denatured in methyl mercuric hydroxide (10 mM final concentration) (Alfa Products, Ward Hill, Mass.) and converted to cDNA in Taq (*Thermus aquaticus*) DNA polymerase buffer (50 mM KCl, 10 mM Tris-HCl, pH 8.3, 2.5 mM $MgCl_2$ and 0.01% gelatin) in the presence of RNA guard (20 units) (Pharmacia, Piscataway, N.J.), β-mercaptoethanol (40 mM), dNTPs (0.5 mM) (Pharmacia), 1 μg random hexamers (Pharmacia) and AMV (Avian myeloblastosis virus) reverse transcriptase (20 units) (Life Sciences Inc., St. Petersburg, Fla.) in a 50 μl reaction for 90 min at 42° C.

PCR Amplification. Following synthesis, 5 μl of the cDNA was transferred to a tube on ice containing 200 mM dNTPs (Pharmacia), Taq polymerase buffer containing 1.5 mM $MgCl_2$, Taq DNA polymerase (1 unit) (Perkin Elmer Cetus, Norwalk, Conn.) and the rat Fas ligand specific oligonucleotide primers 5'-GCCCGTGAATTACCCATGTC-3' (SEQ ID NO:1) and 5'-TGGTCAGCAACGGTAAGATT-3' (SEQ ID NO:2) (forward and reverse, respectively) . The samples were overlaid with light mineral oil (Sigma Chemical Corp., St. Louis, Mo.) and transferred to a thermal cycler (MJ Research, Inc., Watertown, Mass.). Following heating to 94° C. for 5 min to denature DNA/RNA complexes, the samples were amplified for 28 cycles of 1 min at 94° C., 1.5 min at 55° C., and 2 min at 72° C., followed by a final 10 min extension at 72° C.

Detection. 20 μl of the starting 50 μl reaction was separated by electrophoresis through a 1.6% agarose gel. The following samples were run: mRNA from Sertoli cells incubated at 32° C. (lane 1) or at 37° C. (lane 3); mRNA from Sertoli cells from a second animal incubated at 32° C. (lane 2) or at 37° C. (lane 4). The DNA in the gel was then transferred to nitrocellulose filters (Schleicher & Schuell, Keene, N.H.) according to the method of Southern (1975) J. Mol. Biol. 98:503. The filters were UV cross linked (Stratagene, San Diego, Calif.) and hybridized at 37° C. overnight in a solution containing 6×SSC (1×SSC=0.15 M sodium chloride and 0.015 M sodium citrate), 1×Denhardts (0.02% each Ficoll 400, bovine serum albumin, and polyvinylpyrrolidone), 20 μg/ml wheat germ tRNA, 0.1% SDS and 0.05% sodium pyrophosphate plus the $^{32}$p end-labeled Fas ligand specific oligonucleotide 5'-AACATAGAGCTGTGGCACC-3' (SEQ ID NO:3). After extensive washing in 6×SSC plus 0.05% sodium pyrophosphate at 47° C., the filters were dried and exposed to Kodak X-Omat film.

An autoradiograph of the amplified rat Sertoli cell mRNA was obtained. Lanes 1 and 3 are mRNA from cells incubated at 32° C. or 37° C., respectively; lanes 2 and 4 are mRNA from Sertoli cells taken from a second animal cultured at 32° C. or 37° C., respectively. These results show that Sertoli cells are the dominant, if not exclusive, source of Fas ligand in the testis.

DNA Sequencing. The PCR product was determined to be identical to that published by Suda et al. (1993) Cell 75:1169 by standard DNA sequencing methodology of Sanger et al. (1977) Proc. Natl. Acad. Sci. USA 78:5453.

Example 6

The following example demonstrates the effect of Fas ligand on grafted testicular survival.

To test whether the absence of a functional Fas ligand molecule prohibited Sertoli cells from providing their immunosuppressive function, the present inventors transplanted testicular tissue from male B6-Gld or genetically compatible but Fas ligand operative C57BL/6 (B6) mice into BALB/c recipients. The B6-Gld and B6 strains are identical at the major histocompatibility complex (MHC) and also share essentially all other (minor) histocompatibility antigens with the exception of the Fas ligand. B6-Gld carries a point mutation in the Fas ligand gene (Takahashi et al. (1994) Cell 7:969). B6-Gld and B6 differ from the BALB/c strain at both the MHC and multiple minor loci.

Testicular drafts of B6-Gld or B6 tissue were transplanted under the kidney capsule of BALB/c recipients. A mouse is weighed and injected with Avertin (12 ml/g), and anesthetized with Metophane. The mouse is shaved under the rib cage on the left side, and a small incision (about 8 mm) is made through the body wall. The adipose tissue attached to the posterior end of the kidney is pulled such that the kidney is externalized. The kidney is kept moist with Hank's Basic Salt Solution (HBSS). A straight incision is made on the posterior end of the kidney and the kidney capsule carefully loosened from the kidney with a probe. The tissue to be transplanted is deposited under the capsule and gently moved to the anterior part of the kidney with a probe. The kidney is replaced inside the body and the incision closed.

Blood Clot Transplantation Procedure. This procedure is designed to permit groups of cells or non-clustered islets to be transplanted under the recipient host kidney capsule. Embedding the cells within the clot allows the transplanter to place them in a relatively defined position from which they will not move.

Cells to be transplanted are transferred to a siliconized 15 ml centrifuge tube and allowed to settle for 5 min. Cells in a cell suspension are transferred to a siliconized 15 ml centrifuge tube and centrifuged at 300 ×g for 5 min. Most of the supernatant is removed and the cells resuspended in the remaining 200 μl medium. The cells are resuspended and transferred to a 300 μl microfuge tube, centrifuged at 500- 1.000 ×g for 30 sec and placed on ice. Most of the supernatant is removed, leaving about 4-5 mm fluid.

With a scalpel, the top is cut just above the fluid level, and the remaining fluid removed with a capillary tube. Blood is drawn from the tail vein of the recipient animal and approximately 5 μl blood added to the cell pellet. A clot is allowed to form for 10 min. Residual sera is drawn off. The cells are embedded within the clot matrix and are not easily dislodged. The cell clot may then be transplanted into the kidney capsule.

Results. On days 2 and 7 (B6-Gld) or days 2, 7, and 28 (B6), the grafted tissue was analyzed macroscopically and microscopically for graft rejection. A recipient BALB/c mouse was euthanized with an overdose of penthrane. The kidney containing the graft was removed, fixed in a formal saline buffer solution and processed by routine histologic techniques. The kidney was embedded in paraffin after which 5 μl sections were cut and stained with hematoxylin and eosin. Renal tissue obtained from BALB/c kidney engrafted with B6 tissue appeared structurally normal by light microscopy. Transplanted tissue was observed adjacent to the kidney capsule. It appeared no different in morphology from that which was observed when histocompatible-genetically identical BALB/c tissue was used as the source of donor tissue. In B6-Gld engrafted kidney there was extensive infiltration of lymphocytes in the graft by day 2, and the architecture of the testis tissue was disrupted. The renal tissue also showed obvious lymphocytic infiltration adjacent to as well as within the craft. By day 7, there was little recognizable testis tissue and infiltrate was diminished, indicating that the destructive process had peaked before this time. These findings establish the role of the Fas ligand in immunosuppression, and show that the absence of a functional Fas ligand gene protects transplanted testicular tissue from graft rejection.

Example 7

The following example demonstrates the effect of Fas ligand on Sertoli cell immunosuppressive activity.

To establish if isolated Sertoli cells could duplicate the results obtained with testis tissue grafts (Example 6), Sertoli cells were isolated and purified from testicular tissue of B6-Gld and B6 mice and transplanted as single cell suspensions under the kidney capsule in BALB/c mice, essentially as described by Selawry and Cameron (1993) Cell Transplantation 2:123 and Example 6 above. Testis were removed from mice and cut into small pieces in 5 ml HAM's F12/DMEM media (Ham's media). The tissue was placed in a 50 ml tube, 25 ml Ham's media added, and pelleted by centrifugation at 800×g for 2-5 min. The pellet was resuspended in 20 ml Ham's media containing 20 mg trypsin and 0.4 mg DNAse. The resulting mixture was placed in a 250 ml flask in a shaking water bath at 37° C. for 30 min, and pelleted at 800×g for 2-5 min. The cell pellet was resuspended at room temperature for 10 min in 20 ml of a solution containing 1 M glycine, 2 mM EDTA, 0.01% soy bean trypsin inhibitor, and 0.4 mg DNAse. The mixture was centrifuged as above, and the cell pellet washed twice. Cells were resuspended in 20 ml Ham's media containing 10 mg collagenase, and placed in a shaking water bath at 37° C. for 5 minutes, pelleted, and resuspended in 20 ml Ham's media containing 20 mg collagenase and 0.1 mg DNAse. The sample was transferred to a 250 ml flask placed in a rocking water bath at 37° C. for 30 min. The cells were pelleted and washed as described above. Cells were resuspended in 10 ml Ham's media containing 20 mg hyaluronidase and 0.1 mg DNAse, and placed in 250 ml flask in a rocking water bath at 37° C. for 30 min. Cells were pelleted and washed. The final pellet was kept on ice until transplanted under the kidney capsule. The pellet may be clotted with blood drawn from the host mouse (see blood clot transplantation procedure described above).

Results identical to those described in Example 6 were obtained. B6-Gld Sertoli cells transplanted under the kidney capsule of histoincompatible BALB/c recipient mice remained intact. These results establish that the Fas ligand is an effective immunosuppressive factor responsible for the immunosuppressive effects of Sertoli cells.

Example 8

The following example demonstrates the diagnostic use of Fas ligand expression for selecting donor tissue or recipient transplantation site.

The discovery of the relationship between a functioning Fas ligand gene and protection from graft rejection may be applied diagnostically. The ability of various non-lymphoid tissue sources to express Fas ligand, detected either by examination of tissue with monoclonal antibodies to Fas ligand or by assessing Fas ligand mRNA by RT-PCR, allows prediction of the capacity for a specific tissue to be retained or rejected following transplantation. Tissues expressing a high level of Fas ligand provide a preferred site for successful organ engraftment. Screening donor tissue for Fas ligand expression will also aid in predicting transplantation success.

Example 9

The following example demonstrates that prostate cancer (PC) cell lines. show enhanced sensitivity to hFasL versus agonistic antibody.

Nontransfected cell cultures: The human PC cell lines, LNCaP, ALVA-31, TSU-Pr1, JCA-1, PPC-1, PC-3 and DU 145 were obtained and maintained as described previously (Hedlund et al., 1998, *Prostate* 36:92-101). K562, a human erythroid leukemia cell line was purchased from the American Type Culture Collection (Rockville, Md., USA) and were maintained in RPMI 1640 (Gibco, Grand Island, N.Y., USA) supplemented with 7.5% heat-inactivated FBS (Hyclone, Logan Utah, USA) and 2 mM L-glutamine (Gibco) at 37° C. in 95% air and 5% $CO_2$.

Stably transfected cell lines: (1) K582-hFasL and K562-neo: human K562 chronic myelogenous leukemia cells were transfected with plasmids encoding human FasL and neomycin phosphotransferase (K562-hFasL) or with a plasmid encoding neomycin phosphotransferase alone (K562-neo) as described elsewhere. (2) L1210-Fas: this transfected mouse lymphocytic leukemia cell line expresses high levels of mouse Fas and was kindly provided by Dr. P. Golstein (Marseilles, France). All transfected cell lines were routinely cultured in the presence of 600 μg/ml active Geneticin, using the medium and conditions described for nontransfected cells.

Figure 1B:
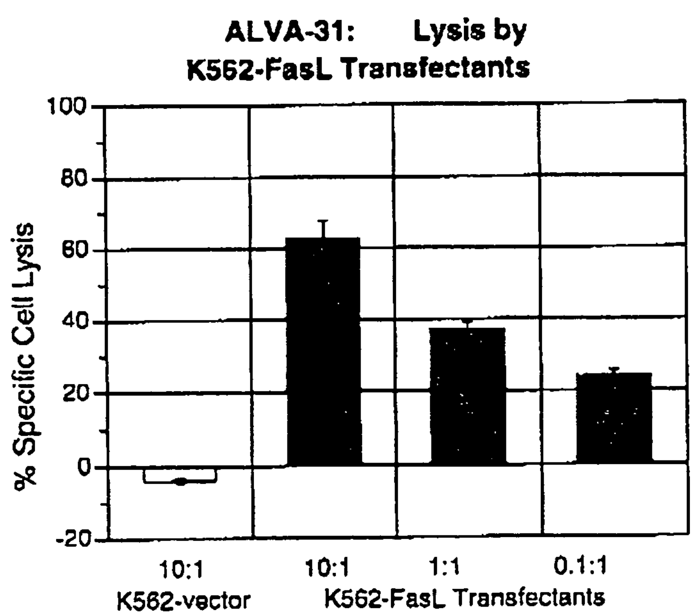
FIG. 1B is a bar graph illustrating that K562-hFasL induces lysis of PC cell line ALVA-31 in a dose-dependent fashion.

In this experiment, prostate cancer cells were labeled with $^{51}$Cr and were co-incubated for 18 h at various effector-to-target ratios with either K562-hFasL or K582-neo. Each of seven PC targets listed in Table 1 below was tested simultaneously in cytotoxicity assays to allow for direct comparison of their apoptotic potentials. L 1210-Fas cells served as positive controls since they are highly sensitive to Fas crosslinking. As shown in FIG. 1A, K562-10 hFasL induced lysis of L1210-Fas in a dose dependent fashion, whereas no specific lysis was detected when K562 cells transfected with neomycin phosphotransferase alone were used as effectors. When used as a target, the PC cell line ALVA-31 behaved similarly (FIG. 1B), with cell lysis reaching 63% at an effector to target (E:T) ratio of 10:1. A summary of the results with all eight target cell lines is presented in Table 1. The cell lines are listed in order of descending apoptotic potentials as observed in the cytotoxicity assay. Also presented in Table 1, are the results from previous studies using an agonistic mouse IgM anti-hFas antibody. These results demonstrate a markedly enhanced activity of membrane-expressed hFasL versus agonistic anti-Fas antibody.

TABLE 1

Specific lysis of human prostate cancer cell lines by K562-FasL transfectants at a 10:1 effector to target ratio. A comparison with cell lysis achieved using an anti-Fas IgM antibody in previous studies.

| Target Cell line | % Lysis by K562-FasL (±S.D.) | % Lysis by anti-Fas IgM antibody |
|---|---|---|
| L1210-Fas | 60 ± 10 | (not determined) |
| ALVA-31 | 63 ± 5 | 28% |
| TSU-Pr1 | 52 ± 13 | undetectable |
| PPC-1 | 48 ± 1 | 10% |
| JCA-1* | 47 ± 6 | 10% |
| LNCaP | 27 ± 3 | undetectable |
| DU 145* | 21 ± 2 | undetectable |
| PC-3 | 19 ± 5 | undetectable |

*JCA-1 and DU 145 showed slight but statistically significant lysis by the vector-transfected K562 clone (14 ± 1, and 4 ± 0.2%, respectively)

An interesting feature of the prostate is that it is believed to escape immune surveillance to some extent because it lacks afferent lymphatics and because of the immunosuppressive properties of seminal fluid. In fact, the normal prostatic epithelium has been found to co-express Fas and FasL, as indicated by studies with both mouse and human prostatic tissue. Therefore, the present inventors considered that it may be more relevant to test the sensitivities of the PC cell lines to internally expressed FasL through transgene methods of gene expression, rather than to FasL-expressing effector cells. Given that FasL expression was expected to induce apoptosis, the present inventors chose to develop an adenoviral system of gene transduction rather than to establish stably transfected cell lines or to rely on the limited efficiency of transient transfection methods. Adenovirus entry has been shown to be highly efficient in cells that express the integrin family of adhesion molecules and this is a common feature of many PC cell lines.

Example 10

The following example shows the construction of recombinant adenovirus encoding FasL and its propagation in 293-crmA cells.

cDNA encoding mFasL was inserted into the El region of a replication deficient human adenovirus 5 construct under the control of the CMV immediate early promoter to produce Ad5dl327CMV-mFasL (Ad-mFasL; comprising portions of SEQ ID NO:4). In brief, mouse FasL cDNA, the sequence of which is represented herein by SEQ ID NO:11, was generated by RT-PCR (Bellgrau et-al., 1995, *Nature* 377:630-632) and was inserted in the sense orientation into the pACCMV plasmid encoding the left end of the Ad5 chromosome (Gomez-Foix, et al., 1992, *J. Biol. Chem.* 267:25129-25134), but in which the CMV immediate early promoter replaces the E1 region.

The cell line 293, a human embryonic kidney cell line transformed by the E1 region of the adenovirus 5 chromosome, was purchased from the American Type Culture Collection (ATCC CRL-1573; Rockville, Md., USA) and was maintained in RPMI 1640 (Gibco, Grand Island, N.Y., USA) supplemented with 7.5% heat-inactivated FBS (Hyclone, Logan Utah, USA) and 2 mM L-glutamine (Gibco) at 37° C. in 95% air and 5% $CO_2$.

Figure 2A:
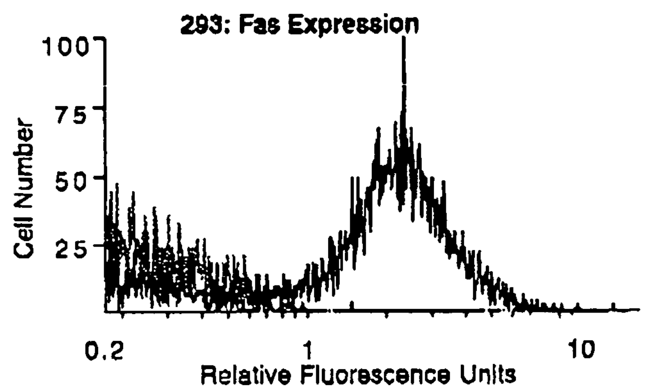
FIG. 2A is a graph showing Fas expression by 293 cells.

Initial attempts to propagate the virus in the 293 cell line resulted in early death of the cells before significant viral titers could be obtained (data not shown). Greatly reduced viral titers were also reported by Muruve et al. in a similar attempt. The present inventors suspected that 293 cells may be undergoing apoptosis before significant viral replication occurred. To test this hypothesis, 293 cells were analyzed for Fas expression by flow cytometric immunofluorescence (FIG. 2A). Briefly, cell monolayers were harvested at 50-60% confluency using the trypsin-free chelating solution described below for $^{51}$Cr-release experiments. The cells were washed once with PBS, pH 7.4, and once with the blocking solution (PBS with 5% goat serum and 0.1% sodium azide). $5\times10^5$ cells were placed in 1.5 ml microcentrifuge tubes, pelleted and resuspended in 200 μl Of blocking solution containing either 2 μg/ml FITC-conjugated mouse IgG1 anti-human Fas receptor (clone DX2, Pharmingen, San Diego, Calif., USA), or 2 μg/ml FITC-conjugated isotype control (clone DAK-G01, Dako Laboratories, Carpenteria, Calif., USA). Samples were gently mixed and incubated at room temperature for 15 min, protected from light. Cells were washed once with PBS, fixed with 1% formaldehyde in PBS for 5 min, washed again with PBS and resuspended in 0.5 ml PBS for fluorescence analysis (University of Colorado Cancer Center Flow Cytometry Core, UCHSC). The mean Fas fluorescence was 4.9-fold greater than nonspecific fluorescence. This value is relatively high compared to other cell lines that the present inventors have tested using the same method, and is similar to the level of Fas expressed by CEM cells.

Figure 2B:
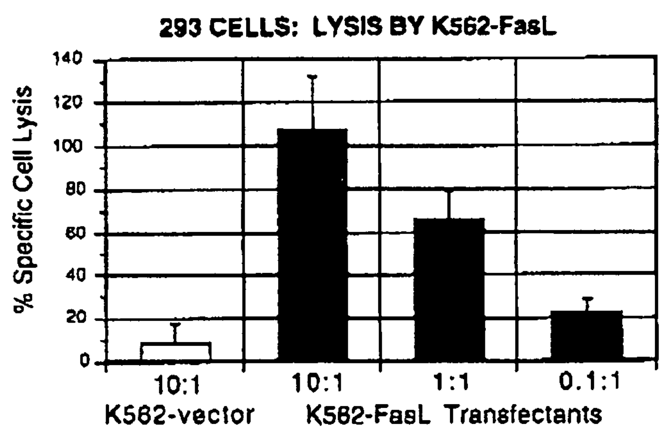
FIG. 2B is a bar graph showing that 293 cells are extraordinarily sensitive to the lytic effects of K562-hFasL.

Subsequent cytotoxicity experiments indicated that 293 cells are extraordinarily sensitive to the lytic effects of K562-hFasL (FIG. 2B), with complete lysis occurring at an E:T ratio of 10:1. Briefly, a standard chromium release assay was modified as follows. PC cell lines were removed from culture flasks by incubating at 37° C. in a trypsin-free chelating solution (135 mM NaCl, 5 mM KCl, 20 mM HEPES, and 1.5 mM EDTA, pH 7.4). For each target cell line, $10^6$ cells were pelleted and resuspended in 1 ml RPMI 1640 supplemented with 7.5% FBS and 10 mM HEPES buffer. Cells were labeled with 100 μCi$^{51}$Cr as sodium chromate (ICN Pharmaceuticals Inc., Irvine, Calif., USA) in this medium for 1 h at 37° C. Unincorporated $^{51}$Cr was removed by washing twice in 10 ml medium, incubating for 1 h in fresh medium at 37° C., and washing again. Five thousand radiolabeled target cells in 100 μl were placed in each well of a round-bottomed 96-well tissue culture plate. Effector cells (K562-hFasL or K562-neo) were added at 10:1, 1:1, or 0.1:1 ratios to the target cells, also in a volume of 100 μl per well. The plates were incubated for 16-20 h at 37° C. after which the cells were pelleted by centrifugation and 100 μl of cell-free supernatant were transferred to separate tubes for quantification of radioactivity using a gamma counter. Percent specific lysis was calculated using the following formula: (e-s/m-s)×100, where e, s and m equal the amount of radioactivity released from PC cells incubated with effector cells (experimental lysis), with 100 μl 1% Triton X-100 (maximum lysis), respectively. Results in FIG. 2B are presented as the mean±S.D. for triplicate samples.

Together, these data indicate that 293 cells were undergoing FasL-mediated apoptosis during the present inventors' attempts to produce Ad-mFasL virus. To overcome this problem, 293 cells were stably transfected with a plasmid encoding the cowpox virus caspase inhibitor crmA (SEQ ID NO:6) which inhibits FasL and TNF-mediated apoptosis. A modified calcium phosphate precipitation technique was used to transfect 293 cells with a pcDNA3-crmA construct generously provided by Dr. Tewari (University of Michigan, Ann Arbor, Mich.). Stable transfectants, resistant to agonistic anti-Fas antibody-mediated apoptosis, were selected with Geneticin (Gibco) and pooled.

Recombinant virus was generated by transfecting 293-crmA cells with a mixture of pACCMV-mFasL and Ad5dl327 $_{Bst}$β-gal DNA-Terminal protein complex prepared from purified virions and digested with Bst-B1 which cleaves uniquely 3' of the LacZ coding sequence. Briefly, Ad5dl327$^{Bst}$β-gal-TP complex was prepared by banding purified Ad5dl327$_{Bst}$β-gal virions in 4 M guanidine-HCl (Sigma Chemical Company, St. Louis, Mo.), 2.8 M cesium chloride (Baxter, McGraw Park, Ill.). The gradient was fractionated and fractions containing Ad5dl327$_{Bst}$β-gal-TP complex were collected and dialyzed against $H_2O$. The DNA-TP complex was then digested with BstBI (New England Biolabs, Beverly, Mass.), which cleaves uniquely 3' of the LacZ coding sequence (Schaack et al., 1995, *J Virol* 6:3920-3923). The pACCMV-mFasL DNA was then mixed with BstBI-digested Ad5dl327$^{Bst}$β-gal-TP complex and was used to transfect 293-crmA cells using $Ca_3(PO_4)_2$ precipitation (Jordan et al., 1996, *Nucl. Acids Res.* 24:596-601). After 5 hr, the precipitate was removed and fresh medium was added. The transfected cells were incubated until the development of a strong cytopathic effect and freeze-thawed to release virus.

Dilutions of the cell lysate were used to infect 293-crmA cells, which were then overlaid with medium containing Noble agar (Difco, Detroit, Mich., USA). After plaques developed, the cells were stained with neutral red (Baxter) and X-gal (Beohringer Mannheim, Indianapolis, Ind., USA). Plaques that were clear in the presence of X-gal, and thus likely to be recombinants, were picked and grown in 293-crmA cells. Lysates of the plaque-infected cells were used to infect 293-crmA cells. Viral DNAs were isolated and restriction analysis used to select recombinant viruses encoding mFasL. Recombinant adenovirus encoding human FasL (the nucleic acid sequence encoding human Fas ligand is represented by SEQ ID NO:7)(the adenoviral vector construct is Ad-hFasL: SEQ ID NO:4) was generated using a similar strategy.

Figure 2C:
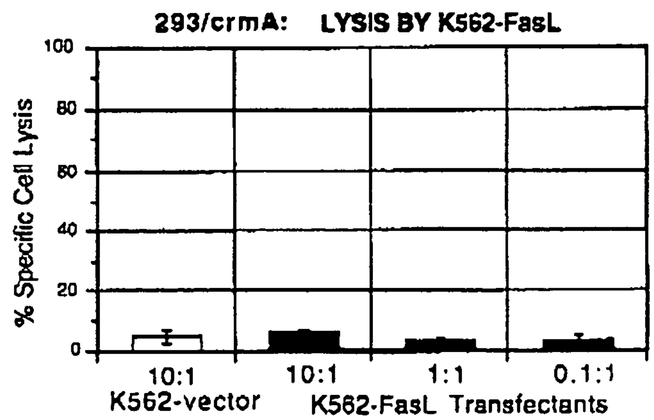
FIG. 2C is a bar graph showing that 293-crmA transfectants are almost entirely resistant to K562-hFasL.

As shown in FIG. 2C, the resulting 293-crmA transfectants were almost entirely resistant to K562-hFasL allowing to effectively propagate adenoviruses encoding mouse and human FasL, yielding viral titers of at least $5\times10^8$ pfu/ml.

Example 11

The following example demonstrates the efficiency of adenovirus gene transduction in prostate cancer (PC) cells.

To be sure that adenovirus-mediated gene expression could be achieved efficiently in the PC cells, each cell line was transduced with 100 p.f.u./cell Ad-EGFP for 1h. Ad5dl327CMV-EGFP (Ad-EGFP) encodes a humanized, enhanced, red-shifted jellyfish green fluorescent protein (Clontech Laboratories, Palo Alto, Calif., USA) under the control of the CMV major immediate early promoter (J. Schaack et al., submitted). After 24 h of further incubation, the cells were analyzed for fluorescence by flow cytometry (Table 2). The transduction efficiency was high in six of the seven cell lines, with greater than 90% of the cells expressing EGFP. LNCaP was the only cell line that showed relatively poor adenoviral gene transduction, as measured by both the per cent positive cells (61%), and the relatively low fluorescence intensity obtained (13-fold brighter than control cells). Similar transduction efficiencies were obtained with each of the cell lines using a multiplicity of infection of 10 p.f.u./cell (data now shown). These data indicated that adenoviral transduction would be feasible in at least six of the seven PC cell lines.

TABLE 2

Efficiency of Ad-EGFP expression in seven PC cell lines. EGFP fluorescence was measured both by the percent positive cells and the fold increase in mean fluorescent intensity as compared to untreated cells.

| Cell line | % Positive cells | Fold increase in mean fluorescence |
|---|---|---|
| ALVA-31 | 99.6 | 118 |
| JCA-1 | 98.7 | 172 |
| PPC-1 | 98.1 | 235 |
| DU 145 | 97.2 | 813 |
| TSU-Pr1 | 93.2 | 55 |
| PC-3 | 92.2 | 129 |
| LNCaP | 61.2 | 13 |

Example 12

The following example shows the effects of Ad-mFasL transduction on PC cell growth.

To determine how the PC cell lines would respond to internally expressed FasL, the growth of cell monolayers was measured for 1 week after transduction with either Ad-mFasL or Ad-EGFP as a control. In this experiment, cell monolayers were trypsinized and washed once with standard growth medium. For each cell line, $3.2\times10^5$ cells (control or $2.4\times10^5$ cells (Ad-EGFP or Ad-mFasL transduced) were placed into each of three conical Eppendorf tubes. Cells were pelleted by centrifugation, and supernatants were removed by aspiration. The pellets were resuspended in 500 μl of either plain medium (negative control), or 500 μ of medium containing approximately 10 or 100 p.f.u./cell of Ad-mFasL or Ad-EGFP. Cells were incubated for 1 h in a 37° C. water bath with periodic mixing and were then washed twice with medium. The final cell pellets were resuspended in 16 ml medium (control cells) or 12 ml medium (Ad-mFasL and Ad-EGFP transduced cells). Each sample was then aliquotted into quadruplicate wells (1 ml each) of three 24-well tissue culture plates. To quantify the amount of DNA in the initial number of cells plated (i.e. Day 0), 1 ml aliquots of the negative control were placed in four Eppendorf tubes. Cells were pelleted, supernatant was aspirated, and the cell pellets were lysed in 0.25 ml 0.5 M NaOH. Cell lysates were then frozen at −20° C. until all time points were collected. The remaining cultures were incubated at 37° C. Tissue culture medium was replaced every 48 h, and cells were harvested at the designated time points by aspirating the medium and lysing the monolayers in 0.5 M NaOH (0.25 ml/well), and freezing at −20° C. The DNA contents of the monolayers were quantified by Hoechst 33258 fluorescence using a Dynex Flurolite 1000 fluorescence plate reader (Dynex Technologies, Inc., Chantilly, Va., USA). DNA concentrations were calculated as the mean±S.D. for triplicate determinations.

Figure 3:
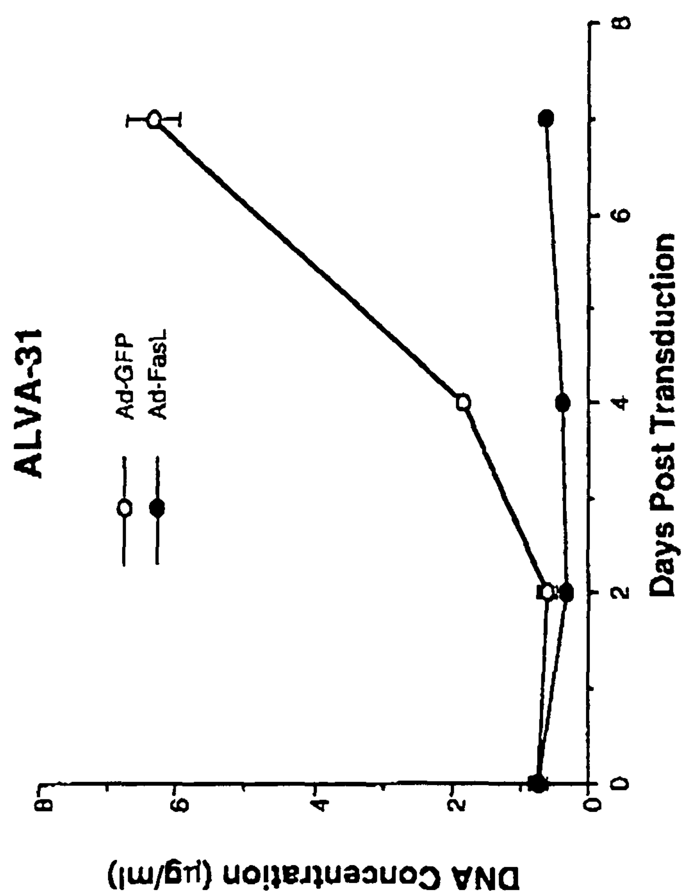
FIG. 3 is a line graph illustrating that ALVA-31 cells are far more sensitive to the natural FasL protein than they are to agonistic anti-Fas antibody.

As shown in FIG. 3, ALVA-31 cells that were treated with Ad-EGFP show logarithmic growth as they approach confluency. A phase contrast photomicrograph was taken at day 4 post-infection (data not shown). Ad-EGFP treatment did not increase apoptosis above basal levels as confirmed by the lack of nuclear fragmentation apparent after staining cells with propidium iodide and Hoechst 33342 and observing under a fluorescent microscope (data not shown). In contrast, ALVA-31 cells that were treated with Ad-mFasL were nearly completely apoptotic within 24-48 h (FIG. 3) and the few remaining cells failed to resume exponential growth over the course of this assay. Similar results were obtained with recombinant adenovirus encoding human FasL (data not shown). These data support the cytotoxicity results, suggesting that ALVA-31 cells are far more sensitive to the natural FasL protein than they are to agonistic anti-Fas antibody. Furthermore, this cell line appears to be more sensitive to internally expressed FasL than to that presented by K562-hFasL.

The short-term growth curves of other PC cell lines after adenoviral transduction are shown in FIGS. 4A-4D. The cell line PPC-1 (FIG. 4A) behaves similarly to ALVA-31 in that FasL transduction nearly obliterates the entire population of cells, and positive growth is not detected over the course of the assay. FasL transduction was to varying extent less effective on JCA-1 (FIG. 4B), PC-3 (FIG. 4C) and TSU-Pr1 (FIG. 4D) cell growth in this in vitro assay. Interestingly, TSU-Pr1 is far more sensitive to FasL when it is presented by the K562-hFasL transfectant than when it is internally expressed. The reasons for this difference are not clear. However, two explanations are possible. First, TSU-Pr1, like certain other prostate cancers, may produce high amounts of matrix metalloproteinases resulting in the production of soluble FasL which is not functional. Second, TSU-Pr1 may not efficiently trimerize FasL into its functional form. The PC cell lines DU 145 and LNCaP yielded inconsistent results in the short-term growth assays with repeated trials (data not shown). For these reasons, although it is difficult to draw any conclusions regarding the sensitivities of these two cell lines to internally expressed FasL, recent results reported by Liu and colleagues suggest that these cell lines constitutively secrete soluble FasL which could interfere with FasL-mediated apoptosis following transduction (Liu et al., 1998*, Clin. Cancer Res.* 4:1803-1811).

Example 13

The following example demonstrates the effects of Ad-FasL on prostate tumor growth in vivo.

Although the ALVA-31 cell line appeared to be quite sensitive to apoptotic induction by Ad-mFasL, it was not clear if the few remaining cells would actually be capable of regenerating over a longer period of time, and if the cells would behave similarly in an in vivo environment after FasL transduction. To address these issues, an experiment was initiated to compare the growth of ALVA-31 cells with and without Ad-mFasL after 6 weeks of growth intradermally in Nu/Nu mice. In this experiment, ALVA-31 and TSU-Pr1 cells were incubated alone (controls) or with recombinant adenoviruses (10 p.f.u./cell) for 60 min as described above for the growth assays. The cells were washed twice with tissue culture medium and once with PBS. Cell pellets were resuspended in PBS to yield a concentration of $3\times10^6$ cells per 100 μl (TSU-Pr1) or $2\times10^6$ cells per 100 μl (ALVA-31). For each PC cell line, four male Nu/Nu mice (National Cancer Institute, Bethesda, MD, USA), 6-8 weeks old, were injected intradermally with 100 μl of the cell suspensions in a total of five sites per mouse including both shoulders, both hips, and the center of the back. Each mouse, therefore, harbored three control tumors, one transduced with Ad-mFasL, and one transduced with Ad-EGFP.

When control tumors were approximately 0.5 cm in size (approximately 10 days later), two control tumors per mouse were injected in the centers with 50 μl free Ad-mFasL or Ad-EGFP virus ($5\times10^8$ pfu/ml) to determine if regression or rejection could be initiated in an already established tumor. One mouse was then sacrificed 24 h later to histologically examine the tumors. Tumor sizes were measured using calipers. Two to six weeks after the start of the experiment, the remaining mice were sacrificed and the excised tumors were fixed in formalin and embedded in paraffin. Tissue sections were then stained with hematoxylin and eosin (Histology Laboratory, Department of Surgical Pathology, UCHSC). Histologic analyses were completed with the assistance of two objective and trained Pathologists, Drs. John Ryder and Rosina DeCampo (Department of Pathology, UCHSC).

Untreated ALVA-31 cells produced tumors in 9 of 12 injection sites. However, ALVA-31 cells that were infected with Ad-mFasL (10 p.f.u./cell) prior to injection failed to produce tumors in any of four sites. Also of interest in this preliminary set of experiments was the observation that the established control tumors could not be eradicated entirely by later injection of Ad-mFasL virus ($10^7$ p.f.u./tumor). Although localized apoptosis was apparent in tissue sections near the injection sites (data not shown), the virus may not have been sufficiently dispersed within the tumor to cause significant regression. This preliminary experiment raised several other important questions. For example, one question was whether the lack of tumor growth was due specifically to FasL expression, or whether the same effect would be observed with Ad-EGFP. A second question was what were the in vivo effects of Ad-FasL in a prostate tumor cell line that appeared resistant in vitro.

To address these issues, a second set of experiments was carried out in mice using the PC cell line TSU-Pr1, whose growth was not inhibited by either Ad-EGFP or Ad-FasL in vitro. TSU-Pr1 cells were pre-infected with Ad-EGFP or Ad-mFasL as described above for the ALVA-31 cell line, and cells were injected intradermally into Nu/Nu mice. After 9 days, when control tumors were established, four control tumors were injected with Ad-EGFP or Ad-mFasL virus. One animal was then sacrificed 24 h later for histologic analysis. Calipers were used to measure the length and width of each tumor at days 9 and 18. The remaining animals were sacrificed after a total of 18 days. As shown in Table 3, there was no significant difference between the mean size of control and Ad-EGFP-infected TSU-Pr1 tumors either at day 9 or 18. In contrast, Ad-FasL tumors were significantly smaller and no change in tumor size was detected between days 9 and 18. Histologic analyses of these tumors revealed several surprising findings. First, Ad-FasL-treated tumors, although small, appeared viable, ruling out the possibility that scar tissue had completely replaced the tumor cells. Second, both Ad-FasL- and Ad-EGFP-treated tumors had extensive neutrophil infiltration (data not shown). This suggests that the initial infiltration of neutrophils is induced nonspecifically by adenoviral infection of tumor or other cells in the dermis. Furthermore, this infiltration is not in itself responsible for the regression/rejection of tumors in Ad-FasL-treated mice, as the tumors injected with Ad-EGFP were as large and as viable as control tumors. It was observed, however, that the neutrophils in the Ad-FasL-treated tumors often appeared apoptotic (data not shown). Thus, it is plausible that once the neutrophils are recruited in response to adenoviral infection, they undergo apoptosis in response to FasL, produced perhaps by dermal cells, and may potentiate a greater inflammatory response that indirectly suppresses TSU-Pr1 growth. Further experimentation will better define the role of neutrophils in mediating the rejection/regression of tumor cells that are not intrinsically sensitive to Ad-FasL mediated apoptosis.

TABLE 3

The effects of Ad-FasL on growth of TSU-Pr1 cells in nude mice. Cells were untreated (control), or pre-infected with Ad-EGFP or Ad-FasL. For comparison, several established control tumors were injected at day 10 with free Ad-EGFP or Ad-FasL virus.

| TSU-Pr1 pretreatment | Day 9 Mean tumor area ± S.E. | Day 18 Mean tumor area ± S.E. |
|---|---|---|
| Control | 9.7 ± 1.9 | 21 ± 10.3 |
| Ad-EGFP | 12.6 ± 2.3 | 27.5 ± 4.3 |
| Ad-mFasL | 2.3 ± 0.9 | 2.3 ± 0.9 |
| Injected Ad-EGFP | — | 31 ± 3.9 |
| Injected Ad-mFasL | — | 23 ± 9.2 |

The data presented in the examples above indicate that several human PC cell lines are significantly more sensitive to FasL-mediated apoptosis than was originally reported with the use of agonistic anti-Fas antibodies. Furthermore, the majority of these cell lines respond best to FasL when it is expressed internally via the adenoviral system. This method of internal expression may better represent what occurs in the prostate in vivo since the prostatic epithelium has been shown to coexpress Fas and FasL. The present inventors' in vivo experiments suggest therapeutic potential for FasL transgene expression in treating cancer patients. Given the prevalence of prostate cancer and the limited effectiveness of available therapies, further research in this area seems warranted.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of treating cancer in a mammal, comprising:

(a) introducing into the mammal a recombinant viral vector that expresses Fas ligand, wherein the mammal has metastasized cancer and wherein the recombinant viral vector is introduced directly into, or adjacent to, a tumor and (b) allowing the expression of Fas ligand to induce apoptosis in cells of the metastasized cancer.

2. The method of claim 1, wherein the metastasized cancer is derived from tissue selected from the group consisting of lung tissue, brain tissue, prostate tissue, and lymphoid tissue.

3. The method of claim 1, wherein said recombinant viral vector is from an adenovirus.

* * * * *

SEQUENCE LISTING

```
<160> NUMBER OF SEQ ID NOS: 50

<210> SEQ ID NO 1
<211> LENGTH: 20
<212> TYPE: DNA
<213> ORGANISM: Rattus sp.

<400> SEQUENCE: 1

gcccgtgaat tacccatgtc                                                  20


<210> SEQ ID NO 2
<211> LENGTH: 20
```

<212> TYPE: DNA
<213> ORGANISM: Rattus sp.

<400> SEQUENCE: 2
tggtcagcaa cggtaagatt 20

<210> SEQ ID NO 3
<211> LENGTH: 19
<212> TYPE: DNA
<213> ORGANISM: Rattus sp.

<400> SEQUENCE: 3
aacatagagc tgtggcacc 19

<210> SEQ ID NO 4
<211> LENGTH: 31183
<212> TYPE: DNA
<213> ORGANISM: adenovirus

<400> SEQUENCE: 4
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcaggatctg gaaggtgctg aggtacgatg 480
agacccgcac caggtgcaga ccctgcgagt gtggcggtaa acatattagg aaccagcctg 540
tgatgctgga tgtgaccgag gagctgaggc ccgatcactt ggtgctggcc tgcacccgcg 600
ctgagtttgg ctctagcgat gaagatacag attgaggtac tgaaatgtgt gggcgtggct 660
taagggtggg aaagaatata taaggtgggg gtcttatgta gttttgtatc tgttttgcag 720
cagccgccgc cgccatgagc accaactcgt ttgatggaag cattgtgagc tcatatttga 780
caacgcgcat gcccccatgg gccggggtgc gtcagaatgt gatgggctcc agcattgatg 840
gtcgccccgt cctgcccgca aactctacta ccttgaccta cgagaccgtg tctggaacgc 900
cgttggagac tgcagcctcc gccgccgctt cagccgctgc agccaccgcc cgcgggattg 960
tgactgactt tgctttcctg agcccgcttg caagcagtgc agcttcccgt tcatccgccc 1020
gcgatgacaa gttgacggct cttttggcac aattggattc tttgacccgg gaacttaatg 1080
tcgtttctca gcagctgttg gatctgcgcc agcaggtttc tgccctgaag gcttcctccc 1140
ctcccaatgc ggtttaaaac ataaataaaa aaccagactc tgtttggatt tggatcaagc 1200
aagtgtcttg ctgtctttat ttaggggttt tgcgcgcgcg gtaggcccgg gaccagcggt 1260
ctcggtcgtt gagggtcctg tgtatttttt ccaggacgtg gtaaaggtga ctctggatgt 1320
tcagatacat gggcataagc ccgtctctgg ggtggaggta gcaccactgc agagcttcat 1380
gctgcggggt ggtgttgtag atgatccagt cgtagcagga gcgctgggcg tggtgcctaa 1440
aaatgtcttt cagtagcaag ctgattgcca ggggcaggcc cttggtgtaa gtgtttacaa 1500
agcggttaag ctgggatggg tgcatacgtg ggatatgag atgcatcttg gactgtattt 1560
ttaggttggc tatgttccca gccatatccc tccggggatt catgttgtgc agaaccacca 1620
gcacagtgta tccggtgcac ttgggaaatt tgtcatgtag cttagaagga aatgcgtgga 1680

```
agaacttgga gacgcccttg tgacctccaa gattttccat gcattcgtcc ataatgatgg   1740
caatgggccc acgggcggcg gcctgggcga agatatttct gggatcacta acgtcatagt   1800
tgtgttccag gatgagatcg tcataggcca tttttacaaa gcgcgggcgg agggtgccag   1860
actgcggtat aatggttcca tccggcccag gggcgtagtt accctcacag atttgcattt   1920
cccacgcttt gagttcagat ggggggatca tgtctacctg cggggcgatg aagaaaacgg   1980
tttccggggt aggggagatc agctgggaag aaagcaggtt cctgagcagc tgcgacttac   2040
cgcagccggt gggcccgtaa atcacaccta ttaccgggtg caactggtag ttaagagagc   2100
tgcagctgcc gtcatccctg agcagggggg ccacttcgtt aagcatgtcc ctgactcgca   2160
tgttttccct gaccaaatcc gccagaaggc gctcgccgcc cagcgatagc agttcttgca   2220
aggaagcaaa gtttttcaac ggtttgagac cgtccgccgt aggcatgctt ttgagcgttt   2280
gaccaagcag ttccaggcgg tcccacagct cggtcacctg ctctacggca tctcgatcca   2340
gcatatctcc tcgtttcgcg ggttggggcg gctttcgctg tacggcagta gtcggtgctc   2400
gtccagacgg gccagggtca tgtctttcca cgggcgcagg gtcctcgtca gcgtagtctg   2460
ggtcacggtg aaggggtgcg ctccgggctg cgcgctggcc agggtgcgct tgaggctggt   2520
cctgctggtg ctgaagcgct gccggtcttc gccctgcgcg tcggccaggt agcatttgac   2580
catggtgtca tagtccagcc cctccgcggc gtggcccttg gcgcgcagct tgcccttgga   2640
ggaggcgccg cacgaggggc agtgcagact tttgagggcg tagagcttgg gcgcgagaaa   2700
taccgattcc ggggagtagg catccgcgcc gcaggccccg cagacggtct cgcattccac   2760
gagccaggtg agctctggcc gttcggggtc aaaaaccagg tttcccccat gctttttgat   2820
gcgtttctta cctctggttt ccatgagccg gtgtccacgc tcggtgacga aaaggctgtc   2880
cgtgtccccg tatacagact tgagaggcct gtcctcgagc ggtgttccgc ggtcctcctc   2940
gtatagaaac tcggaccact ctgagacaaa ggctcgcgtc caggccagca cgaaggaggc   3000
taagtgggag gggtagcggt cgttgtccac taggggggtcc actcgctcca gggtgtgaag   3060
acacatgtcg ccctcttcgg catcaaggaa ggtgattggt ttgtaggtgt aggccacgtg   3120
accgggtgtt cctgaagggg ggctataaaa gggggtgggg gcgcgttcgt cctcactctc   3180
ttccgcatcg ctgtctgcga gggccagctg ttggggtgag tactccctct gaaaagcggg   3240
catgacttct gcgctaagat tgtcagtttc caaaaacgag gaggatttga tattcacctg   3300
gcccgcggtg atgcctttga gggtggccgc atccatctgg tcagaaaaga caatcttttt   3360
gttgtcaagc ttggtggcaa acgacccgta gagggcgttg gacagcaact tggcgatgga   3420
gcgcagggtt tggtttttgt cgcgatcggc gcgctccttg gccgcgatgt ttagctgcac   3480
gtattcgcgc gcaacgcacc gccattcggg aaagacggtg gtgcgctcgt cgggcaccag   3540
gtgcacgcgc caaccgcggt tgtgcagggt gacaaggtca acgctggtgg ctacctctcc   3600
gcgtaggcgc tcgttggtcc agcagaggcg gccgcccttg cgcgagcaga atggcggtag   3660
ggggtctagc tgcgtctcgt ccggggggtc tgcgtccacg gtaaagaccc cgggcagcag   3720
gcgcgcgtcg aagtagtcta tcttgcatcc ttgcaagtct agcgcctgct gccatgcgcg   3780
ggcggcaagc gcgcgctcgt atgggttgag tgggggaccc catggcatgg ggtgggtgag   3840
cgcggaggcg tacatgccgc aaatgtcgta aacgtagagg ggctctctga gtattccaag   3900
atatgtaggg tagcatcttc caccgcggat gctggcgcgc acgtaatcgt atagttcgtg   3960
cgagggagcg aggaggtcgg gaccgaggtt gctacgggcg ggctgctctg ctcggaagac   4020
tatctgcctg aagatggcat gtgagttgga tgatatggtt ggacgctgga agacgttgaa   4080
```

-continued

```
gctggcgtct gtgagaccta ccgcgtcacg cacgaaggag gcgtaggagt cgcgcagctt   4140
gttgaccagc tcggcggtga cctgcacgtc tagggcgcag tagtccaggg tttccttgat   4200
gatgtcatac ttatcctgtc cctttttttt ccacagctcg cggttgagga caaactcttc   4260
gcggtctttc cagtactctt ggatcggaaa cccgtcggcc tccgaacggt aagagcctag   4320
catgtagaac tggttgacgg cctggtaggc gcagcatccc ttttctacgg gtagcgcgta   4380
tgcctgcgcg gccttccgga gcgaggtgtg ggtgagcgca aaggtgtccc tgaccatgac   4440
tttgaggtac tggtatttga agtcagtgtc gtcgcatccg ccctgctccc agagcaaaaa   4500
gtccgtgcgc tttttggaac gcggatttgg cagggcgaag gtgacatcgt tgaagagtat   4560
ctttcccgcg cgaggcataa agttgcgtgt gatgcggaag ggtcccggca cctcggaacg   4620
gttgttaatt acctgggcgg cgagcacgat ctcgtcaaag ccgttgatgt tgtggcccac   4680
aatgtaaagt tccaagaagc gcgggatgcc cttgatggaa ggcaattttt taagttcctc   4740
gtaggtgagc tcttcagggg agctgagccc gtgctctgaa agggcccagt ctgcaagatg   4800
agggttggaa gcgacgaatg agctccacag gtcacgggcc attagcattt gcaggtggtc   4860
gcgaaaggtc ctaaactggc gacctatggc catttttctt ggggtgatgc agtagaaggt   4920
aagcgggtct tgttcccagc ggtcccatcc aaggttcgcg gctaggtctc gcgcggcagt   4980
cactagaggc tcatctccgc cgaacttcat gaccagcatg aagggcacga gctgcttccc   5040
aaaggccccc atccaagtat aggtctctac atcgtaggtg acaaagagac gctcggtgcg   5100
aggatgcgag ccgatcggga agaactggat ctcccgccac caattggagg agtggctatt   5160
gatgtggtga aagtagaagt ccctgcgacg ggccgaacac tcgtgctggc ttttgtaaaa   5220
acgtgcgcag tactggcagc ggtgcacggg ctgtacatcc tgcacgaggt tgacctgacg   5280
accgcgcaca aggaagcaga gtgggaattt gagcccctcg cctggcgggt ttggctggtg   5340
gtcttctact tcggctgctt gtccttgacc gtctggctgc tcgaggggag ttacggtgga   5400
tcggaccacc acgccgcgcg agcccaaagt ccagatgtcc gcgcgcggcg gtcggagctt   5460
gatgacaaca tcgcgcagat gggagctgtc catggtctgg agctcccgcg gcgtcaggtc   5520
aggcgggagc tcctgcaggt ttacctcgca tagacgggtc agggcgcggg ctagatccag   5580
gtgataccta atttccaggg gctggttggt ggcggcgtcg atggcttgca agaggccgca   5640
tccccgcggc gcgactacgg taccgcgcgg cgggcggtgg gccgcggggg tgtccttgga   5700
tgatgcatct aaaagcggtg acgcgggcga gcccccggag gtaggggggg ctccggaccc   5760
gccgggagag gggcaggggc cacgtcggcg ccgcgcgcgg gcaggagctg gtgctgcgcg   5820
cgtaggttgc tggcgaacgc gacgacgcgg cggttgatct cctgaatctg gcgcctctgc   5880
gtgaagacga cgggcccggt gagcttgagc ctgaaagaga gttcgacaga atcaatttcg   5940
gtgtcgttga cggcggcctg gcgcaaaatc tcctgcacgt ctcctgagtt gtcttgatag   6000
gcgatctcgg ccatgaactg ctcgatctct tcctcctgga gatctccgcg tccggctcgc   6060
tccacggtgg cggcgaggtc gttggaaatg cgggccatga gctgcgagaa ggcgttgagg   6120
cctccctcgt tccagacgcg gctgtagacc acgcccccctt cggcatcgcg ggcgcgcatg   6180
accacctgcg cgagattgag ctccacgtgc cgggcgaaga cggcgtagtt tcgcaggcgc   6240
tgaaagaggt agttgagggt ggtggcggtg tgttctgcca cgaagaagta cataacccag   6300
cgtcgcaacg tggattcgtt gatatccccc aaggcctcaa ggcgctccat ggcctcgtag   6360
aagtccacgg cgaagttgaa aaactgggag ttgcgcgccg acacggttaa ctcctcctcc   6420
agaagacgga tgagctcggc gacagtgtcg cgcacctcgc gctcaaaggc tacaggggcc   6480
```

```
tcttcttctt cttcaatctc ctcttccata agggcctccc cttcttcttc ttctggcggc   6540
ggtgggggag gggggacacg gcggcgacga cggcgcaccg ggaggcggtc gacaaagcgc   6600
tcgatcatct ccccgcggcg acggcgcatg gtctcggtga cggcgcggcc gttctcgcgg   6660
gggcgcagtt ggaagacgcc gcccgtcatg tcccggttat gggttggcgg ggggctgcca   6720
tgcggcaggg atacggcgct aacgatgcat ctcaacaatt gttgtgtagg tactccgccg   6780
ccgagggacc tgagcgagtc cgcatcgacc ggatcggaaa acctctcgag aaaggcgtct   6840
aaccagtcac agtcgcaagg taggctgagc accgtggcgg gcggcagcgg gcggcggtcg   6900
gggttgtttc tggcggaggt gctgctgatg atgtaattaa agtaggcggt cttgagacgg   6960
cggatggtcg acagaagcac catgtccttg ggtccggcct gctgaatgcg caggcggtcg   7020
gccatgcccc aggcttcgtt ttgacatcgg cgcaggtctt tgtagtagtc ttgcatgagc   7080
ctttctaccg gcacttcttc ttctccttcc tcttgtcctg catctcttgc atctatcgct   7140
gcggcggcgg cggagtttgg ccgtaggtgg cgccctcttc ctcccatgcg tgtgaccccg   7200
aagcccctca tcggctgaag cagggctagg tcggcgacaa cgcgctcggc taatatggcc   7260
tgctgcacct gcgtgagggt agactggaag tcatccatgt ccacaaagcg gtggtatgcg   7320
cccgtgttga tggtgtaagt gcagttggcc ataacggacc agttaacggt ctggtgaccc   7380
ggctgcgaga gctcggtgta cctgagacgc gagtaagccc tcgagtcaaa tacgtagtcg   7440
ttgcaagtcc gcaccaggta ctggtatccc accaaaaagt gcggcggcgg ctggcggtag   7500
aggggccagc gtagggtggc cggggctccg gggggcgagat cttccaacat aaggcgatga   7560
tatccgtaga tgtacctgga catccaggtg atgccggcgg cggtggtgga ggcgcgcgga   7620
aagtcgcgga cgcggttcca gatgttgcgc agcggcaaaa agtgctccat ggtcgggacg   7680
ctctggccgg tcaggcgcgc gcaatcgttg acgctctaga ccgtgcaaaa ggagagcctg   7740
taagcgggca ctcttccgtg gtctggtgga taaattcgca agggtatcat ggcggacgac   7800
cggggttcga gccccgtatc cggccgtccg ccgtgatcca tgcggttacc gcccgcgtgt   7860
cgaacccagg tgtgcgacgt cagacaacgg gggagtgctc cttttggctt ccttccaggc   7920
gcggcggctg ctgcgctagc ttttttggcc actggccgcg cgcagcgtaa gcggttaggc   7980
tggaaagcga aagcattaag tggctcgctc cctgtagccg gagggttatt ttccaagggt   8040
tgagtcgcgg gacccccggt tcgagtctcg gaccggccgg actgcggcga acgggggttt   8100
gcctccccgt catgcaagac ccgcttgca aattcctccg gaaacaggga cgagcccctt   8160
ttttgctttt cccagatgca tccggtgctg cggcagatgc gccccctcc tcagcagcgg   8220
caagagcaag agcagcggca gacatgcagg gcaccctccc ctcctcctac cgcgtcagga   8280
ggggcgacat ccgcggttga cgcggcagca gatggtgatt acgaaccccc gcggcgccgg   8340
gcccggcact acctggactt ggaggagggc gagggcctgg cgcggctagg agcgccctct   8400
cctgagcggt acccaagggt gcagctgaag cgtgatacgc gtgaggcgta cgtgccgcgg   8460
cagaacctgt ttcgcgaccg cgagggagag gagcccgagg agatgcggga tcgaaagttc   8520
cacgcagggc gcgagctgcg gcatggcctg aatcgcgagc ggttgctgcg cgaggaggac   8580
tttgagcccg acgcgcgaac cgggattagt cccgcgcgcg cacacgtggc ggccgccgac   8640
ctggtaaccg catacgagca gacggtgaac caggagatta actttcaaaa aagctttaac   8700
aaccacgtgc gtacgcttgt ggcgcgcgag gaggtggcta taggactgat gcatctgtgg   8760
gactttgtaa gcgcgctgga gcaaaaccca aatagcaagc cgctcatggc gcagctgttc   8820
cttatagtgc agcacagcag ggacaacgag gcattcaggg atgcgctgct aaacatagta   8880
```

```
gagcccgagg gccgctggct gctcgatttg ataaacatcc tgcagagcat agtggtgcag   8940
gagcgcagct tgagcctggc tgacaaggtg gccgccatca actattccat gcttagcctg   9000
ggcaagtttt acgcccgcaa gatataccat accccttacg ttcccataga caaggaggta   9060
aagatcgagg ggttctacat gcgcatggcg ctgaaggtgc ttaccttgag cgacgacctg   9120
ggcgtttatc gcaacgagcg catccacaag gccgtgagcg tgagccggcg gcgcgagctc   9180
agcgaccgcg agctgatgca cagcctgcaa agggccctgg ctggcacggg cagcggcgat   9240
agagaggccg agtcctactt tgacgcgggc gctgacctgc gctgggcccc aagccgacgc   9300
gccctggagg cagctggggc cggacctggg ctggcggtgg cacccgcgcg cgctggcaac   9360
gtcggcggcg tggaggaata tgacgaggac gatgagtacg agccagagga cggcgagtac   9420
taagcggtga tgtttctgat cagatgatgc aagacgcaac ggacccggcg gtgcgggcgg   9480
cgctgcagag ccagccgtcc ggccttaact ccacggacga ctggcgccag gtcatggacc   9540
gcatcatgtc gctgactgcg cgcaatcctg acgcgttccg gcagcagccg caggccaacc   9600
ggctctccgc aattctggaa gcggtggtcc cggcgcgcgc aaaccccacg cacgagaagg   9660
tgctggcgat cgtaaacgcg ctggccgaaa acagggccat ccggcccgac gaggccggcc   9720
tggtctacga cgcgctgctt cagcgcgtgg ctcgttacaa cagcggcaac gtgcagacca   9780
acctggaccg gctggtgggg gatgtgcgcg aggccgtggc gcagcgtgag cgcgcgcagc   9840
agcagggcaa cctgggctcc atggttgcac taaacgcctt cctgagtaca cagcccgcca   9900
acgtgccgcg gggacaggag gactacacca actttgtgag cgcactgcgg ctaatggtga   9960
ctgagacacc gcaaagtgag gtgtaccagt ctgggccaga ctattttttc cagaccagta  10020
gacaaggcct gcagaccgta aacctgagcc aggctttcaa aaacttgcag gggctgtggg  10080
gggtgcgggc tcccacaggc gaccgcgcga ccgtgtctag cttgctgacg cccaactcgc  10140
gcctgttgct gctgctaata gcgcccttca cggacagtgg cagcgtgtcc cgggacacat  10200
acctaggtca cttgctgaca ctgtaccgcg aggccatagg tcaggcgcat gtggacgagc  10260
atactttcca ggagattaca agtgtcagcc gcgcgctggg gcaggaggac acgggcagcc  10320
tggaggcaac cctaaactac ctgctgacca accggcggca gaagatcccc tcgttgcaca  10380
gtttaaacag cgaggaggag cgcattttgc gctacgtgca gcagagcgtg agccttaacc  10440
tgatgcgcga cggggtaacg cccagcgtgg cgctggacat gaccgcgcgc aacatggaac  10500
cgggcatgta tgcctcaaac cggccgttta tcaaccgcct aatggactac ttgcatcgcg  10560
cggccgccgt gaaccccgag tatttcacca atgccatctt gaacccgcac tggctaccgc  10620
cccctggttt ctacaccggg ggattcgagg tgcccgaggg taacgatgga ttcctctggg  10680
acgacataga cgacagcgtg ttttccccgc aaccgcagac cctgctagag ttgcaacagc  10740
gcgagcaggc agaggcggcg ctgcgaaagg aaagcttccg caggccaagc agcttgtccg  10800
atctaggcgc tgcggccccg cggtcagatg ctagtagccc atttccaagc ttgatagggt  10860
ctcttaccag cactcgcacc acccgcccgc gcctgctggg cgaggaggag tacctaaaca  10920
actcgctgct gcagccgcag cgcgaaaaaa acctgcctcc ggcatttccc aacaacggga  10980
tagagagcct agtggacaag atgagtagat ggaagacgta cgcgcaggag cacagggacg  11040
tgccaggccc gcgcccgccc acccgtcgtc aaaggcacga ccgtcagcgg ggtctggtgt  11100
gggaggacga tgactcggca gacgacagca gcgtcctgga tttgggaggg agtggcaacc  11160
cgtttgcgca ccttcgcccc aggctgggga gaatgtttta aaaaaaaaaa agcatgatgc  11220
aaaataaaaa actcaccaag gccatggcac cgagcgttgg ttttcttgta ttccccttag  11280
```

```
tatgcggcgc gcggcgatgt atgaggaagg tcctcctccc tcctacgaga gtgtggtgag  11340
cgcggcgcca gtggcggcgg cgctgggttc tcccttcgat gctcccctgg acccgccgtt  11400
tgtgcctccg cggtacctgc ggcctaccgg ggggagaaac agcatccgtt actctgagtt  11460
ggcacccccta ttcgacacca cccgtgtgta cctggtggac aacaagtcaa cggatgtggc  11520
atccctgaac taccagaacg accacagcaa ctttctgacc acggtcattc aaaacaatga  11580
ctacagcccg gggggaggcaa gcacacagac catcaatctt gacgaccggt cgcactgggg  11640
cggcgacctg aaaaccatcc tgcataccaa catgccaaat gtgaacgagt tcatgtttac  11700
caataagttt aaggcgcggg tgatggtgtc gcgcttgcct actaaggaca atcaggtgga  11760
gctgaaatac gagtgggtgg agttcacgct gcccgagggc aactactccg agaccatgac  11820
catagacctt atgaacaacg cgatcgtgga gcactacttg aaagtgggca gacagaacgg  11880
ggttctggaa agcgacatcg ggtaaagtt tgacacccgc aacttcagac tggggtttga  11940
ccccgtcact ggtcttgtca tgcctggggt atatacaaac gaagccttcc atccagacat  12000
cattttgctg ccaggatgcg ggtggactt cacccacagc cgcctgagca acttgttggg  12060
catccgcaag cggcaaccct tccaggaggg ctttaggatc acctacgatg atctggaggg  12120
tggtaacatt cccgcactgt tggatgtgga cgcctaccag gcgagcttga aagatgacac  12180
cgaacagggc gggggtggcg caggcggcag caacagcagt ggcagcggcg cggaagagaa  12240
ctccaacgcg gcagccgcgg caatgcagcc ggtggaggac atgaacgatc atgccattcg  12300
cggcgacacc tttgccacac gggctgagga gaagcgcgct gaggccgaag cagcggccga  12360
agctgccgcc cccgctgcgc aacccgaggt cgagaagcct cagaagaaac cggtgatcaa  12420
acccctgaca gaggacagca agaaacgcag ttacaaccta ataagcaatg acagcacctt  12480
cacccagtac cgcagctggt accttgcata caactacggc gaccctcaga ccggaatccg  12540
ctcatggacc ctgctttgca ctcctgacgt aacctgcggc tcggagcagg tctactggtc  12600
gttgccagac atgatgcaag accccgtgac cttccgctcc acgcgccaga tcagcaactt  12660
tccggtggtg ggcgccgagc tgttgcccgt gcactccaag agcttctaca acgaccaggc  12720
cgtctactcc caactcatcc gccagtttac ctctctgacc cacgtgttca atcgctttcc  12780
cgagaaccag attttggcgc gcccgccagc ccccaccatc accaccgtca gtgaaaacgt  12840
tcctgctctc acagatcacg ggacgctacc gctgcgcaac agcatcggag gagtccagcg  12900
agtgaccatt actgacgcca gacgccgcac ctgcccctac gtttacaagg ccctgggcat  12960
agtctcgccg cgcgtcctat cgagccgcac tttttgagca agcatgtcca tccttatatc  13020
gcccagcaat aacacaggct ggggcctgcg cttcccaagc aagatgtttg gcggggccaa  13080
gaagcgctcc gaccaacacc cagtgcgcgt gcgcgggcac taccgcgcgc cctggggcgc  13140
gcacaaacgc ggccgcactg ggcgcaccac cgtcgatgac gccatcgacg cggtggtgga  13200
ggaggcgcgc aactacacgc ccacgccgcc accagtgtcc acagtggacg cggccattca  13260
gaccgtggtg cgcggagccc ggcgctatgc taaaatgaag agacggcgga ggcgcgtagc  13320
acgtcgccac cgccgccgac ccggcactgc cgcccaacgc gcggcggcgg ccctgcttaa  13380
ccgcgcacgt cgcaccggcc gacgggcggc catgcgggcc gctcgaaggc tggccgcggg  13440
tattgtcact gtgcccccca ggtccaggcg acgagcggcc gccgcagcag ccgcggccat  13500
tagtgctatg actcagggtc gcaggggcaa cgtgtattgg gtgcgcgact cggttagcgg  13560
cctgcgcgtg cccgtgcgca cccgcccccc gcgcaactag attgcaagaa aaaactactt  13620
agactcgtac tgttgtatgt atccagcggc ggcggcgcgc aacgaagcta tgtccaagcg  13680
```

```
caaaatcaaa gaagagatgc tccaggtcat cgcgccggag atctatggcc ccccgaagaa  13740
ggaagagcag gattacaagc cccgaaagct aaagcgggtc aaaaagaaaa agaaagatga  13800
tgatgatgaa cttgacgacg aggtggaact gctgcacgct accgcgccca ggcgacgggt  13860
acagtggaaa ggtcgacgcg taaaacgtgt tttgcgaccc ggcaccaccg tagtctttac  13920
gcccggtgag cgctccaccc gcacctacaa gcgcgtgtat gatgaggtgt acggcgacga  13980
ggacctgctt gagcaggcca acgagcgcct cggggagttt gcctacggaa agcggcataa  14040
ggacatgctg gcgttgccgc tggacgaggg caacccaaca cctagcctaa agcccgtaac  14100
actgcagcag gtgctgcccg cgcttgcacc gtccgaagaa aagcgcggcc taaagcgcga  14160
gtctggtgac ttggcaccca ccgtgcagct gatggtaccc aagcgccagc gactggaaga  14220
tgtcttggaa aaaatgaccg tggaacctgg gctggagccc gaggtccgcg tgcggccaat  14280
caagcaggtg gcgccgggac tgggcgtgca gaccgtggac gttcagatac ccactaccag  14340
tagcaccagt attgccaccg ccacagaggg catggagaca caaacgtccc cggttgcctc  14400
agcggtggcg gatgccgcgg tgcaggcggt cgctgcggcc gcgtccaaga cctctacgga  14460
ggtgcaaacg gacccgtgga tgtttcgcgt ttcagccccc cggcgcccgc gcggttcgag  14520
gaagtacggc gccgccagcg cgctactgcc cgaatatgcc ctacatcctt ccattgcgcc  14580
tacccccggc tatcgtggct acacctaccg ccccagaaga cgagcaacta cccgacgccg  14640
aaccaccact ggaacccgcc gccgccgtcg ccgtcgccag cccgtgctgg ccccgatttc  14700
cgtgcgcagg gtggctcgcg aaggaggcag gaccctggtg ctgccaacag cgcgctacca  14760
ccccagcatc gtttaaaagc cggtctttgt ggttcttgca gatatggccc tcacctgccg  14820
cctccgtttc ccggtgccgg gattccgagg aagaatgcac cgtaggaggg gcatggccgg  14880
ccacggcctg acgggcggca tgcgtcgtgc gcaccaccgg cggcggcgcg cgtcgcaccg  14940
tcgcatgcgc ggcggtatcc tgcccctcct tattccactg atcgccgcgg cgattggcgc  15000
cgtgcccgga attgcatccg tggccttgca ggcgcagaga cactgattaa aaacaagttg  15060
catgtggaaa aatcaaaata aaaagtctgg actctcacgc tcgcttggtc ctgtaactat  15120
tttgtagaat ggaagacatc aactttgcgt ctctggcccc gcgacacggc tcgcgcccgt  15180
tcatgggaaa ctggcaagat atcggcacca gcaatatgag cggtggcgcc ttcagctggg  15240
gctcgctgtg gagcggcatt aaaaatttcg gttccaccgt taagaactat ggcagcaagg  15300
cctggaacag cagcacaggc cagatgctga gggataagtt gaaagagcaa aatttccaac  15360
aaaaggtggt agatggcctg gcctctggca ttagcggggt ggtggacctg gccaaccagg  15420
cagtgcaaaa taagattaac agtaagcttg atccccgccc tcccgtagag gagcctccac  15480
cggccgtgga gacagtgtct ccagaggggc gtggcgaaaa gcgtccgcgc cccgacaggg  15540
aagaaactct ggtgacgcaa atagacgagc ctccctcgta cgaggaggca ctaaagcaag  15600
gcctgcccac cacccgtccc atcgcgccca tggctaccgg agtgctgggc cagcacacac  15660
ccgtaacgct ggacctgcct ccccccgccg acacccagca gaaacctgtg ctgccaggcc  15720
cgaccgccgt tgttgtaacc cgtcctagcc gcgcgtccct gcgccgcgcc gccagcggtc  15780
cgcgatcgtt gcggcccgta gccagtggca actggcaaag cacactgaac agcatcgtgg  15840
gtctgggggt gcaatccctg aagcgccgac gatgcttctg aatagctaac gtgtcgtatg  15900
tgtgtcatgt atgcgtccat gtcgccgcca gaggagctgc tgagccgccg cgcgcccgct  15960
ttccaagatg gctacccctt cgatgatgcc gcagtggtct tacatgcaca tctcgggcca  16020
ggacgcctcg gagtacctga gccccgggct ggtgcagttt gcccgcgcca ccgagacgta  16080
```

```
cttcagcctg aataacaagt ttagaaaccc cacggtggcg cctacgcacg acgtgaccac  16140
agaccggtcc cagcgtttga cgctgcggtt catccctgtg gaccgtgagg atactgcgta  16200
ctcgtacaag gcgcggttca ccctagctgt gggtgataac cgtgtgctgg acatggcttc  16260
cacgtacttt gacatccgcg gcgtgctgga caggggccct acttttaagc cctactctgg  16320
cactgcctac aacgccctgg ctcccaaggg tgccccaaat ccttgcgaat gggatgaagc  16380
tgctactgct cttgaaataa acctagaaga agaggacgat gacaacgaag acgaagtaga  16440
cgagcaagct gagcagcaaa aaactcacgt atttgggcag gcgccttatt ctggtataaa  16500
tattacaaag gagggtattc aaataggtgt cgaaggtcaa acacctaaat atgccgataa  16560
aacatttcaa cctgaacctc aaataggaga atctcagtgg tacgaaactg aaattaatca  16620
tgcagctggg agagtcctta aaaagactac cccaatgaaa ccatgttacg gttcatatgc  16680
aaaacccaca aatgaaaatg gagggcaagg cattcttgta aagcaacaaa atggaaagct  16740
agaaagtcaa gtggaaatgc aatttttctc aactactgag gcgaccgcag gcaatggtga  16800
taacttgact cctaaagtgg tattgtacag tgaagatgta gatatagaaa ccccagacac  16860
tcatatttct tacatgccca ctattaagga aggtaactca cgagaactaa tgggccaaca  16920
atctatgccc aacaggccta attacattgc ttttagggac aattttattg gtctaatgta  16980
ttacaacagc acgggtaata tgggtgttct ggcgggccaa gcatcgcagt tgaatgctgt  17040
tgtagatttg caagacagaa acacagagct ttcataccag cttttgcttg attccattgg  17100
tgatagaacc aggtactttt ctatgtggaa tcaggctgtt gacagctatg atccagatgt  17160
tagaattatt gaaaatcatg gaactgaaga tgaacttcca aattactgct ttccactggg  17220
aggtgtgatt aatacagaga ctcttaccaa ggtaaaacct aaaacaggtc aggaaaatgg  17280
atgggaaaaa gatgctacag aattttcaga taaaaatgaa ataagagttg gaaataattt  17340
tgccatggaa atcaatctaa atgccaacct gtggagaaat ttcctgtact ccaacatagc  17400
gctgtatttg cccgacaagc taaagtacag tccttccaac gtaaaaattt ctgataaccc  17460
aaacacctac gactacatga acaagcgagt ggtggctccc gggttagtgg actgctacat  17520
taaccttgga gcacgctggt cccttgacta tatggacaac gtcaacccat ttaaccacca  17580
ccgcaatgct ggcctgcgct accgctcaat gttgctgggc aatggtcgct atgtgccctt  17640
ccacatccag gtgcctcaga agttctttgc cattaaaaac ctccttctcc tgccgggctc  17700
atacacctac gagtggaact tcaggaagga tgttaacatg gttctgcaga gctccctagg  17760
aaatgaccta agggttgacg gagccagcat taagtttgat agcatttgcc tttacgccac  17820
cttcttcccc atggcccaca acaccgcctc cacgcttgag gccatgctta gaaacgacac  17880
caacgaccag tcctttaacg actatctctc cgccgccaac atgctctacc ctatacccgc  17940
caacgctacc aacgtgccca tatccatccc ctcccgcaac tgggcggctt tccgcggctg  18000
ggccttcacg cgccttaaga ctaaggaaac cccatcactg ggctcgggct acgaccctta  18060
ttacacctac tctggctcta taccctacct agatggaacc ttttacctca accacacctt  18120
taagaaggtg gccattacct ttgactcttc tgtcagctgg cctggcaatg accgcctgct  18180
tacccccaac gagtttgaaa ttaagcgctc agttgacggg gagggttaca acgttgccca  18240
gtgtaacatg accaaagact ggttcctggt acaaatgcta gctaactaca acattggcta  18300
ccagggcttc tatatcccag agagctacaa ggaccgcatg tactccttct ttagaaactt  18360
ccagcccatg agccgtcagg tggtggatga tactaaatac aaggactacc aacaggtggg  18420
catcctacac caacacaaca actctggatt tgttggctac cttgcccccca ccatgcgcga  18480
```

```
aggacaggcc taccctgcta acttccccta tccgcttata ggcaagaccg cagttgacag  18540
cattacccag aaaaagtttc tttgcgatcg cacccctttgg cgcatcccat tctccagtaa  18600
ctttatgtcc atgggcgcac tcacagacct gggccaaaac cttctctacg ccaactccgc  18660
ccacgcgcta gacatgactt ttgaggtgga tcccatggac gagcccaccc ttctttatgt  18720
tttgtttgaa gtctttgacg tggtccgtgt gcaccggccg caccgcggcg tcatcgaaac  18780
cgtgtacctg cgcacgccct tctcggccgg caacgccaca acataaagaa gcaagcaaca  18840
tcaacaacag ctgccgccat gggctccagt gagcaggaac tgaaagccat tgtcaaagat  18900
cttggttgtg ggccatattt tttgggcacc tatgacaagc gctttccagg ctttgtttct  18960
ccacacaagc tcgcctgcgc catagtcaat acggccggtc gcgagactgg gggcgtacac  19020
tggatggcct ttgcctggaa cccgcactca aaaacatgct acctctttga gccctttggc  19080
ttttctgacc agcgactcaa gcaggtttac cagtttgagt acgagtcact cctgcgccgt  19140
agcgccattg cttcttcccc cgaccgctgt ataacgctgg aaaagtccac ccaaagcgta  19200
caggggccca actcggccgc ctgtggacta ttctgctgca tgtttctcca cgcctttgcc  19260
aactggcccc aaactcccat ggatcacaac cccaccatga accttattac cggggtaccc  19320
aactccatgc tcaacagtcc ccaggtacag cccaccctgc gtcgcaacca ggaacagctc  19380
tacagcttcc tggagcgcca ctcgccctac ttccgcagcc acagtgcgca gattaggagc  19440
gccacttctt tttgtcactt gaaaaacatg taaaaataat gtactagaga cactttcaat  19500
aaaggcaaat gcttttattt gtacactctc gggtgattat ttaccccccac ccttgccgtc  19560
tgcgccgttt aaaaatcaaa ggggttctgc cgcgcatcgc tatgcgccac tggcagggac  19620
acgttgcgat actggtgttt agtgctccac ttaaactcag gcacaaccat ccgcggcagc  19680
tcggtgaagt tttcactcca caggctgcgc accatcacca acgcgtttag caggtcgggc  19740
gccgatatct tgaagtcgca gttggggcct ccgccctgcg cgcgcgagtt gcgatacaca  19800
gggttgcagc actggaacac tatcagcgcc gggtggtgca cgctggccag cacgctcttg  19860
tcggagatca gatccgcgtc caggtcctcc gcgttgctca gggcgaacgg agtcaacttt  19920
ggtagctgcc ttcccaaaaa gggcgcgtgc ccaggctttg agttgcactc gcaccgtagt  19980
ggcatcaaaa ggtgaccgtg cccggtctgg gcgttaggat acagcgcctg cataaaagcc  20040
ttgatctgct taaaagccac ctgagccttt gcgccttcag agaagaacat gccgcaagac  20100
ttgccggaaa actgattggc cggacaggcc gcgtcgtgca cgcagcacct tgcgtcggtg  20160
ttggagatct gcaccacatt tcggccccac cggttcttca cgatcttggc cttgctagac  20220
tgctccttca gcgcgcgctg cccgttttcg ctcgtcacat ccatttcaat cacgtgctcc  20280
ttatttatca taatgcttcc gtgtagacac ttaagctcgc cttcgatctc agcgcagcgg  20340
tgcagccaca acgcgcagcc cgtgggctcg tgatgcttgt aggtcacctc tgcaaacgac  20400
tgcaggtacg cctgcaggaa tcgccccatc atcgtcacaa aggtcttgtt gctggtgaag  20460
gtcagctgca acccgcggtg ctcctcgttc agccaggtct tgcatacggc cgccagagct  20520
tccacttggt caggcagtag tttgaagttc gcctttagat cgttatccac gtggtacttg  20580
tccatcagcg cgcgcgcagc ctccatgccc ttctcccacg cagacacgat cggcacactc  20640
agcgggttca tcaccgtaat ttcactttcc gcttcgctgg gctcttcctc ttcctcttgc  20700
gtccgcatac cacgcgccac tgggtcgtct tcattcagcc gccgcactgt gcgcttacct  20760
cctttgccat gcttgattag caccggtggg ttgctgaaac ccaccatttg tagcgccaca  20820
tcttctcttt cttcctcgct gtccacgatt acctctggtg atggcgggcg ctcgggcttg  20880
```

```
ggagaagggc gcttcttttt cttcttgggc gcaatggcca aatccgccgc cgaggtcgat  20940
ggccgcgggc tgggtgtgcg cggcaccagc gcgtcttgtg atgagtcttc ctcgtcctcg  21000
gactcgatac gccgcctcat ccgctttttt gggggcgccc ggggaggcgg cggcgacggg  21060
gacggggacg acacgtcctc catggttggg ggacgtcgcg ccgcaccgcg tccgcgctcg  21120
ggggtggttt cgcgctgctc ctcttcccga ctggccattt ccttctccta taggcagaaa  21180
aagatcatgg agtcagtcga gaagaaggac agcctaaccg ccccctctga gttcgccacc  21240
accgcctcca ccgatgccgc caacgcgcct accaccttcc ccgtcgaggc acccccgctt  21300
gaggaggagg aagtgattat cgagcaggac ccaggttttg taagcgaaga cgacgaggac  21360
cgctcagtac caacagagga taaaaagcaa gaccaggaca acgcagaggc aaacgaggaa  21420
caagtcgggc ggggggacga aaggcatggc gactacctag atgtgggaga cgacgtgctg  21480
ttgaagcatc tgcagcgcca gtgcgccatt atctgcgacg cgttgcaaga gcgcagcgat  21540
gtgcccctcg ccatagcgga tgtcagcctt gcctacgaac gccacctatt ctcaccgcgc  21600
gtaccccca aacgccaaga aaacggcaca tgcgagccca acccgcgcct caacttctac  21660
cccgtatttg ccgtgccaga ggtgcttgcc acctatcaca tctttttcca aaactgcaag  21720
atacccctat cctgccgtgc caaccgcagc cgagcggaca agcagctggc cttgcggcag  21780
ggcgctgtca tacctgatat cgcctcgctc aacgaagtgc caaaaatctt tgagggtctt  21840
ggacgcgacg agaagcgcgc ggcaaacgct ctgcaacagg aaaacagcga aaatgaaagt  21900
cactctggag tgttggtgga actcgagggt gacaacgcgc gcctagccgt actaaaacgc  21960
agcatcgagg tcacccactt tgcctacccg gcacttaacc taccccccaa ggtcatgagc  22020
acagtcatga gtgagctgat cgtgcgccgt gcgcagcccc tggagaggga tgcaaatttg  22080
caagaacaaa cagaggaggg cctacccgca gttggcgacg agcagctagc gcgctggctt  22140
caaacgcgcg agcctgccga cttggaggag cgacgcaaac taatgatggc cgcagtgctc  22200
gttaccgtgg agcttgagtg catgcagcgg ttctttgctg acccggagat gcagcgcaag  22260
ctagaggaaa cattgcacta cacctttcga cagggctacg tacgccaggc ctgcaagatc  22320
tccaacgtgg agctctgcaa cctggtctcc taccttggaa ttttgcacga aaaccgcctt  22380
gggcaaaacg tgcttcattc cacgctcaag ggcgaggcgc gccgcgacta cgtccgcgac  22440
tgcgtttact tatttctatg ctacacctgg cagacggcca tgggcgtttg gcagcagtgc  22500
ttggaggagt gcaacctcaa ggagctgcag aaactgctaa agcaaaactt gaaggaccta  22560
tggacggcct tcaacgagcg ctccgtggcc gcgcacctgg cggacatcat tttccccgaa  22620
cgcctgctta aaccctgca acagggtctg ccagacttca ccagtcaaag catgttgcag  22680
aactttagga actttatcct agagcgctca ggaatcttgc ccgccacctg ctgtgcactt  22740
cctagcgact ttgtgcccat taagtaccgc gaatgccctc cgccgctttg gggccactgc  22800
taccttctgc agctagccaa ctaccttgcc taccactctg acataatgga agacgtgagc  22860
ggtgacggtc tactggagtg tcactgtcgc tgcaacctat gcaccccgca ccgctccctg  22920
gtttgcaatt cgcagctgct taacgaaagt caaattatcg gtacctttga gctgcagggt  22980
ccctcgcctg acgaaaagtc cgcggctccg gggttgaaac tcactccggg gctgtggacg  23040
tcggcttacc ttcgcaaatt tgtacctgag gactaccacg cccacgagat taggttctac  23100
gaagaccaat cccgcccgcc aaatgcggag cttaccgcct gcgtcattac ccagggccac  23160
attcttggcc aattgcaagc catcaacaaa gcccgccaag agtttctgct acgaaaggga  23220
cggggggttt acttggaccc ccagtccggc gaggagctca acccaatccc cccgccgccg  23280
```

```
cagccctatc agcagcagcc gcgggccctt gcttcccagg atggcaccca aaaagaagct  23340
gcagctgccg ccgccaccca cggacgagga ggaatactgg gacagtcagg cagaggaggt  23400
tttggacgag gaggaggagg acatgatgga agactgggag agcctagacg aggaagcttc  23460
cgaggtcgaa gaggtgtcag acgaaacacc gtcaccctcg gtcgcattcc cctcgccggc  23520
gccccagaaa tcggcaaccg gttccagcat ggctacaacc tccgctcctc aggcgccgcc  23580
ggcactgccc gttcgccgac ccaaccgtag atgggacacc actggaacca gggccggtaa  23640
gtccaagcag ccgccgccgt tagcccaaga gcaacaacag cgccaaggct accgctcatg  23700
gcgcgggcac aagaacgcca tagttgcttg cttgcaagac tgtgggggca acatctcctt  23760
cgcccgccgc tttcttctct accatcacgg cgtggccttc cccgtaaca tcctgcatta  23820
ctaccgtcat ctctacagcc catactgcac cggcggcagc ggcagcggca gcaacagcag  23880
cggccacaca gaagcaaagg cgaccggata gcaagactct gacaaagccc aagaaatcca  23940
cagcggcggc agcagcagga ggaggagcgc tgcgtctggc gcccaacgaa cccgtatcga  24000
cccgcgagct tagaaacagg atttttccca ctctgtatgc tatatttcaa cagagcaggg  24060
gccaagaaca agagctgaaa ataaaaaaca ggtctctgcg atccctcacc cgcagctgcc  24120
tgtatcacaa aagcgaagat cagcttcggc gcacgctgga agacgcggag gctctcttca  24180
gtaaatactg cgcgctgact cttaaggact agtttcgcgc cctttctcaa atttaagcgc  24240
gaaaactacg tcatctccag cggccacacc cggcgccagc acctgtcgtc agcgccatta  24300
tgagcaagga aattcccacg ccctacatgt ggagttacca gccacaaatg ggacttgcgg  24360
ctggagctgc ccaagactac tcaacccgaa taaactacat gagcgcggga ccccacatga  24420
tatcccgggt caacggaatc cgcgcccacc gaaaccgaat tctcttggaa caggcggcta  24480
ttaccaccac acctcgtaat aaccttaatc cccgtagttg gcccgctgcc ctggtgtacc  24540
aggaaagtcc cgctcccacc actgtggtac ttcccagaga cgcccaggcc gaagttcaga  24600
tgactaactc aggggcgcag cttgcgggcg gctttcgtca cagggtgcgg tcgcccgggc  24660
agggtataac tcacctgaca atcagagggc gaggtattca gctcaacgac gagtcggtga  24720
gctcctcgct tggtctccgt ccggacggga catttcagat cggcggcgcc ggccgtcctt  24780
cattcacgcc tcgtcaggca atcctaactc tgcagacctc gtcctctgag ccgcgctctg  24840
gaggcattgg aactctgcaa tttattgagg agtttgtgcc atcggtctac tttaacccct  24900
tctcgggacc tcccggccac tatccggatc aatttattcc taactttgac gcggtaaagg  24960
actcggcgga cggctacgac tgaatgttaa gtggagaggc agagcaactg cgcctgaaac  25020
acctggtcca ctgtcgccgc cacaagtgct ttgcccgcga ctccggtgag ttttgctact  25080
ttgaattgcc cgaggatcat atcgagggcc cggcgcacgg cgtccggctt accgcccagg  25140
gagagcttgc ccgtagcctg attcgggagt ttacccagcg ccccctgcta gttgagcggg  25200
acaggggacc ctgtgttctc actgtgattt gcaactgtcc taaccttgga ttacatcaag  25260
atctttgttg ccatctctgt gctgagtata ataaatacag aaattaaaat atactggggc  25320
tcctatcgcc atcctgtaaa cgccaccgtc ttcacccgcc caagcaaacc aaggcgaacc  25380
ttacctggta cttttaacat ctctccctct gtgatttaca acagtttcaa cccagacgga  25440
gtgagtctac gagagaacct ctccgagctc agctactcca tcagaaaaaa caccaccctc  25500
cttacctgcc gggaacgtac gagtgcgtca ccggccgctg caccacacct accgcctgac  25560
cgtaaaccag actttttccg gacagacctc aataactctg tttaccagaa caggaggtga  25620
gcttagaaaa cccttagggt attaggccaa aggcgcagct actgtggggt ttatgaacaa  25680
```

```
ttcaagcaac tctacgggct attctaattc aggtttctct agaaatggac ggaattatta  25740
cagagcagcg cctgctagaa agacgcaggg cagcggccga gcaacagcgc atgaatcaag  25800
agctccaaga catggttaac ttgcaccagt gcaaaagggg tatcttttgt ctggtaaagc  25860
aggccaaagt cacctacgac agtaatacca ccggacaccg ccttagctac aagttgccaa  25920
ccaagcgtca gaaattggtg gtcatggtgg gagaaaagcc cattaccata actcagcact  25980
cggtagaaac cgaaggctgc attcactcac cttgtcaagg acctgaggat ctctgcaccc  26040
ttattaagac cctgtgcggt ctcaaagatc ttattccctt taactaataa aaaaaaataa  26100
taaagcatca cttacttaaa atcagttagc aaatttctgt ccagtttatt cagcagcacc  26160
tccttgccct cctcccagct ctggtattgc agcttcctcc tggctgcaaa ctttctccac  26220
aatctaaatg gaatgtcagt ttcctcctgt tcctgtccat ccgcacccac tatcttcatg  26280
ttgttgcaga tgaagcgcgc aagaccgtct gaagatacct tcaaccccgt gtatccatat  26340
gacacggaaa ccggtcctcc aactgtgcct ttcttactcc ctccctttgt atcccccaat  26400
gggtttcaag agagtccccc tggggtactc tctttgcgcc tatccgaacc tctagttacc  26460
tccaatggca tgcttgcgct caaaatgggc aacggcctct ctctggacga ggccggcaac  26520
cttacctccc aaaatgtaac cactgtgagc ccacctctca aaaaaaccaa gtcaaacata  26580
aacctggaaa tatctgcacc cctcacagtt acctcagaag ccctaactgt ggctgccgcc  26640
gcacctctaa tggtcgcggg caacacactc accatgcaat cacaggcccc gctaaccgtg  26700
cacgactcca aacttagcat tgccacccaa ggacccctca cagtgtcaga aggaaagcta  26760
gccctgcaaa catcaggccc cctcaccacc accgatagca gtacccttac tatcactgcc  26820
tcacccccctc taactactgc cactggtagc ttgggcattg acttgaaaga gcccatttat  26880
acacaaaatg gaaaactagg actaaagtac ggggctcctt tgcatgtaac agacgaccta  26940
aacactttga ccgtagcaac tggtccaggt gtgactatta ataatacttc cttgcaaact  27000
aaagttactg gagccttggg ttttgattca caaggcaata tgcaacttaa tgtagcagga  27060
ggactaagga ttgattctca aaacagacgc cttatacttg atgttagtta tccgtttgat  27120
gctcaaaacc aactaaatct aagactagga cagggccctc tttttataaa ctcagcccac  27180
aacttggata ttaactacaa caaaggcctt tacttgttta cagcttcaaa caattccaaa  27240
aagcttgagg ttaacctaag cactgccaag gggttgatgt ttgacgctac agccatagcc  27300
attaatgcag gagatgggct tgaatttggt tcacctaatg caccaaacac aaatcccctc  27360
aaaacaaaaa ttggccatgg cctagaattt gattcaaaca aggctatggt tcctaaacta  27420
ggaactggcc ttagttttga cagcacaggt gccattacag taggaaacaa aaataatgat  27480
aagctaactt tgtggaccac accagctcca tctcctaact gtagactaaa tgcagagaaa  27540
gatgctaaac tcactttggt cttaacaaaa tgtggcagtc aaatacttgc tacagtttca  27600
gttttggctg ttaaaggcag tttggctcca atatctggaa cagttcaaag tgctcatctt  27660
attataagat ttgacgaaaa tggagtgcta ctaaacaatt ccttcctgga cccagaatat  27720
tggaacttta gaaatggaga tcttactgaa ggcacagcct atacaaacgc tgttggattt  27780
atgcctaacc tatcagctta tccaaaatct cacggtaaaa ctgccaaaag taacattgtc  27840
agtcaagttt acttaaacgg agacaaaact aaacctgtaa cactaaccat tacactaaac  27900
ggtacacagg aaacaggaga cacaactcca agtgcatact ctatgtcatt ttcatgggac  27960
tggtctggcc acaactacat taatgaaata tttgccacat cctcttacac tttttcatac  28020
attgcccaag aataaagaat cgtttgtgtt atgtttcaac gtgtttattt ttcaattgca  28080
```

```
gaaaatttca agtcattttt cattcagtag tatagcccca ccaccacata gcttatacag  28140
atcaccgtac cttaatcaaa ctcacagaac cctagtattc aacctgccac ctccctccca  28200
acacacagag tacacagtcc tttctccccg gctggcctta aaaagcatca tatcatgggt  28260
aacagacata ttcttaggtg ttatattcca cacggtttcc tgtcgagcca aacgctcatc  28320
agtgatatta ataaactccc cgggcagctc acttaagttc atgtcgctgt ccagctgctg  28380
agccacaggc tgctgtccaa cttgcggttg cttaacgggc ggcgaaggag aagtccacgc  28440
ctacatgggg gtagagtcat aatcgtgcat caggataggg cggtggtgct gcagcagcgc  28500
gcgaataaac tgctgccgcc gccgctccgt cctgcaggaa tacaacatgg cagtggtctc  28560
ctcagcgatg attcgcaccg cccgcagcat aaggcgcctt gtcctccggg cacagcagcg  28620
caccctgatc tcacttaaat cagcacagta actgcagcac agcaccacaa tattgttcaa  28680
aatcccacag tgcaaggcgc tgtatccaaa gctcatggcg gggaccacag aacccacgtg  28740
gccatcatac cacaagcgca ggtagattaa gtggcgaccc ctcataaaca cgctggacat  28800
aaacattacc tcttttggca tgttgtaatt caccacctcc cggtaccata taaacctctg  28860
attaaacatg gcgccatcca ccaccatcct aaaccagctg gccaaaacct gcccgccggc  28920
tatacactgc agggaaccgg gactggaaca atgacagtgg agagcccagg actcgtaacc  28980
atggatcatc atgctcgtca tgatatcaat gttggcacaa cacaggcaca cgtgcataca  29040
cttcctcagg attacaagct cctcccgcgt tagaaccata tcccagggaa caacccattc  29100
ctgaatcagc gtaaatccca cactgcaggg aagacctcgc acgtaactca cgttgtgcat  29160
tgtcaaagtg ttacattcgg gcagcagcgg atgatcctcc agtatggtag cgcgggtttc  29220
tgtctcaaaa ggaggtagac gatccctact gtacggagtg cgccgagaca accgagatcg  29280
tgttggtcgt agtgtcatgc caaatggaac gccggacgta gtcatatttc ctgaagcaaa  29340
accaggtgcg ggcgtgacaa acagatctgc gtctccggtc tcgccgctta gatcgctctg  29400
tgtagtagtt gtagtatatc cactctctca aagcatccag gcgcccccctg gcttcgggtt  29460
ctatgtaaac tccttcatgc gccgctgccc tgataacatc caccaccgca gaataagcca  29520
cacccagcca acctacacat tcgttctgcg agtcacacac gggaggagcg ggaagagctg  29580
gaagaaccat gttttttttt ttattccaaa agattatcca aaacctcaaa atgaagatct  29640
attaagtgaa cgcgctcccc tccggtggcg tggtcaaact ctacagccaa agaacagata  29700
atggcatttg taagatgttg cacaatggct tccaaaaggc aaacggccct cacgtccaag  29760
tggacgtaaa ggctaaaccc ttcagggtga atctcctcta taaacattcc agcaccttca  29820
accatgccca aataattctc atctcgccac cttctcaata tatctctaag caaatcccga  29880
atattaagtc cggccattgt aaaaatctgc tccagagcgc cctccacctt cagcctcaag  29940
cagcgaatca tgattgcaaa aattcaggtt cctcacagac ctgtataaga ttcaaaagcg  30000
gaacattaac aaaaataccg cgatcccgta ggtcccttcg cagggccagc tgaacataat  30060
cgtgcaggtc tgcacggacc agcgcggcca cttccccgcc aggaaccttg acaaaagaac  30120
ccacactgat tatgacacgc atactcggag ctatgctaac cagcgtagcc ccgatgtaag  30180
ctttgttgca tgggcggcga tataaaatgc aaggtgctgc tcaaaaaatc aggcaaagcc  30240
tcgcgcaaaa aagaaagcac atcgtagtca tgctcatgca gataaaggca ggtaagctcc  30300
ggaaccacca cagaaaaaga caccattttt ctctcaaaca tgtctgcggg tttctgcata  30360
aacacaaaat aaaataacaa aaaaacattt aaacattaga agcctgtctt acaacaggaa  30420
aaacaaccct tataagcata agacggacta cggccatgcc ggcgtgaccg taaaaaaact  30480
```

```
ggtcaccgtg attaaaaagc accaccgaca gctcctcggt catgtccgga gtcataatgt  30540

aagactcggt aaacacatca ggttgattca tcggtcagtg ctaaaaagcg accgaaatag  30600

cccgggggaa tacatacccg caggcgtaga gacaacatta cagcccccat aggaggtata  30660

acaaaattaa taggagagaa aaacacataa acacctgaaa aaccctcctg cctaggcaaa  30720

atagcaccct cccgctccag aacaacatac agcgcttcac agcggcagcc taacagtcag  30780

ccttaccagt aaaaaagaaa acctattaaa aaaacaccac tcgacacggc accagctcaa  30840

tcagtcacag tgtaaaaaag ggccaagtgc agagcgagta tatataggac taaaaaatga  30900

cgtaacggtt aaagtccaca aaaaacaccc agaaaaccgc acgcgaacct acgcccagaa  30960

acgaaagcca aaaaacccac aacttcctca aatcgtcact tccgttttcc cacgttacgt  31020

aacttcccat tttaagaaaa ctacaattcc caacacatac aagttactcc gccctaaaac  31080

ctacgtcacc cgccccgttc ccacgccccg cgccacgtca caaactccac cccctcatta  31140

tcatattggc ttcaatccaa aataaggtat attattgatg atg                    31183


<210> SEQ ID NO 5
<211> LENGTH: 1890
<212> TYPE: DNA
<213> ORGANISM: Homo sapiens
<220> FEATURE:
<221> NAME/KEY: CDS
<222> LOCATION: (189)..(1034)

<400> SEQUENCE: 5

aaacagagag agatagagaa agagaaagac agaggtgttt cccttagcta tggaaactct     60

ataagagaga tccagcttgc ctcctcttga gcagtcagca acagggtccc gtccttgaca    120

cctcagcctc tacaggactg agaagaagta aaaccgtttg ctggggctgg cctgactcac    180

cagctgcc atg cag cag ccc ttc aat tac cca tat ccc cag atc tac tgg      230
         Met Gln Gln Pro Phe Asn Tyr Pro Tyr Pro Gln Ile Tyr Trp
           1               5                  10

gtg gac agc agt gcc agc tct ccc tgg gcc cct cca ggc aca gtt ctt      278
Val Asp Ser Ser Ala Ser Ser Pro Trp Ala Pro Pro Gly Thr Val Leu
 15                  20                  25                  30

ccc tgt cca acc tct gtg ccc aga agg cct ggt caa agg agg cca cca      326
Pro Cys Pro Thr Ser Val Pro Arg Arg Pro Gly Gln Arg Arg Pro Pro
                35                  40                  45

cca cca ccg cca ccg cca cca cta cca cct ccg ccg ccg ccg cca cca      374
Pro Pro Pro Pro Pro Pro Pro Leu Pro Pro Pro Pro Pro Pro Pro Pro
            50                  55                  60

ctg cct cca cta ccg ctg cca ccc ctg aag aag aga ggg aac cac agc      422
Leu Pro Pro Leu Pro Leu Pro Pro Leu Lys Lys Arg Gly Asn His Ser
        65                  70                  75

aca ggc ctg tgt ctc ctt gtg atg ttt ttc atg gtt ctg gtt gcc ttg      470
Thr Gly Leu Cys Leu Leu Val Met Phe Phe Met Val Leu Val Ala Leu
    80                  85                  90

gta gga ttg ggc ctg ggg atg ttt cag ctc ttc cac cta cag aag gag      518
Val Gly Leu Gly Leu Gly Met Phe Gln Leu Phe His Leu Gln Lys Glu
 95                 100                 105                 110

ctg gca gaa ctc cga gag tct acc agc cag atg cac aca gca tca tct      566
Leu Ala Glu Leu Arg Glu Ser Thr Ser Gln Met His Thr Ala Ser Ser
                115                 120                 125

ttg gag aag caa ata ggc cac ccc agt cca ccc cct gaa aaa aag gag      614
Leu Glu Lys Gln Ile Gly His Pro Ser Pro Pro Pro Glu Lys Lys Glu
            130                 135                 140

ctg agg aaa gtg gcc cat tta aca ggc aag tcc aac tca agg tcc atg      662
Leu Arg Lys Val Ala His Leu Thr Gly Lys Ser Asn Ser Arg Ser Met
```

```
        145                 150                 155

cct ctg gaa tgg gaa gac acc tat gga att gtc ctg ctt tct gga gtg      710
Pro Leu Glu Trp Glu Asp Thr Tyr Gly Ile Val Leu Leu Ser Gly Val
    160                 165                 170

aag tat aag aag ggt ggc ctt gtg atc aat gaa act ggg ctg tac ttt      758
Lys Tyr Lys Lys Gly Gly Leu Val Ile Asn Glu Thr Gly Leu Tyr Phe
175                 180                 185                 190

gta tat tcc aaa gta tac ttc cgg ggt caa tct tgc aac aac ctg ccc      806
Val Tyr Ser Lys Val Tyr Phe Arg Gly Gln Ser Cys Asn Asn Leu Pro
                195                 200                 205

ctg agc cac aag gtc tac atg agg aac tct aag tat ccc cag gat ctg      854
Leu Ser His Lys Val Tyr Met Arg Asn Ser Lys Tyr Pro Gln Asp Leu
            210                 215                 220

gtg atg atg gag ggg aag atg atg agc tac tgc act act ggg cag atg      902
Val Met Met Glu Gly Lys Met Met Ser Tyr Cys Thr Thr Gly Gln Met
        225                 230                 235

tgg gcc cgc agc agc tac ctg ggg gca gtg ttc aat ctt acc agt gct      950
Trp Ala Arg Ser Ser Tyr Leu Gly Ala Val Phe Asn Leu Thr Ser Ala
    240                 245                 250

gat cat tta tat gtc aac gta tct gag ctc tct ctg gtc aat ttt gag      998
Asp His Leu Tyr Val Asn Val Ser Glu Leu Ser Leu Val Asn Phe Glu
255                 260                 265                 270

gaa tct cag acg ttt ttc ggc tta tat aag ctc taa gagaagcact          1044
Glu Ser Gln Thr Phe Phe Gly Leu Tyr Lys Leu
                275                 280

ttgggattct ttccattatg attctttgtt acaggcaccg agaatgttgt attcagtgag   1104

ggtcttctta catgcatttg aggtcaagta agaagacatg aaccaagtgg accttgagac   1164

cacagggttc aaaatgtctg tagctcctca actcacctaa tgtttatgag ccagacaaat   1224

ggaggaatat gacggaagaa catagaactc tgggctgcca tgtgaagagg gagaagcatg   1284

aaaaagcagc tacccaggtg ttctacactc atcttagtgc ctgagagtat ttaggcagat   1344

tgaaaaggac accttttaac tcacctctca aggtgggcct tgctacctca agggggactg   1404

tctttcagat acatggttgt gacctgagga tttaagggat ggaaaaggaa gactagaggc   1464

ttgcataata agctaaagag gctgaaagag gccaatgccc cactggcagc atcttcactt   1524

ctaaatgcat atcctgagcc atcggtgaaa ctaacagata agcaagagag atgttttggg   1584

gactcatttc attcctaaca cagcatgtgt atttccagtg ccaattgtag ggtgtgtgt    1644

gtgtgtgtgt gtgtgtgtgt atgactaaag agagaatgta gatattgtga agtacatatt   1704

aggaaaatat gggttgcatt tggtcaagat tttgaatgct tcctgacaat caactctaat   1764

agtgcttaaa aatcattgat tgtcagctac taatgatgtt ttcctataat ataataaata   1824

tttatgtaga tgtgcatttt tgtgaaatga aaacatgtaa taaaaagtat atgttaggat   1884

acaaat                                                               1890


<210> SEQ ID NO 6
<211> LENGTH: 281
<212> TYPE: PRT
<213> ORGANISM: Homo sapiens

<400> SEQUENCE: 6

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45
```

```
Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280


<210> SEQ ID NO 7
<211> LENGTH: 1623
<212> TYPE: DNA
<213> ORGANISM: Rattus norvegicus
<220> FEATURE:
<221> NAME/KEY: CDS
<222> LOCATION: (74)..(910)

<400> SEQUENCE: 7

tcagagtcct gtccttgaca cttcagtctc cacaagactg agaggaggaa accctttcct      60

ggggctgggt gcc atg cag cag ccc gtg aat tac cca tgt ccc cag atc        109
               Met Gln Gln Pro Val Asn Tyr Pro Cys Pro Gln Ile
                 1               5                  10

tac tgg gta gac agc agt gcc act tct cct tgg gct cct cca ggg tca       157
Tyr Trp Val Asp Ser Ser Ala Thr Ser Pro Trp Ala Pro Pro Gly Ser
         15                  20                  25

gtt ttt tct tgt cca tcc tct ggg cct aga ggg cca gga caa agg aga       205
Val Phe Ser Cys Pro Ser Ser Gly Pro Arg Gly Pro Gly Gln Arg Arg
     30                  35                  40

cca ccg cct cca cca cca cct cca tca cca cta cca ccg cct tcc caa       253
Pro Pro Pro Pro Pro Pro Pro Pro Ser Pro Leu Pro Pro Pro Ser Gln
 45                  50                  55                  60

cca ccc ccg ctg cct cca cta agc cct cta aag aag aag gac aac ata       301
Pro Pro Pro Leu Pro Pro Leu Ser Pro Leu Lys Lys Lys Asp Asn Ile
                 65                  70                  75

gag ctg tgg cta ccg gtg ata ttt ttc atg gtg ctg gtg gct ctg gtt       349
```

```
Glu Leu Trp Leu Pro Val Ile Phe Phe Met Val Leu Val Ala Leu Val
            80                  85                  90

gga atg ggg tta gga atg tat caa ctc ttt cat cta cag aag gaa ctg      397
Gly Met Gly Leu Gly Met Tyr Gln Leu Phe His Leu Gln Lys Glu Leu
        95                  100                 105

gca gaa ctc cgt gag ttc acc aac cac agc ctt aga gta tca tct ttt      445
Ala Glu Leu Arg Glu Phe Thr Asn His Ser Leu Arg Val Ser Ser Phe
    110                 115                 120

gaa aag caa ata gcc aac ccc agc aca ccc tct gaa acc aaa aag cca      493
Glu Lys Gln Ile Ala Asn Pro Ser Thr Pro Ser Glu Thr Lys Lys Pro
125                 130                 135                 140

agg agt gtg gcc cac tta aca ggg aac ccc cgc tca agg tcc atc cct      541
Arg Ser Val Ala His Leu Thr Gly Asn Pro Arg Ser Arg Ser Ile Pro
                145                 150                 155

ctg gaa tgg gaa gac aca tat gga act gct ttg atc tct gga gtg aag      589
Leu Glu Trp Glu Asp Thr Tyr Gly Thr Ala Leu Ile Ser Gly Val Lys
            160                 165                 170

tat aag aaa ggc ggc ctt gtg atc aat gag gct ggg ttg tac ttc gta      637
Tyr Lys Lys Gly Gly Leu Val Ile Asn Glu Ala Gly Leu Tyr Phe Val
        175                 180                 185

tat tcc aaa gta tac ttc cgg ggt cag tct tgc aac agc cag ccc cta      685
Tyr Ser Lys Val Tyr Phe Arg Gly Gln Ser Cys Asn Ser Gln Pro Leu
    190                 195                 200

agc cac aag gtc tat atg agg aac ttt aag tat cct ggg gat ctg gtg      733
Ser His Lys Val Tyr Met Arg Asn Phe Lys Tyr Pro Gly Asp Leu Val
205                 210                 215                 220

cta atg gag gag aag aag ttg aat tac tgc act act ggc cag ata tgg      781
Leu Met Glu Glu Lys Lys Leu Asn Tyr Cys Thr Thr Gly Gln Ile Trp
                225                 230                 235

gcc cac agc agc tac cta ggg gca gta ttt aat ctt acc gtt gct gac      829
Ala His Ser Ser Tyr Leu Gly Ala Val Phe Asn Leu Thr Val Ala Asp
            240                 245                 250

cat tta tat gtc aac ata tct caa ctc tct ctg atc aat ttt gag gaa      877
His Leu Tyr Val Asn Ile Ser Gln Leu Ser Leu Ile Asn Phe Glu Glu
        255                 260                 265

tct aag acc ttt ttt ggc tta tat aag ctt taa aggaaaaagc attttagaat    930
Ser Lys Thr Phe Phe Gly Leu Tyr Lys Leu
    270                 275

gatctattat tctttatcat ggatgccagg aatattgtct tcaatgagag tcttcttaag    990

accaattgag ccacaaagac cacaaggtcc aacaggtcag ctacccttca ttttctagag   1050

gtccatggag tggtccttaa tgcctgcatc atgagccaga tgggaagaag actgttcctg   1110

aggaacataa agttttgggc tgctgtgtgg caatgcagag gcaaagagaa ggaactgtct   1170

gatgttaaat ggccaagagc attttagcca ttgaagaaaa aaaaaacctt taaactcacc   1230

ttccagggtg ggtctacttg ctacctcaca ggaggccgtc ttttagacac atggttgtgg   1290

tatgactata caagggtgag aaaggatgct aggtttcatg gataagctag agactgaaaa   1350

aagccagtgt cccattggca tcatctttat ttttaactga tgttttctga gcccaccttt   1410

gatgctaaca gagaaataag aggggtgttt gaggcacaag tcattctcta catagcatgt   1470

gtacctccag tgcaatgatg tctgtgtgtg tttttatgta tgagagtaga gcgattctaa   1530

agagtcacat gagtacaacg cgtacattac ggagtacata ttagaaacgt atgtgttaca   1590

tttgatgcta gaatatctga atgtttcttg cta                                1623
```

<210> SEQ ID NO 8
<211> LENGTH: 278
<212> TYPE: PRT
<213> ORGANISM: Rattus norvegicus

<400> SEQUENCE: 8

```
Met Gln Gln Pro Val Asn Tyr Pro Cys Pro Gln Ile Tyr Trp Val Asp
  1               5                  10                  15

Ser Ser Ala Thr Ser Pro Trp Ala Pro Pro Gly Ser Val Phe Ser Cys
             20                  25                  30

Pro Ser Ser Gly Pro Arg Gly Pro Gly Gln Arg Arg Pro Pro Pro Pro
         35                  40                  45

Pro Pro Pro Pro Ser Pro Leu Pro Pro Pro Ser Gln Pro Pro Pro Leu
     50                  55                  60

Pro Pro Leu Ser Pro Leu Lys Lys Lys Asp Asn Ile Glu Leu Trp Leu
 65                  70                  75                  80

Pro Val Ile Phe Phe Met Val Leu Val Ala Leu Val Gly Met Gly Leu
                 85                  90                  95

Gly Met Tyr Gln Leu Phe His Leu Gln Lys Glu Leu Ala Glu Leu Arg
            100                 105                 110

Glu Phe Thr Asn His Ser Leu Arg Val Ser Ser Phe Glu Lys Gln Ile
        115                 120                 125

Ala Asn Pro Ser Thr Pro Ser Glu Thr Lys Lys Pro Arg Ser Val Ala
    130                 135                 140

His Leu Thr Gly Asn Pro Arg Ser Arg Ser Ile Pro Leu Glu Trp Glu
145                 150                 155                 160

Asp Thr Tyr Gly Thr Ala Leu Ile Ser Gly Val Lys Tyr Lys Lys Gly
                165                 170                 175

Gly Leu Val Ile Asn Glu Ala Gly Leu Tyr Phe Val Tyr Ser Lys Val
            180                 185                 190

Tyr Phe Arg Gly Gln Ser Cys Asn Ser Gln Pro Leu Ser His Lys Val
        195                 200                 205

Tyr Met Arg Asn Phe Lys Tyr Pro Gly Asp Leu Val Leu Met Glu Glu
    210                 215                 220

Lys Lys Leu Asn Tyr Cys Thr Thr Gly Gln Ile Trp Ala His Ser Ser
225                 230                 235                 240

Tyr Leu Gly Ala Val Phe Asn Leu Thr Val Ala Asp His Leu Tyr Val
                245                 250                 255

Asn Ile Ser Gln Leu Ser Leu Ile Asn Phe Glu Glu Ser Lys Thr Phe
            260                 265                 270

Phe Gly Leu Tyr Lys Leu
        275
```

<210> SEQ ID NO 9
<211> LENGTH: 1707
<212> TYPE: DNA
<213> ORGANISM: Mus musculus
<220> FEATURE:
<221> NAME/KEY: CDS
<222> LOCATION: (125)..(964)

<400> SEQUENCE: 9

```
ctgcggaaac tttataaaga aaacttagct tctctggagc agtcagcgtc agagttctgt     60

ccttgacacc tgagtctcct ccacaaggct gtgagaagga aaccctttcc tggggctggg    120

tgcc atg cag cag ccc atg aat tac cca tgt ccc cag atc ttc tgg gta     169
     Met Gln Gln Pro Met Asn Tyr Pro Cys Pro Gln Ile Phe Trp Val
       1               5                  10                  15

gac agc agt gcc act tca tct tgg gct cct cca ggg tca gtt ttt ccc     217
Asp Ser Ser Ala Thr Ser Ser Trp Ala Pro Pro Gly Ser Val Phe Pro
                 20                  25                  30
```

```
tgt cca tct tgt ggg cct aga ggg ccg gac caa agg aga ccg cca cct      265
Cys Pro Ser Cys Gly Pro Arg Gly Pro Asp Gln Arg Arg Pro Pro Pro
             35                  40                  45

cca cca cca cct gtg tca cca cta cca ccg cca tca caa cca ctc cca      313
Pro Pro Pro Pro Val Ser Pro Leu Pro Pro Pro Ser Gln Pro Leu Pro
         50                  55                  60

ctg ccg cca ctg acc cct cta aag aag aag gac cac aac aca aat ctg      361
Leu Pro Pro Leu Thr Pro Leu Lys Lys Lys Asp His Asn Thr Asn Leu
     65                  70                  75

tgg cta ccg gtg gta ttt ttc atg gtt ctg gtg gct ctg gtt gga atg      409
Trp Leu Pro Val Val Phe Phe Met Val Leu Val Ala Leu Val Gly Met
 80                  85                  90                  95

gga tta gga atg tat cag ctc ttc cac ctg cag aag gaa ctg gca gaa      457
Gly Leu Gly Met Tyr Gln Leu Phe His Leu Gln Lys Glu Leu Ala Glu
                100                 105                 110

ctc cgt gag ttc acc aac caa agc ctt aaa gta tca tct ttt gaa aag      505
Leu Arg Glu Phe Thr Asn Gln Ser Leu Lys Val Ser Ser Phe Glu Lys
            115                 120                 125

caa ata gcc aac ccc agt aca ccc tct gaa aaa aaa gag ccg agg agt      553
Gln Ile Ala Asn Pro Ser Thr Pro Ser Glu Lys Lys Glu Pro Arg Ser
        130                 135                 140

gtg gcc cat tta aca ggg aac ccc cac tca agg tcc atc cct ctg gaa      601
Val Ala His Leu Thr Gly Asn Pro His Ser Arg Ser Ile Pro Leu Glu
    145                 150                 155

tgg gaa gac aca tat gga acc gct ctg atc tct gga gtg aag tat aag      649
Trp Glu Asp Thr Tyr Gly Thr Ala Leu Ile Ser Gly Val Lys Tyr Lys
160                 165                 170                 175

aaa ggt ggc ctt gtg atc aac gaa act ggg ttg tac ttc gtg tat tcc      697
Lys Gly Gly Leu Val Ile Asn Glu Thr Gly Leu Tyr Phe Val Tyr Ser
                180                 185                 190

aaa gta tac ttc cgg ggt cag tct tgc aac aac cag ccc cta aac cac      745
Lys Val Tyr Phe Arg Gly Gln Ser Cys Asn Asn Gln Pro Leu Asn His
            195                 200                 205

aag gtc tat atg agg aac tct aag tat cct gag gat ctg gtg cta atg      793
Lys Val Tyr Met Arg Asn Ser Lys Tyr Pro Glu Asp Leu Val Leu Met
        210                 215                 220

gag gag aag agg ttg aac tac tgc act act gga cag ata tgg gcc cac      841
Glu Glu Lys Arg Leu Asn Tyr Cys Thr Thr Gly Gln Ile Trp Ala His
    225                 230                 235

agc agc tac ctg ggg gca gta ttc aat ctt acc agt gct gac cat tta      889
Ser Ser Tyr Leu Gly Ala Val Phe Asn Leu Thr Ser Ala Asp His Leu
240                 245                 250                 255

tat gtc aac ata tct caa ctc tct ctg atc aat ttt gag gaa tct aag      937
Tyr Val Asn Ile Ser Gln Leu Ser Leu Ile Asn Phe Glu Glu Ser Lys
                260                 265                 270

acc ttt ttc ggc ttg tat aag ctt taa aagaaaaagc attttaaaat            984
Thr Phe Phe Gly Leu Tyr Lys Leu
            275                 280

gatctactat tctttatcat gggcaccagg aatattgtct tgaatgagag tcttcttaag   1044

acctattgag attaattaag actacatgag ccacaaagac ctcatgaccg caaggtccaa   1104

caggtcagct atccttcatt ttctcgaggt ccatggagtg gtccttaatg cctgcatcat   1164

gagccagatg gaaggaggtc tgtgactgag ggacataaag ctttgggctg ctgtgtgaca   1224

atgcagaggc acagagaaag aactgtctga tgttaaatgg ccaagagaat tttaaccatt   1284

gaagaagaca cctttacact cacttccagg gtgggtctac ttactacctc acagaggccg   1344

tttttgagac atagttgtgg tatgaatata caagggtgag aaaggaggct catttgactg   1404

ataagctaga gactgaaaaa aagacagtgt ctcattggca ccatctttac tgttacctaa   1464
```

```
tgttttctga gccgaccttt gatcctaacg gagaagtaag agggatgttt gaggcacaaa   1524

tcattctcta catagcatgc atacctccag tgcaatgatg tctgtgtgtt tgtatgtatg   1584

agagcaaaca gattctaagg agtcatataa ataaaatatg tacattatgg agtacatatt   1644

agaaacctgt tacatttgat gctagatatc tgaatgtttc ttggcaataa actctaatag   1704

tct                                                                 1707
```

<210> SEQ ID NO 10
<211> LENGTH: 279
<212> TYPE: PRT
<213> ORGANISM: Mus musculus

<400> SEQUENCE: 10

```
Met Gln Gln Pro Met Asn Tyr Pro Cys Pro Gln Ile Phe Trp Val Asp
  1               5                  10                  15

Ser Ser Ala Thr Ser Ser Trp Ala Pro Pro Gly Ser Val Phe Pro Cys
             20                  25                  30

Pro Ser Cys Gly Pro Arg Gly Pro Asp Gln Arg Arg Pro Pro Pro Pro
         35                  40                  45

Pro Pro Pro Val Ser Pro Leu Pro Pro Pro Ser Gln Pro Leu Pro Leu
     50                  55                  60

Pro Pro Leu Thr Pro Leu Lys Lys Lys Asp His Asn Thr Asn Leu Trp
 65                  70                  75                  80

Leu Pro Val Val Phe Phe Met Val Leu Val Ala Leu Val Gly Met Gly
                 85                  90                  95

Leu Gly Met Tyr Gln Leu Phe His Leu Gln Lys Glu Leu Ala Glu Leu
            100                 105                 110

Arg Glu Phe Thr Asn Gln Ser Leu Lys Val Ser Ser Phe Glu Lys Gln
        115                 120                 125

Ile Ala Asn Pro Ser Thr Pro Ser Glu Lys Lys Glu Pro Arg Ser Val
    130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
                165                 170                 175

Gly Gly Leu Val Ile Asn Glu Thr Gly Leu Tyr Phe Val Tyr Ser Lys
            180                 185                 190

Val Tyr Phe Arg Gly Gln Ser Cys Asn Asn Gln Pro Leu Asn His Lys
        195                 200                 205

Val Tyr Met Arg Asn Ser Lys Tyr Pro Glu Asp Leu Val Leu Met Glu
    210                 215                 220

Glu Lys Arg Leu Asn Tyr Cys Thr Thr Gly Gln Ile Trp Ala His Ser
225                 230                 235                 240

Ser Tyr Leu Gly Ala Val Phe Asn Leu Thr Ser Ala Asp His Leu Tyr
                245                 250                 255

Val Asn Ile Ser Gln Leu Ser Leu Ile Asn Phe Glu Glu Ser Lys Thr
            260                 265                 270

Phe Phe Gly Leu Tyr Lys Leu
        275
```

<210> SEQ ID NO 11
<211> LENGTH: 2534
<212> TYPE: DNA
<213> ORGANISM: Homo sapiens
<220> FEATURE:
<221> NAME/KEY: CDS
<222> LOCATION: (195)..(1202)

```
<400> SEQUENCE: 11

gacgcttctg gggagtgagg gaagcggttt acgagtgact tggctggagc ctcaggggcg      60

ggcactggca cggaacacac cctgaggcca gccctggctg cccaggcgga gctgcctctt     120

ctcccgcggg ttggtggacc cgctcagtac ggagttgggg aagctctttc acttcggagg     180

attgctcaac aacc atg ctg ggc atc tgg acc ctc cta cct ctg gtt ctt       230
                Met Leu Gly Ile Trp Thr Leu Leu Pro Leu Val Leu
                1               5                   10

acg tct gtt gct aga tta tcg tcc aaa agt gtt aat gcc caa gtg act       278
Thr Ser Val Ala Arg Leu Ser Ser Lys Ser Val Asn Ala Gln Val Thr
        15                  20                  25

gac atc aac tcc aag gga ttg gaa ttg agg aag act gtt act aca gtt       326
Asp Ile Asn Ser Lys Gly Leu Glu Leu Arg Lys Thr Val Thr Thr Val
    30                  35                  40

gag act cag aac ttg gaa ggc ctg cat cat gat ggc caa ttc tgc cat       374
Glu Thr Gln Asn Leu Glu Gly Leu His His Asp Gly Gln Phe Cys His
45                  50                  55                  60

aag ccc tgt cct cca ggt gaa agg aaa gct agg gac tgc aca gtc aat       422
Lys Pro Cys Pro Pro Gly Glu Arg Lys Ala Arg Asp Cys Thr Val Asn
                65                  70                  75

ggg gat gaa cca gac tgc gtg ccc tgc caa gaa ggg aag gag tac aca       470
Gly Asp Glu Pro Asp Cys Val Pro Cys Gln Glu Gly Lys Glu Tyr Thr
            80                  85                  90

gac aaa gcc cat ttt tct tcc aaa tgc aga aga tgt aga ttg tgt gat       518
Asp Lys Ala His Phe Ser Ser Lys Cys Arg Arg Cys Arg Leu Cys Asp
        95                  100                 105

gaa gga cat ggc tta gaa gtg gaa ata aac tgc acc cgg acc cag aat       566
Glu Gly His Gly Leu Glu Val Glu Ile Asn Cys Thr Arg Thr Gln Asn
    110                 115                 120

acc aag tgc aga tgt aaa cca aac ttt ttt tgt aac tct act gta tgt       614
Thr Lys Cys Arg Cys Lys Pro Asn Phe Phe Cys Asn Ser Thr Val Cys
125                 130                 135                 140

gaa cac tgt gac cct tgc acc aaa tgt gaa cat gga atc atc aag gaa       662
Glu His Cys Asp Pro Cys Thr Lys Cys Glu His Gly Ile Ile Lys Glu
                145                 150                 155

tgc aca ctc acc agc aac acc aag tgc aaa gag gaa gga tcc aga tct       710
Cys Thr Leu Thr Ser Asn Thr Lys Cys Lys Glu Glu Gly Ser Arg Ser
            160                 165                 170

aac ttg ggg tgg ctt tgt ctt ctt ctt ttg cca att cca cta att gtt       758
Asn Leu Gly Trp Leu Cys Leu Leu Leu Leu Pro Ile Pro Leu Ile Val
        175                 180                 185

tgg gtg aag aga aag gaa gta cag aaa aca tgc aga aag cac aga aag       806
Trp Val Lys Arg Lys Glu Val Gln Lys Thr Cys Arg Lys His Arg Lys
    190                 195                 200

gaa aac caa ggt tct cat gaa tct cca acc tta aat cct gaa aca gtg       854
Glu Asn Gln Gly Ser His Glu Ser Pro Thr Leu Asn Pro Glu Thr Val
205                 210                 215                 220

gca ata aat tta tct gat gtt gac ttg agt aaa tat atc acc act att       902
Ala Ile Asn Leu Ser Asp Val Asp Leu Ser Lys Tyr Ile Thr Thr Ile
                225                 230                 235

gct gga gtc atg aca cta agt caa gtt aaa ggc ttt gtt cga aag aat       950
Ala Gly Val Met Thr Leu Ser Gln Val Lys Gly Phe Val Arg Lys Asn
            240                 245                 250

ggt gtc aat gaa gcc aaa ata gat gag atc aag aat gac aat gtc caa       998
Gly Val Asn Glu Ala Lys Ile Asp Glu Ile Lys Asn Asp Asn Val Gln
        255                 260                 265

gac aca gca gaa cag aaa gtt caa ctg ctt cgt aat tgg cat caa ctt      1046
Asp Thr Ala Glu Gln Lys Val Gln Leu Leu Arg Asn Trp His Gln Leu
    270                 275                 280
```

```
cat gga aag aaa gaa gcg tat gac aca ttg att aaa gat ctc aaa aaa     1094
His Gly Lys Lys Glu Ala Tyr Asp Thr Leu Ile Lys Asp Leu Lys Lys
285                 290                 295                 300

gcc aat ctt tgt act ctt gca gag aaa att cag act atc atc ctc aag     1142
Ala Asn Leu Cys Thr Leu Ala Glu Lys Ile Gln Thr Ile Ile Leu Lys
                305                 310                 315

gac att act agt gac tca gaa aat tca aac ttc aga aat gaa atc caa     1190
Asp Ile Thr Ser Asp Ser Glu Asn Ser Asn Phe Arg Asn Glu Ile Gln
            320                 325                 330

agc ttg gtc tag agtgaaaaac aacaaattca gttctgagta tatgcaatta         1242
Ser Leu Val
        335

gtgtttgaaa agattcttaa tagctggctg taaatactgc ttggtttttt actgggtaca   1302

ttttatcatt tattagcgct gaagagccaa catatttgta gatttttaat atctcatgat   1362

tctgcctcca aggatgttta aaatctagtt gggaaaacaa acttcatcaa gagtaaatgc   1422

agtggcatgc taagtaccca aataggagtg tatgcagagg atgaaagatt aagattatgc   1482

tctggcatct aacatatgat tctgtagtat gaatgtaatc agtgtatgtt agtacaaatg   1542

tctatccaca ggctaacccc actctatgaa tcaatagaag aagctatgac cttttgctga   1602

aatatcagtt actgaacagg caggccactt tgcctctaaa ttacctctga taattctaga   1662

gattttacca tatttctaaa ctttgtttat aactctgaga agatcatatt tatgtaaagt   1722

atatgtattt gagtgcagaa tttaaataag gctctacctc aaagaccttt gcacagttta   1782

ttggtgtcat attatacaat atttcaattg tgaattcaca tagaaaacat taaattataa   1842

tgtttgacta ttatatatgt gtatgcattt tactggctca aaactaccta cttctttctc   1902

aggcatcaaa agcattttga gcaggagagt attactagag ctttgccacc tctccatttt   1962

tgccttggtg ctcatcttaa tggcctaatg cacccccaaa catggaaata tcaccaaaaa   2022

atacttaata gtccaccaaa aggcaagact gcccttagaa attctagcct ggtttggaga   2082

tactaactgc tctcagagaa agtagctttg tgacatgtca tgaacccatg tttgcaatca   2142

aagatgataa aatagattct tatttttccc ccacccccga aaatgttcaa taatgtccca   2202

tgtaaaacct gctacaaatg gcagcttata catagcaatg gtaaaatcat catctggatt   2262

taggaattgc tcttgtcata ccctcaagtt tctaagattt aagattctcc ttactactat   2322

cctacgttta aatatctttg aaagtttgta ttaaatgtga attttaagaa ataatattta   2382

tatttctgta aatgtaaact gtgaagatag ttataaactg aagcagatac ctggaaccac   2442

ctaaagaact tccatttatg gaggattttt ttgccccttg tgtttggaat tataaaatat   2502

aggtaaaagt acgtaattaa ataatgtttt tg                                 2534


<210> SEQ ID NO 12
<211> LENGTH: 335
<212> TYPE: PRT
<213> ORGANISM: Homo sapiens

<400> SEQUENCE: 12

Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
             20                  25                  30

Lys Gly Leu Glu Leu Arg Lys Thr Val Thr Thr Val Glu Thr Gln Asn
         35                  40                  45

Leu Glu Gly Leu His His Asp Gly Gln Phe Cys His Lys Pro Cys Pro
     50                  55                  60
```

```
Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335


<210> SEQ ID NO 13
<211> LENGTH: 1642
<212> TYPE: DNA
<213> ORGANISM: Homo sapiens
<220> FEATURE:
<221> NAME/KEY: CDS
<222> LOCATION: (130)..(756)

<400> SEQUENCE: 13

ctctaaaggt tcgggggtgg aatccttggg ccgctgggca agcggcgaga cctggccagg      60

gccagcgagc cgaggacaga gggcgcacgg agggccgggc cgcagccccg gccgcttgca     120

gaccccgcc atg gac ccg ttc ctg gtg ctg ctg cac tcg gtg tcg tcc agc     171
          Met Asp Pro Phe Leu Val Leu Leu His Ser Val Ser Ser Ser
            1               5                  10

ctg tcg agc agc gag ctg acc gag ctc aag ttc cta tgc ctc ggg cgc       219
Leu Ser Ser Ser Glu Leu Thr Glu Leu Lys Phe Leu Cys Leu Gly Arg
 15                  20                  25                  30

gtg ggc aag cgc aag ctg gag cgc gtg cag agc ggc cta gac ctc ttc       267
Val Gly Lys Arg Lys Leu Glu Arg Val Gln Ser Gly Leu Asp Leu Phe
                 35                  40                  45

tcc atg ctg ctg gag cag aac gac ctg gag ccc ggg cac acc gag ctc       315
```

```
Ser Met Leu Leu Glu Gln Asn Asp Leu Glu Pro Gly His Thr Glu Leu
            50                  55                  60

ctg cgc gag ctg ctc gcc tcc ctg cgg cgc cac gac ctg ctg cgg cgc      363
Leu Arg Glu Leu Leu Ala Ser Leu Arg Arg His Asp Leu Leu Arg Arg
        65                  70                  75

gtc gac gac ttc gag gcg ggg gcg gcg gcc ggg gcc gcg cct ggg gaa      411
Val Asp Asp Phe Glu Ala Gly Ala Ala Ala Gly Ala Ala Pro Gly Glu
    80                  85                  90

gaa gac ctg tgt gca gca ttt aac gtc ata tgt gat aat gtg ggg aaa      459
Glu Asp Leu Cys Ala Ala Phe Asn Val Ile Cys Asp Asn Val Gly Lys
 95                 100                 105                 110

gat tgg aga agg ctg gct cgt cag ctc aaa gtc tca gac acc aag atc      507
Asp Trp Arg Arg Leu Ala Arg Gln Leu Lys Val Ser Asp Thr Lys Ile
                115                 120                 125

gac agc atc gag gac aga tac ccc cgc aac ctg aca gag cgt gtg cgg      555
Asp Ser Ile Glu Asp Arg Tyr Pro Arg Asn Leu Thr Glu Arg Val Arg
            130                 135                 140

gag tca ctg aga atc tgg aag aac aca gag aag gag aac gca aca gtg      603
Glu Ser Leu Arg Ile Trp Lys Asn Thr Glu Lys Glu Asn Ala Thr Val
        145                 150                 155

gcc cac ctg gtg ggg gct ctc agg tcc tgc cag atg aac ctg gtg gct      651
Ala His Leu Val Gly Ala Leu Arg Ser Cys Gln Met Asn Leu Val Ala
    160                 165                 170

gac ctg gta caa gag gtt cag cag gcc cgt gac ctc cag aac agg agt      699
Asp Leu Val Gln Glu Val Gln Gln Ala Arg Asp Leu Gln Asn Arg Ser
175                 180                 185                 190

ggg gcc atg tcc ccg atg tca tgg aac tca gac gca tct acc tcc gaa      747
Gly Ala Met Ser Pro Met Ser Trp Asn Ser Asp Ala Ser Thr Ser Glu
                195                 200                 205

gcg tcc tga tgggccgctg ctttgcgctg gtggaccaca ggcatctaca              796
Ala Ser

cagcctggac tttggttctc tccaggaagg tagcccagca ctgtgaagac ccagcaggaa    856

gccaggctga gtgagccaca gaccacctgc ttctgaactc aagctgcgtt tattaatgcc    916

tctcccgcac caggccgggc ttgggccctg cacagatatt tccatttctt cctcactatg    976

acactgagca agatcttgtc tccactaaat gagctcctgc gggagtagtt ggaaagttgg   1036

aaccgtgtcc agcacagaag gaatctgtgc agatgagcag tcacactgtt actccacagc   1096

ggaggagacc agctcagagg cccaggaatc ggagcgaagc agagaggtgg agaactggga   1156

tttgaacccc cgccatcctt caccagagcc catgctcaac cactgtggcg ttctgctgcc   1216

cctgcagttg gcagaaagga tgttttgtcc catttccttg gaggccaccg ggacagacct   1276

ggacactagg gtcaggcggg gtgctgtggt ggggagaggc atggctgggg tgggggtggg   1336

gagacctggt tggccgtggt ccagctcttg gcccctgtgt gagttgagtc tcctctctga   1396

gactgctaag taggggcagt gatggttgcc aggacgaatt gagataatat ctgtgaggtg   1456

ctgatgagtg attgacacac agcactctct aaatcttcct tgtgaggatt atgggtcctg   1516

caattctaca gtttcttact gttttgtatc aaaatcacta tctttctgat aacagaattg   1576

ccaaggcagc gggatctcgt atctttaaaa agcagtcctc ttattcctaa ggtaatccta   1636

ttaaaa                                                              1642


<210> SEQ ID NO 14
<211> LENGTH: 208
<212> TYPE: PRT
<213> ORGANISM: Homo sapiens

<400> SEQUENCE: 14
```

```
Met Asp Pro Phe Leu Val Leu Leu His Ser Val Ser Ser Ser Leu Ser
  1               5                  10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Glu Pro Gly His Thr Glu Leu Leu Arg
    50                  55                  60

Glu Leu Leu Ala Ser Leu Arg Arg His Asp Leu Leu Arg Arg Val Asp
 65                  70                  75                  80

Asp Phe Glu Ala Gly Ala Ala Ala Gly Ala Ala Pro Gly Glu Glu Asp
                 85                  90                  95

Leu Cys Ala Ala Phe Asn Val Ile Cys Asp Asn Val Gly Lys Asp Trp
            100                 105                 110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
    130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
            180                 185                 190

Met Ser Pro Met Ser Trp Asn Ser Asp Ala Ser Thr Ser Glu Ala Ser
        195                 200                 205
```

<210> SEQ ID NO 15
<211> LENGTH: 1883
<212> TYPE: DNA
<213> ORGANISM: Homo sapiens
<220> FEATURE:
<221> NAME/KEY: CDS
<222> LOCATION: (257)..(1747)

<400> SEQUENCE: 15

```
tgaaggctgg ttgttcagac tgagcttcct gcctgcctgt accccgccaa cagcttcaga      60

agaaggtgac tggtggctgc ctgaggaata ccagtgggca agagaattag catttctgga     120

gcatctgctg tctgagcagc ccctgggtgc gtccactttc tgggcacgtg aggttgggcc     180

ttggccgcct gagcccttga gttggtcact tgaaccttgg gaatattgag attatattct     240

cctgcctttt aaaaag atg gac ttc agc aga aat ctt tat gat att ggg gaa     292
                  Met Asp Phe Ser Arg Asn Leu Tyr Asp Ile Gly Glu
                    1               5                  10

caa ctg gac agt gaa gat ctg gcc tcc ctc aag ttc ctg agc ctg gac       340
Gln Leu Asp Ser Glu Asp Leu Ala Ser Leu Lys Phe Leu Ser Leu Asp
        15                  20                  25

tac att ccg caa agg aag caa gaa ccc atc aag gat gcc ttg atg tta       388
Tyr Ile Pro Gln Arg Lys Gln Glu Pro Ile Lys Asp Ala Leu Met Leu
    30                  35                  40

ttc cag aga ctc cag gaa aag aga atg ttg gag gaa agc aat ctg tcc       436
Phe Gln Arg Leu Gln Glu Lys Arg Met Leu Glu Glu Ser Asn Leu Ser
 45                  50                  55                  60

ttc ctg aag gag ctg ctc ttc cga att aat aga ctg gat ttg ctg att       484
Phe Leu Lys Glu Leu Leu Phe Arg Ile Asn Arg Leu Asp Leu Leu Ile
                 65                  70                  75

acc tac cta aac act aga aag gag gag atg gaa agg gaa ctt cag aca       532
Thr Tyr Leu Asn Thr Arg Lys Glu Glu Met Glu Arg Glu Leu Gln Thr
```

```
            80                  85                  90

cca ggc agg gct caa att tct gcc tac agg ttc cac ttc tgc cgc atg      580
Pro Gly Arg Ala Gln Ile Ser Ala Tyr Arg Phe His Phe Cys Arg Met
        95                  100                 105

agc tgg gct gaa gca aac agc cag tgc cag aca cag tct gta cct ttc      628
Ser Trp Ala Glu Ala Asn Ser Gln Cys Gln Thr Gln Ser Val Pro Phe
    110                 115                 120

tgg cgg agg gtc gat cat cta tta ata agg gtc atg ctc tat cag att      676
Trp Arg Arg Val Asp His Leu Leu Ile Arg Val Met Leu Tyr Gln Ile
125                 130                 135                 140

tca gaa gaa gtg agc aga tca gaa ttg agg tct ttt aag ttt ctt ttg      724
Ser Glu Glu Val Ser Arg Ser Glu Leu Arg Ser Phe Lys Phe Leu Leu
                145                 150                 155

caa gag gaa atc tcc aaa tgc aaa ctg gat gat gac atg aac ctg ctg      772
Gln Glu Glu Ile Ser Lys Cys Lys Leu Asp Asp Asp Met Asn Leu Leu
            160                 165                 170

gat att ttc ata gag atg gag aag agg gtc atc ctg gga gaa gga aag      820
Asp Ile Phe Ile Glu Met Glu Lys Arg Val Ile Leu Gly Glu Gly Lys
        175                 180                 185

ttg gac atc ctg aaa aga gtc tgt gcc caa atc aac aag agc ctg ctg      868
Leu Asp Ile Leu Lys Arg Val Cys Ala Gln Ile Asn Lys Ser Leu Leu
    190                 195                 200

aag ata atc aac gac tat gaa gaa ttc agc aaa ggg gag gag ttg tgt      916
Lys Ile Ile Asn Asp Tyr Glu Glu Phe Ser Lys Gly Glu Glu Leu Cys
205                 210                 215                 220

ggg gta atg aca atc tcg gac tct cca aga gaa cag gat agt gaa tca      964
Gly Val Met Thr Ile Ser Asp Ser Pro Arg Glu Gln Asp Ser Glu Ser
                225                 230                 235

cag act ttg gac aaa gtt tac caa atg aaa agc aaa cct cgg gga tac     1012
Gln Thr Leu Asp Lys Val Tyr Gln Met Lys Ser Lys Pro Arg Gly Tyr
            240                 245                 250

tgt ctg atc atc aac aat cac aat ttt gca aaa gca cgg gag aaa gtg     1060
Cys Leu Ile Ile Asn Asn His Asn Phe Ala Lys Ala Arg Glu Lys Val
        255                 260                 265

ccc aaa ctt cac agc att agg gac agg aat gga aca cac ttg gat gca     1108
Pro Lys Leu His Ser Ile Arg Asp Arg Asn Gly Thr His Leu Asp Ala
    270                 275                 280

ggg gct ttg acc acg acc ttt gaa gag ctt cat ttt gag atc aag ccc     1156
Gly Ala Leu Thr Thr Thr Phe Glu Glu Leu His Phe Glu Ile Lys Pro
285                 290                 295                 300

cac cat gac tgc aca gta gag caa atc tat gag att ttg aaa atc tac     1204
His His Asp Cys Thr Val Glu Gln Ile Tyr Glu Ile Leu Lys Ile Tyr
                305                 310                 315

caa ctc atg gac cac agt aac atg gac tgc ttc atc tgc tgt atc ctc     1252
Gln Leu Met Asp His Ser Asn Met Asp Cys Phe Ile Cys Cys Ile Leu
            320                 325                 330

tcc cat gga gac aag ggc atc atc tat ggc act gat gga cag gag gcc     1300
Ser His Gly Asp Lys Gly Ile Ile Tyr Gly Thr Asp Gly Gln Glu Ala
        335                 340                 345

ccc atc tat gag ctg aca tct cag ttc act ggt ttg aag tgc cct tcc     1348
Pro Ile Tyr Glu Leu Thr Ser Gln Phe Thr Gly Leu Lys Cys Pro Ser
    350                 355                 360

ctt gct gga aaa ccc aaa gtg ttt ttt att cag gct tgt cag ggg gat     1396
Leu Ala Gly Lys Pro Lys Val Phe Phe Ile Gln Ala Cys Gln Gly Asp
365                 370                 375                 380

aac tac cag aaa ggt ata cct gtt gag act gat tca gag gag caa ccc     1444
Asn Tyr Gln Lys Gly Ile Pro Val Glu Thr Asp Ser Glu Glu Gln Pro
                385                 390                 395

tat tta gaa atg gat tta tca tca cct caa acg aga tat atc ccg gat     1492
Tyr Leu Glu Met Asp Leu Ser Ser Pro Gln Thr Arg Tyr Ile Pro Asp
```

```
            400                 405                 410

gag gct gac ttt ctg ctg ggg atg gcc act gtg aat aac tgt gtt tcc      1540
Glu Ala Asp Phe Leu Leu Gly Met Ala Thr Val Asn Asn Cys Val Ser
        415                 420                 425

tac cga aac cct gca gag gga acc tgg tac atc cag tca ctt tgc cag      1588
Tyr Arg Asn Pro Ala Glu Gly Thr Trp Tyr Ile Gln Ser Leu Cys Gln
    430                 435                 440

agc ctg aga gag cga tgt cct cga ggc gat gat att ctc acc atc ctg      1636
Ser Leu Arg Glu Arg Cys Pro Arg Gly Asp Asp Ile Leu Thr Ile Leu
445                 450                 455                 460

act gaa gtg aac tat gaa gta agc aac aag gat gac aag aaa aac atg      1684
Thr Glu Val Asn Tyr Glu Val Ser Asn Lys Asp Asp Lys Lys Asn Met
                465                 470                 475

ggg aaa cag atg cct cag cct act ttc aca cta aga aaa aaa ctt gtc      1732
Gly Lys Gln Met Pro Gln Pro Thr Phe Thr Leu Arg Lys Lys Leu Val
            480                 485                 490

ttc cct tct gat tga tggtgctatt ttgtttgttt tgttttgttt tgttttttg      1787
Phe Pro Ser Asp
        495

agacagaatc tcgctctgtc gcccaggctg gagtgcagtg gcgtgatctc ggctcaccgc   1847

aagctccgcc tcccgggttc aggccattct cctgct                             1883


<210> SEQ ID NO 16
<211> LENGTH: 496
<212> TYPE: PRT
<213> ORGANISM: Homo sapiens

<400> SEQUENCE: 16

Met Asp Phe Ser Arg Asn Leu Tyr Asp Ile Gly Glu Gln Leu Asp Ser
  1               5                  10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
    130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190

Lys Arg Val Cys Ala Gln Ile Asn Lys Ser Leu Leu Lys Ile Ile Asn
        195                 200                 205

Asp Tyr Glu Glu Phe Ser Lys Gly Glu Glu Leu Cys Gly Val Met Thr
    210                 215                 220
```

```
Ile Ser Asp Ser Pro Arg Glu Gln Asp Ser Glu Ser Gln Thr Leu Asp
225                 230                 235                 240

Lys Val Tyr Gln Met Lys Ser Lys Pro Arg Gly Tyr Cys Leu Ile Ile
                245                 250                 255

Asn Asn His Asn Phe Ala Lys Ala Arg Glu Lys Val Pro Lys Leu His
            260                 265                 270

Ser Ile Arg Asp Arg Asn Gly Thr His Leu Asp Ala Gly Ala Leu Thr
        275                 280                 285

Thr Thr Phe Glu Glu Leu His Phe Glu Ile Lys Pro His His Asp Cys
    290                 295                 300

Thr Val Glu Gln Ile Tyr Glu Ile Leu Lys Ile Tyr Gln Leu Met Asp
305                 310                 315                 320

His Ser Asn Met Asp Cys Phe Ile Cys Cys Ile Leu Ser His Gly Asp
                325                 330                 335

Lys Gly Ile Ile Tyr Gly Thr Asp Gly Gln Glu Ala Pro Ile Tyr Glu
            340                 345                 350

Leu Thr Ser Gln Phe Thr Gly Leu Lys Cys Pro Ser Leu Ala Gly Lys
        355                 360                 365

Pro Lys Val Phe Phe Ile Gln Ala Cys Gln Gly Asp Asn Tyr Gln Lys
    370                 375                 380

Gly Ile Pro Val Glu Thr Asp Ser Glu Glu Gln Pro Tyr Leu Glu Met
385                 390                 395                 400

Asp Leu Ser Ser Pro Gln Thr Arg Tyr Ile Pro Asp Glu Ala Asp Phe
                405                 410                 415

Leu Leu Gly Met Ala Thr Val Asn Asn Cys Val Ser Tyr Arg Asn Pro
            420                 425                 430

Ala Glu Gly Thr Trp Tyr Ile Gln Ser Leu Cys Gln Ser Leu Arg Glu
        435                 440                 445

Arg Cys Pro Arg Gly Asp Asp Ile Leu Thr Ile Leu Thr Glu Val Asn
    450                 455                 460

Tyr Glu Val Ser Asn Lys Asp Asp Lys Lys Asn Met Gly Lys Gln Met
465                 470                 475                 480

Pro Gln Pro Thr Phe Thr Leu Arg Lys Lys Leu Val Phe Pro Ser Asp
                485                 490                 495


<210> SEQ ID NO 17
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 17

atg agc act gaa agc atg atc cgg gac gtg gag ctg gcc gag gag gcg       48
Met Ser Thr Glu Ser Met Ile Arg Asp Val Glu Leu Ala Glu Glu Ala
  1               5                  10                  15

ctc ccc aag aag aca ggg ggg ccc cag ggc tcc agg cgg tgc ttg ttc       96
Leu Pro Lys Lys Thr Gly Gly Pro Gln Gly Ser Arg Arg Cys Leu Phe
             20                  25                  30

ctc agc ctc ttc tcc ttc ctg atc gtg gca ggc gcc acc acg ctc ttc      144
Leu Ser Leu Phe Ser Phe Leu Ile Val Ala Gly Ala Thr Thr Leu Phe
         35                  40                  45

tgc ctg ctg cac ttt gga gtg atc ggc ccc cag agg gaa gag ttc ccc      192
Cys Leu Leu His Phe Gly Val Ile Gly Pro Gln Arg Glu Glu Phe Pro
     50                  55                  60

agg gac ctc tct cta atc agc cct ctg gcc cag gca gtc aga tca tct      240
Arg Asp Leu Ser Leu Ile Ser Pro Leu Ala Gln Ala Val Arg Ser Ser
```

```
 65                 70                 75                 80

tct cga acc ccg agt gac aag cct gta gcc cat gtt gta gca aac cct      288
Ser Arg Thr Pro Ser Asp Lys Pro Val Ala His Val Val Ala Asn Pro
                85                 90                 95

caa gct gag ggg cag ctc cag tgg ctg aac cgc cgg gcc aat gcc ctc      336
Gln Ala Glu Gly Gln Leu Gln Trp Leu Asn Arg Arg Ala Asn Ala Leu
            100                105                110

ctg gcc aat ggc gtg gag ctg aga gat aac cag ctg gtg gtg cca tca      384
Leu Ala Asn Gly Val Glu Leu Arg Asp Asn Gln Leu Val Val Pro Ser
        115                120                125

gag ggc ctg tac ctc atc tac tcc cag gtc ctc ttc aag ggc caa ggc      432
Glu Gly Leu Tyr Leu Ile Tyr Ser Gln Val Leu Phe Lys Gly Gln Gly
    130                135                140

tgc ccc tcc acc cat gtg ctc ctc acc cac acc atc agc cgc atc gcc      480
Cys Pro Ser Thr His Val Leu Leu Thr His Thr Ile Ser Arg Ile Ala
145                150                155                160

gtc tcc tac cag acc aag gtc aac ctc ctc tct gcc atc aag agc ccc      528
Val Ser Tyr Gln Thr Lys Val Asn Leu Leu Ser Ala Ile Lys Ser Pro
                165                170                175

tgc cag agg gag acc cca gag ggg gct gag gcc aag ccc tgg tat gag      576
Cys Gln Arg Glu Thr Pro Glu Gly Ala Glu Ala Lys Pro Trp Tyr Glu
            180                185                190

ccc atc tat ctg gga ggg gtc ttc cag ctg gag aag ggt gac cga ctc      624
Pro Ile Tyr Leu Gly Gly Val Phe Gln Leu Glu Lys Gly Asp Arg Leu
        195                200                205

agc gct gag atc aat cgg ccc gac tat ctc gac ttt gcc gag tct ggg      672
Ser Ala Glu Ile Asn Arg Pro Asp Tyr Leu Asp Phe Ala Glu Ser Gly
    210                215                220

cag gtc tac ttt ggg atc att gcc ctg tga                              702
Gln Val Tyr Phe Gly Ile Ile Ala Leu
225                230
```

<210> SEQ ID NO 18
<211> LENGTH: 233
<212> TYPE: PRT
<213> ORGANISM: Homo sapiens

<400> SEQUENCE: 18

```
Met Ser Thr Glu Ser Met Ile Arg Asp Val Glu Leu Ala Glu Glu Ala
  1               5                  10                  15

Leu Pro Lys Lys Thr Gly Gly Pro Gln Gly Ser Arg Arg Cys Leu Phe
            20                 25                 30

Leu Ser Leu Phe Ser Phe Leu Ile Val Ala Gly Ala Thr Thr Leu Phe
        35                 40                 45

Cys Leu Leu His Phe Gly Val Ile Gly Pro Gln Arg Glu Glu Phe Pro
     50                 55                 60

Arg Asp Leu Ser Leu Ile Ser Pro Leu Ala Gln Ala Val Arg Ser Ser
 65                 70                 75                 80

Ser Arg Thr Pro Ser Asp Lys Pro Val Ala His Val Val Ala Asn Pro
                85                 90                 95

Gln Ala Glu Gly Gln Leu Gln Trp Leu Asn Arg Arg Ala Asn Ala Leu
            100                105                110

Leu Ala Asn Gly Val Glu Leu Arg Asp Asn Gln Leu Val Val Pro Ser
        115                120                125

Glu Gly Leu Tyr Leu Ile Tyr Ser Gln Val Leu Phe Lys Gly Gln Gly
    130                135                140

Cys Pro Ser Thr His Val Leu Leu Thr His Thr Ile Ser Arg Ile Ala
145                150                155                160
```

```
Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 19
<211> LENGTH: 1306
<212> TYPE: DNA
<213> ORGANISM: Homo sapiens
<220> FEATURE:
<221> NAME/KEY: CDS
<222> LOCATION: (18)..(767)

<400> SEQUENCE: 19

cacagccccc cgccccc atg gcc gcc cgt cgg agc cag agg cgg agg ggg       50
                   Met Ala Ala Arg Arg Ser Gln Arg Arg Arg Gly
                   1               5                   10

cgc cgg ggg gag ccg ggc acc gcc ctg ctg gtc ccg ctc gcg ctg ggc       98
Arg Arg Gly Glu Pro Gly Thr Ala Leu Leu Val Pro Leu Ala Leu Gly
            15                  20                  25

ctg ggc ctg gcg ctg gcc tgc ctc ggc ctc ctg ctg gcc gtg gtc agt      146
Leu Gly Leu Ala Leu Ala Cys Leu Gly Leu Leu Leu Ala Val Val Ser
        30                  35                  40

ttg ggg agc cgg gca tcg ctg tcc gcc cag gag cct gcc cag gag gag      194
Leu Gly Ser Arg Ala Ser Leu Ser Ala Gln Glu Pro Ala Gln Glu Glu
    45                  50                  55

ctg gtg gca gag gag gac cag gac ccg tcg gaa ctg aat ccc cag aca      242
Leu Val Ala Glu Glu Asp Gln Asp Pro Ser Glu Leu Asn Pro Gln Thr
 60                 65                  70                  75

gaa gaa agc cag gat cct gcg cct ttc ctg aac cga cta gtt cgg cct      290
Glu Glu Ser Gln Asp Pro Ala Pro Phe Leu Asn Arg Leu Val Arg Pro
                80                  85                  90

cgc aga agt gca cct aaa ggc cgg aaa aca cgg gct cga aga gcg atc      338
Arg Arg Ser Ala Pro Lys Gly Arg Lys Thr Arg Ala Arg Arg Ala Ile
            95                  100                 105

gca gcc cat tat gaa gtt cat cca cga cct gga cag gac gga gcg cag      386
Ala Ala His Tyr Glu Val His Pro Arg Pro Gly Gln Asp Gly Ala Gln
        110                 115                 120

gca ggt gtg gac ggg aca gtg agt ggc tgg gag gaa gcc aga atc aac      434
Ala Gly Val Asp Gly Thr Val Ser Gly Trp Glu Glu Ala Arg Ile Asn
    125                 130                 135

agc tcc agc cct ctg cgc tac aac cgc cag atc ggg gag ttt ata gtc      482
Ser Ser Ser Pro Leu Arg Tyr Asn Arg Gln Ile Gly Glu Phe Ile Val
140                 145                 150                 155

acc cgg gct ggg ctc tac tac ctg tac tgt cag gtg cac ttt gat gag      530
Thr Arg Ala Gly Leu Tyr Tyr Leu Tyr Cys Gln Val His Phe Asp Glu
                160                 165                 170

ggg aag gct gtc tac ctg aag ctg gac ttg ctg gtg gat ggt gtg ctg      578
Gly Lys Ala Val Tyr Leu Lys Leu Asp Leu Leu Val Asp Gly Val Leu
            175                 180                 185

gcc ctg cgc tgc ctg gag gaa ttc tca gcc act gcg gcc agt tcc ctc      626
Ala Leu Arg Cys Leu Glu Glu Phe Ser Ala Thr Ala Ala Ser Ser Leu
        190                 195                 200

ggg ccc cag ctc cgc ctc tgc cag gtg tct ggg ctg ttg gcc ctg cgg      674
Gly Pro Gln Leu Arg Leu Cys Gln Val Ser Gly Leu Leu Ala Leu Arg
```

```
    205                 210                 215

cca ggg tcc tcc ctg cgg atc cgc acc ctc ccc tgg gcc cat ctc aag      722
Pro Gly Ser Ser Leu Arg Ile Arg Thr Leu Pro Trp Ala His Leu Lys
220                 225                 230                 235

gct gcc ccc ttc ctc acc tac ttc gga ctc ttc cag gtt cac tga          767
Ala Ala Pro Phe Leu Thr Tyr Phe Gly Leu Phe Gln Val His
                240                 245                 250

ggggccctgg tctccccaca gtcgtcccag gctgccggct cccctcgaca gctctctggg    827

cacccggtcc cctctgcccc accctcagcc gctctttgct ccagacctgc ccctccctct    887

agaggctgcc tgggcctgtt cacgtgtttt ccatcccaca taaatacagt attcccactc    947

ttatcttaca actcccccac cgcccactct ccacctcact agctccccaa tccctgaccc   1007

tttgaggccc ccagtgatct cgactccccc ctggccacag acccccaggg cattgtgttc   1067

actgtactct gtgggcaagg atgggtccag aagaccccac ttcaggcact aagaggggct   1127

ggacctggcg gcaggaagcc aaagagactg ggcctaggcc aggagttccc aaatgtgagg   1187

ggcgagaaac aagacaagct cctcccttga gaattccctg tggattttta aaacagatat   1247

tatttttatt attattgtga caaaatgttg ataaatggat attaaataga ataagtcag    1306


<210> SEQ ID NO 20
<211> LENGTH: 249
<212> TYPE: PRT
<213> ORGANISM: Homo sapiens

<400> SEQUENCE: 20

Met Ala Ala Arg Arg Ser Gln Arg Arg Arg Gly Arg Arg Gly Glu Pro
  1               5                  10                  15

Gly Thr Ala Leu Leu Val Pro Leu Ala Leu Gly Leu Gly Leu Ala Leu
             20                  25                  30

Ala Cys Leu Gly Leu Leu Leu Ala Val Val Ser Leu Gly Ser Arg Ala
         35                  40                  45

Ser Leu Ser Ala Gln Glu Pro Ala Gln Glu Glu Leu Val Ala Glu Glu
     50                  55                  60

Asp Gln Asp Pro Ser Glu Leu Asn Pro Gln Thr Glu Glu Ser Gln Asp
 65                  70                  75                  80

Pro Ala Pro Phe Leu Asn Arg Leu Val Arg Pro Arg Arg Ser Ala Pro
                 85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240
```

```
Thr Tyr Phe Gly Leu Phe Gln Val His
                245


<210> SEQ ID NO 21
<211> LENGTH: 1769
<212> TYPE: DNA
<213> ORGANISM: Homo sapiens
<220> FEATURE:
<221> NAME/KEY: CDS
<222> LOCATION: (88)..(933)

<400> SEQUENCE: 21

cctcactgac tataaaagaa tagagaagga agggcttcag tgaccggctg cctggctgac      60

ttacagcagt cagactctga caggatc atg gct atg atg gag gtc cag ggg gga     114
                              Met Ala Met Met Glu Val Gln Gly Gly
                                1               5

ccc agc ctg gga cag acc tgc gtg ctg atc gtg atc ttc aca gtg ctc      162
Pro Ser Leu Gly Gln Thr Cys Val Leu Ile Val Ile Phe Thr Val Leu
 10                  15                  20                  25

ctg cag tct ctc tgt gtg gct gta act tac gtg tac ttt acc aac gag      210
Leu Gln Ser Leu Cys Val Ala Val Thr Tyr Val Tyr Phe Thr Asn Glu
                 30                  35                  40

ctg aag cag atg cag gac aag tac tcc aaa agt ggc att gct tgt ttc      258
Leu Lys Gln Met Gln Asp Lys Tyr Ser Lys Ser Gly Ile Ala Cys Phe
             45                  50                  55

tta aaa gaa gat gac agt tat tgg gac ccc aat gac gaa gag agt atg      306
Leu Lys Glu Asp Asp Ser Tyr Trp Asp Pro Asn Asp Glu Glu Ser Met
         60                  65                  70

aac agc ccc tgc tgg caa gtc aag tgg caa ctc cgt cag ctc gtt aga      354
Asn Ser Pro Cys Trp Gln Val Lys Trp Gln Leu Arg Gln Leu Val Arg
     75                  80                  85

aag atg att ttg aga acc tct gag gaa acc att tct aca gtt caa gaa      402
Lys Met Ile Leu Arg Thr Ser Glu Glu Thr Ile Ser Thr Val Gln Glu
 90                  95                 100                 105

aag caa caa aat att tct ccc cta gtg aga gaa aga ggt cct cag aga      450
Lys Gln Gln Asn Ile Ser Pro Leu Val Arg Glu Arg Gly Pro Gln Arg
                110                 115                 120

gta gca gct cac ata act ggg acc aga gga aga agc aac aca ttg tct      498
Val Ala Ala His Ile Thr Gly Thr Arg Gly Arg Ser Asn Thr Leu Ser
            125                 130                 135

tct cca aac tcc aag aat gaa aag gct ctg ggc cgc aaa ata aac tcc      546
Ser Pro Asn Ser Lys Asn Glu Lys Ala Leu Gly Arg Lys Ile Asn Ser
        140                 145                 150

tgg gaa tca tca agg agt ggg cat tca ttc ctg agc aac ttg cac ttg      594
Trp Glu Ser Ser Arg Ser Gly His Ser Phe Leu Ser Asn Leu His Leu
    155                 160                 165

agg aat ggt gaa ctg gtc atc cat gaa aaa ggg ttt tac tac atc tat      642
Arg Asn Gly Glu Leu Val Ile His Glu Lys Gly Phe Tyr Tyr Ile Tyr
170                 175                 180                 185

tcc caa aca tac ttt cga ttt cag gag gaa ata aaa gaa aac aca aag      690
Ser Gln Thr Tyr Phe Arg Phe Gln Glu Glu Ile Lys Glu Asn Thr Lys
                190                 195                 200

aac gac aaa caa atg gtc caa tat att tac aaa tac aca agt tat cct      738
Asn Asp Lys Gln Met Val Gln Tyr Ile Tyr Lys Tyr Thr Ser Tyr Pro
            205                 210                 215

gac cct ata ttg ttg atg aaa agt gct aga aat agt tgt tgg tct aaa      786
Asp Pro Ile Leu Leu Met Lys Ser Ala Arg Asn Ser Cys Trp Ser Lys
        220                 225                 230

gat gca gaa tat gga ctc tat tcc atc tat caa ggg gga ata ttt gag      834
Asp Ala Glu Tyr Gly Leu Tyr Ser Ile Tyr Gln Gly Gly Ile Phe Glu
    235                 240                 245
```

```
ctt aag gaa aat gac aga att ttt gtt tct gta aca aat gag cac ttg      882
Leu Lys Glu Asn Asp Arg Ile Phe Val Ser Val Thr Asn Glu His Leu
250                 255                 260                 265

ata gac atg gac cat gaa gcc agt ttt ttc ggg gcc ttt tta gtt ggc      930
Ile Asp Met Asp His Glu Ala Ser Phe Phe Gly Ala Phe Leu Val Gly
                270                 275                 280

taa ctgacctgga aagaaaaagc aataacctca aagtgactat tcagttttca           983

ggatgataca ctatgaagat gtttcaaaaa atctgaccaa aacaaacaaa cagaaaacag   1043

aaaacaaaaa aacctctatg caatctgagt agagcagcca caaccaaaaa attctacaac   1103

acacactgtt ctgaaagtga ctcacttatc ccaagaaaat gaaattgctg aaagatcttt   1163

caggactcta cctcatatca gtttgctagc agaaatctag aagactgtca gcttccaaac   1223

attaatgcaa tggttaacat cttctgtctt tataatctac tccttgtaaa gactgtagaa   1283

gaaagcgcaa caatccatct ctcaagtagt gtatcacagt agtagcctcc aggtttcctt   1343

aagggacaac atccttaagt caaaagagag aagaggcacc actaaaagat cgcagtttgc   1403

ctggtgcagt ggctcacacc tgtaatccca acattttggg aacccaaggt gggtagatca   1463

cgagatcaag agatcaagac catagtgacc aacatagtga aaccccatct ctactgaaag   1523

tgcaaaaatt agctgggtgt gttggcacat gcctgtagtc ccagctactt gagaggctga   1583

ggcaggagaa tcgtttgaac ccgggaggca gaggttgcag tgtggtgaga tcatgccact   1643

acactccagc ctggcgacag agcgagactt ggtttcaaaa aaaaaaaaaa aaaaaaactt   1703

cagtaagtac gtgttatttt tttcaataaa attctattac agtatgtcaa aaaaaaaaaa   1763

aaaaaa                                                              1769


<210> SEQ ID NO 22
<211> LENGTH: 281
<212> TYPE: PRT
<213> ORGANISM: Homo sapiens

<400> SEQUENCE: 22

Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
             20                  25                  30

Val Thr Tyr Val Tyr Phe Thr Asn Glu Leu Lys Gln Met Gln Asp Lys
         35                  40                  45

Tyr Ser Lys Ser Gly Ile Ala Cys Phe Leu Lys Glu Asp Asp Ser Tyr
     50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                 85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175
```

```
His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 23
<211> LENGTH: 1042
<212> TYPE: DNA
<213> ORGANISM: Homo sapiens
<220> FEATURE:
<221> NAME/KEY: CDS
<222> LOCATION: (91)..(936)

<400> SEQUENCE: 23

tttcctcact gactataaaa gaatagagaa ggaagggctt cagtgaccgg ctgcctggct     60

gacttacagc agtcagactc tgacaggatc atg gct atg atg gag gtc cag ggg     114
                                 Met Ala Met Met Glu Val Gln Gly
                                   1               5

gga ccc agc ctg gga cag acc tgc gtg ctg atc gtg atc ttc aca gtg      162
Gly Pro Ser Leu Gly Gln Thr Cys Val Leu Ile Val Ile Phe Thr Val
     10                  15                  20

ctc ctg cag tct ctc tgt gtg gct gta act tac gtg tac ttt acc aac      210
Leu Leu Gln Ser Leu Cys Val Ala Val Thr Tyr Val Tyr Phe Thr Asn
 25                  30                  35                  40

gag ctg aag cag atg cag gac aag tac tcc aaa agt ggc att gct tgt      258
Glu Leu Lys Gln Met Gln Asp Lys Tyr Ser Lys Ser Gly Ile Ala Cys
                 45                  50                  55

ttc tta aaa gaa gat gac agt tat tgg gac ccc aat gac gaa gag agt      306
Phe Leu Lys Glu Asp Asp Ser Tyr Trp Asp Pro Asn Asp Glu Glu Ser
             60                  65                  70

atg aac agc ccc tgc tgg caa gtc aag tgg caa ctc cgt cag ctc gtt      354
Met Asn Ser Pro Cys Trp Gln Val Lys Trp Gln Leu Arg Gln Leu Val
         75                  80                  85

aga aag atg att ttg aga acc tct gag gaa acc att tct aca gtt caa      402
Arg Lys Met Ile Leu Arg Thr Ser Glu Glu Thr Ile Ser Thr Val Gln
     90                  95                 100

gaa aag caa caa aat att tct ccc cta gtg aga gaa aga ggt cct cag      450
Glu Lys Gln Gln Asn Ile Ser Pro Leu Val Arg Glu Arg Gly Pro Gln
105                 110                 115                 120

aga gta gca gct cac ata act ggg acc aga gga aga agc aac aca ttg      498
Arg Val Ala Ala His Ile Thr Gly Thr Arg Gly Arg Ser Asn Thr Leu
                125                 130                 135

tct tct cca aac tcc aag aat gaa aag gct ctg ggc cgc aaa ata aac      546
Ser Ser Pro Asn Ser Lys Asn Glu Lys Ala Leu Gly Arg Lys Ile Asn
            140                 145                 150

tcc tgg gaa tca tca agg agt ggg cat tca ttc ctg agc aac ttg cac      594
Ser Trp Glu Ser Ser Arg Ser Gly His Ser Phe Leu Ser Asn Leu His
        155                 160                 165

ttg agg aat ggt gaa ctg gtc atc cat gaa aaa ggg ttt tac tac atc      642
Leu Arg Asn Gly Glu Leu Val Ile His Glu Lys Gly Phe Tyr Tyr Ile
```

```
    170                 175                 180

tat tcc caa aca tac ttt cga ttt cag gag gaa ata aaa gaa aac aca      690
Tyr Ser Gln Thr Tyr Phe Arg Phe Gln Glu Glu Ile Lys Glu Asn Thr
185                 190                 195                 200

aag aac gac aaa caa atg gtc caa tat att tac aaa tac aca agt tat      738
Lys Asn Asp Lys Gln Met Val Gln Tyr Ile Tyr Lys Tyr Thr Ser Tyr
                205                 210                 215

cct gac cct ata ttg ttg atg aaa agt gct aga aat agt tgt tgg tct      786
Pro Asp Pro Ile Leu Leu Met Lys Ser Ala Arg Asn Ser Cys Trp Ser
            220                 225                 230

aaa gat gca gaa tat gga ctc tat tcc atc tat caa ggg gga ata ttt      834
Lys Asp Ala Glu Tyr Gly Leu Tyr Ser Ile Tyr Gln Gly Gly Ile Phe
        235                 240                 245

gag ctt aag gaa aat gac aga att ttt gtt tct gta aca aat gag cac      882
Glu Leu Lys Glu Asn Asp Arg Ile Phe Val Ser Val Thr Asn Glu His
    250                 255                 260

ttg ata gac atg gac cat gaa gcc agt ttt ttc ggg gcc ttt tta gtt      930
Leu Ile Asp Met Asp His Glu Ala Ser Phe Phe Gly Ala Phe Leu Val
265                 270                 275                 280

ggc taa ctgacctgga aagaaaaagc aataacctca aagtgactat tcagttttca       986
Gly

ggatgataca ctatgaagat gtttcaaaaa atctgaccaa aacaaacaaa cagaaa       1042


<210> SEQ ID NO 24
<211> LENGTH: 281
<212> TYPE: PRT
<213> ORGANISM: Homo sapiens

<400> SEQUENCE: 24

Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220
```

```
Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 25
<211> LENGTH: 579
<212> TYPE: DNA
<213> ORGANISM: Homo sapiens
<220> FEATURE:
<221> NAME/KEY: CDS
<222> LOCATION: (1)..(579)

<400> SEQUENCE: 25

atg gac ggg tcc ggg gag cag ccc aga ggc ggg ggg ccc acc agc tct       48
Met Asp Gly Ser Gly Glu Gln Pro Arg Gly Gly Gly Pro Thr Ser Ser
  1               5                  10                  15

gag cag atc atg aag aca ggg gcc ctt ttg ctt cag ggt ttc atc cag       96
Glu Gln Ile Met Lys Thr Gly Ala Leu Leu Leu Gln Gly Phe Ile Gln
             20                  25                  30

gat cga gca ggg cga atg ggg ggg gag gca ccc gag ctg gcc ctg gac      144
Asp Arg Ala Gly Arg Met Gly Gly Glu Ala Pro Glu Leu Ala Leu Asp
         35                  40                  45

ccg gtg cct cag gat gcg tcc acc aag aag ctg agc gag tgt ctc aag      192
Pro Val Pro Gln Asp Ala Ser Thr Lys Lys Leu Ser Glu Cys Leu Lys
     50                  55                  60

cgc atc ggg gac gaa ctg gac agt aac atg gag ctg cag agg atg att      240
Arg Ile Gly Asp Glu Leu Asp Ser Asn Met Glu Leu Gln Arg Met Ile
 65                  70                  75                  80

gcc gcc gtg gac aca gac tcc ccc cga gag gtc ttt ttc cga gtg gca      288
Ala Ala Val Asp Thr Asp Ser Pro Arg Glu Val Phe Phe Arg Val Ala
                 85                  90                  95

gct gac atg ttt tct gac ggc aac ttc aac tgg ggc cgg gtt gtc gcc      336
Ala Asp Met Phe Ser Asp Gly Asn Phe Asn Trp Gly Arg Val Val Ala
            100                 105                 110

ctt ttc tac ttt gcc agc aaa ctg gtg ctc aag gcc ctg tgc acc aag      384
Leu Phe Tyr Phe Ala Ser Lys Leu Val Leu Lys Ala Leu Cys Thr Lys
        115                 120                 125

gtg ccg gaa ctg atc aga acc atc atg ggc tgg aca ttg gac ttc ctc      432
Val Pro Glu Leu Ile Arg Thr Ile Met Gly Trp Thr Leu Asp Phe Leu
    130                 135                 140

cgg gag cgg ctg ttg ggc tgg atc caa gac cag ggt ggt tgg gac ggc      480
Arg Glu Arg Leu Leu Gly Trp Ile Gln Asp Gln Gly Gly Trp Asp Gly
145                 150                 155                 160

ctc ctc tcc tac ttt ggg acg ccc acg tgg cag acc gtg acc atc ttt      528
Leu Leu Ser Tyr Phe Gly Thr Pro Thr Trp Gln Thr Val Thr Ile Phe
                165                 170                 175

gtg gcg gga gtg ctc acc gcc tcg ctc acc atc tgg aag aag atg ggc      576
Val Ala Gly Val Leu Thr Ala Ser Leu Thr Ile Trp Lys Lys Met Gly
            180                 185                 190

tga                                                                   579


<210> SEQ ID NO 26
<211> LENGTH: 192
<212> TYPE: PRT
<213> ORGANISM: Homo sapiens
```

<400> SEQUENCE: 26

```
Met Asp Gly Ser Gly Glu Gln Pro Arg Gly Gly Gly Pro Thr Ser Ser
  1               5                  10                  15

Glu Gln Ile Met Lys Thr Gly Ala Leu Leu Leu Gln Gly Phe Ile Gln
             20                  25                  30

Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
     50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

<210> SEQ ID NO 27
<211> LENGTH: 1105
<212> TYPE: DNA
<213> ORGANISM: Homo sapiens
<220> FEATURE:
<221> NAME/KEY: CDS
<222> LOCATION: (141)..(728)

<400> SEQUENCE: 27

```
gggcgggtag tcgaccgtgt ccgcgcgcct gggagacgct gcctcggccc ggacgcgccc      60

gcgcccccgc ggctggaggg tggtcgccac tgggacactg tgaaccagga gtgagtcgga     120

gctgccgcgc tgcccaggcc atg gac tgt gag gtc aac aac ggt tcc agc ctc     173
                      Met Asp Cys Glu Val Asn Asn Gly Ser Ser Leu
                        1               5                  10

agg gat gag tgc atc aca aac cta ctg gtg ttt ggc ttc ctc caa agc       221
Arg Asp Glu Cys Ile Thr Asn Leu Leu Val Phe Gly Phe Leu Gln Ser
             15                  20                  25

tgt tct gac aac agc ttc cgc aga gag ctg gac gca ctg ggc cac gag       269
Cys Ser Asp Asn Ser Phe Arg Arg Glu Leu Asp Ala Leu Gly His Glu
         30                  35                  40

ctg cca gtg ctg gct ccc cag tgg gag ggc tac gat gag ctg cag act       317
Leu Pro Val Leu Ala Pro Gln Trp Glu Gly Tyr Asp Glu Leu Gln Thr
     45                  50                  55

gat ggc aac cgc agc agc cac tcc cgc ttg gga aga ata gag gca gat       365
Asp Gly Asn Arg Ser Ser His Ser Arg Leu Gly Arg Ile Glu Ala Asp
 60                  65                  70                  75

tct gaa agt caa gaa gac atc atc cgg aat att gcc agg cac ctc gcc       413
Ser Glu Ser Gln Glu Asp Ile Ile Arg Asn Ile Ala Arg His Leu Ala
                 80                  85                  90

cag gtc ggg gac agc atg gac cgt agc atc cct ccg ggc ctg gtg aac       461
Gln Val Gly Asp Ser Met Asp Arg Ser Ile Pro Pro Gly Leu Val Asn
             95                 100                 105
```

```
ggc ctg gcc ctg cag ctc agg aac acc agc cgg tcg gag gag gac cgg      509
Gly Leu Ala Leu Gln Leu Arg Asn Thr Ser Arg Ser Glu Glu Asp Arg
        110                 115                 120

aac agg gac ctg gcc act gcc ctg gag cag ctg ctg cag gcc tac cct      557
Asn Arg Asp Leu Ala Thr Ala Leu Glu Gln Leu Leu Gln Ala Tyr Pro
    125                 130                 135

aga gac atg gag aag gag aag acc atg ctg gtg ctg gcc ctg ctg ctg      605
Arg Asp Met Glu Lys Glu Lys Thr Met Leu Val Leu Ala Leu Leu Leu
140                 145                 150                 155

gcc aag aag gtg gcc agt cac acg ccg tcc ttg ctc cgt gat gtc ttt      653
Ala Lys Lys Val Ala Ser His Thr Pro Ser Leu Leu Arg Asp Val Phe
                160                 165                 170

cac aca aca gtg aat ttt att aac cag aac cta cgc acc tac gtg agg      701
His Thr Thr Val Asn Phe Ile Asn Gln Asn Leu Arg Thr Tyr Val Arg
            175                 180                 185

agc tta gcc aga aat ggg atg gac tga acggacagtt ccagaagtgt            748
Ser Leu Ala Arg Asn Gly Met Asp
        190                 195

gactggctaa agcttgatgt ggtcacagct gtatagctgc ttccagtgta gacggagccc    808

tggcatgtca acagcgttcc tagagaagac aggctggaag atagctgtga cttctatttt    868

aaagacaatg ttaaacttat aacccacttt aaaatatcta cattaatata cttgaatgaa    928

aatgtccatt tacacgtatt tgaatggcct tcatatcatc cacacatgaa tctgcacatc    988

tgtaaatcta cacacggtgc ctttatttcc actgtgcagg ttcccactta aaaattaaat   1048

tggaaagcag gtttcaagga agtagaaaca aaatacaatt tttttggtaa aaaaaaa      1105


<210> SEQ ID NO 28
<211> LENGTH: 195
<212> TYPE: PRT
<213> ORGANISM: Homo sapiens

<400> SEQUENCE: 28

Met Asp Cys Glu Val Asn Asn Gly Ser Ser Leu Arg Asp Glu Cys Ile
  1               5                  10                  15

Thr Asn Leu Leu Val Phe Gly Phe Leu Gln Ser Cys Ser Asp Asn Ser
             20                  25                  30

Phe Arg Arg Glu Leu Asp Ala Leu Gly His Glu Leu Pro Val Leu Ala
         35                  40                  45

Pro Gln Trp Glu Gly Tyr Asp Glu Leu Gln Thr Asp Gly Asn Arg Ser
     50                  55                  60

Ser His Ser Arg Leu Gly Arg Ile Glu Ala Asp Ser Glu Ser Gln Glu
 65                  70                  75                  80

Asp Ile Ile Arg Asn Ile Ala Arg His Leu Ala Gln Val Gly Asp Ser
                 85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190
```

```
Gly Met Asp
        195


<210> SEQ ID NO 29
<211> LENGTH: 923
<212> TYPE: DNA
<213> ORGANISM: Homo sapiens
<220> FEATURE:
<221> NAME/KEY: CDS
<222> LOCATION: (26)..(508)

<400> SEQUENCE: 29

cagcatcgcc gccgccagag gagaa atg tct gaa gta aga ccc ctc tcc aga       52
                            Met Ser Glu Val Arg Pro Leu Ser Arg
                              1               5

gac atc ttg atg gag acc ctc ctg tat gag cag ctc ctg gaa ccc ccg      100
Asp Ile Leu Met Glu Thr Leu Leu Tyr Glu Gln Leu Leu Glu Pro Pro
 10                  15                  20                  25

acc atg gag gtt ctt ggc atg act gac tct gaa gag gac ctg gac cct      148
Thr Met Glu Val Leu Gly Met Thr Asp Ser Glu Glu Asp Leu Asp Pro
                 30                  35                  40

atg gag gac ttc gat tct ttg gaa tgc atg gag ggc agt gac gca ttg      196
Met Glu Asp Phe Asp Ser Leu Glu Cys Met Glu Gly Ser Asp Ala Leu
             45                  50                  55

gcc ctg cgg ctg gcc tgc atc ggg gac gag atg gac gtg agc ctc agg      244
Ala Leu Arg Leu Ala Cys Ile Gly Asp Glu Met Asp Val Ser Leu Arg
         60                  65                  70

gcc ccg cgc ctg gcc cag ctc tcc gag gtg gcc atg cac agc ctg ggt      292
Ala Pro Arg Leu Ala Gln Leu Ser Glu Val Ala Met His Ser Leu Gly
     75                  80                  85

ctg gct ttc atc tac gac cag act gag gac atc agg gat gtt ctt aga      340
Leu Ala Phe Ile Tyr Asp Gln Thr Glu Asp Ile Arg Asp Val Leu Arg
 90                  95                 100                 105

agt ttc atg gac ggt ttc acc aca ctt aag gag aac ata atg agg ttc      388
Ser Phe Met Asp Gly Phe Thr Thr Leu Lys Glu Asn Ile Met Arg Phe
                110                 115                 120

tgg aga tcc ccg aac ccc ggg tcc tgg gtg tcc tgc gaa cag gtg ctg      436
Trp Arg Ser Pro Asn Pro Gly Ser Trp Val Ser Cys Glu Gln Val Leu
            125                 130                 135

ctg gcg ctg ctg ctg ctg ctg gcg ctg ctg ctg ccg ctg ctc agc ggg      484
Leu Ala Leu Leu Leu Leu Leu Ala Leu Leu Leu Pro Leu Leu Ser Gly
        140                 145                 150

ggc ctg cac ctg ctg ctc aag tga gcccccggcg gctcaggcgt ggctggcccc      538
Gly Leu His Leu Leu Leu Lys
    155                 160

acccccatga ccactgccct gaggtggcgg cctgctgctg ttatcttttt aactgttttc     598

tcatgatgcc ttttatatta accccgtgat agtgctggaa cactgctgag gttttatact     658

caggtttttt gttttttttt tattccagtt ttcgtttttt ctaaaagatg aattcctatg     718

gctctgcaat tgtcaccggt taactgtggc ctgtgcccag gaagagccat tcactcctgc     778

ccctgcccac acggcaggta gcagggggag tgctggtcac acccctgtgt gatatgtgat     838

gccctcggca aagaatctac tggaatagat tccgaggagc aggagtgctc aataaaatgt     898

tggtttccag caaaaaaaaa aaaaa                                           923


<210> SEQ ID NO 30
<211> LENGTH: 160
<212> TYPE: PRT
<213> ORGANISM: Homo sapiens

<400> SEQUENCE: 30
```

```
Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Leu Pro Leu Leu Ser Gly Gly Leu His Leu Leu Leu Lys
145                 150                 155                 160


<210> SEQ ID NO 31
<211> LENGTH: 507
<212> TYPE: DNA
<213> ORGANISM: Homo sapiens
<220> FEATURE:
<221> NAME/KEY: CDS
<222> LOCATION: (1)..(507)

<400> SEQUENCE: 31

atg ttc cag atc cca gag ttt gag ccg agt gag cag gaa gac tcc agc      48
Met Phe Gln Ile Pro Glu Phe Glu Pro Ser Glu Gln Glu Asp Ser Ser
1               5                   10                  15

tct gca gag agg ggc ctg ggc ccc agc ccc gca ggg gac ggg ccc tca      96
Ser Ala Glu Arg Gly Leu Gly Pro Ser Pro Ala Gly Asp Gly Pro Ser
            20                  25                  30

ggc tcc ggc aag cat cat cgc cag gcc cca ggc ctc ctg tgg gac gcc     144
Gly Ser Gly Lys His His Arg Gln Ala Pro Gly Leu Leu Trp Asp Ala
        35                  40                  45

agt cac cag cag gag cag cca acc agc agc agc cat cat gga ggc gct     192
Ser His Gln Gln Glu Gln Pro Thr Ser Ser Ser His His Gly Gly Ala
    50                  55                  60

ggg gct gtg gag atc cgg agt cgc cac agc tcc tac ccc gcg ggg acg     240
Gly Ala Val Glu Ile Arg Ser Arg His Ser Ser Tyr Pro Ala Gly Thr
65                  70                  75                  80

gag gac gac gaa ggg atg ggg gag gag ccc agc ccc ttt cgg ggc cgc     288
Glu Asp Asp Glu Gly Met Gly Glu Glu Pro Ser Pro Phe Arg Gly Arg
                85                  90                  95

tcg cgc tcg gcg ccc ccc aac ctc tgg gca gca cag cgc tat ggc cgc     336
Ser Arg Ser Ala Pro Pro Asn Leu Trp Ala Ala Gln Arg Tyr Gly Arg
            100                 105                 110

gag ctc cgg agg atg agt gac gag ttt gtg gac tcc ttt aag aag gga     384
Glu Leu Arg Arg Met Ser Asp Glu Phe Val Asp Ser Phe Lys Lys Gly
        115                 120                 125

ctt cct cgc ccg aag agc gcg ggc aca gca acg cag atg cgg caa agc     432
Leu Pro Arg Pro Lys Ser Ala Gly Thr Ala Thr Gln Met Arg Gln Ser
    130                 135                 140

tcc agc tgg acg cga gtc ttc cag tcc tgg tgg gat cgg aac ttg ggc     480
Ser Ser Trp Thr Arg Val Phe Gln Ser Trp Trp Asp Arg Asn Leu Gly
```

```
145                 150                 155                 160

agg gga agc tcc gcc ccc tcc cag tga                                507
Arg Gly Ser Ser Ala Pro Ser Gln
                165


<210> SEQ ID NO 32
<211> LENGTH: 168
<212> TYPE: PRT
<213> ORGANISM: Homo sapiens

<400> SEQUENCE: 32

Met Phe Gln Ile Pro Glu Phe Glu Pro Ser Glu Gln Glu Asp Ser Ser
  1               5                  10                  15

Ser Ala Glu Arg Gly Leu Gly Pro Ser Pro Ala Gly Asp Gly Pro Ser
             20                  25                  30

Gly Ser Gly Lys His His Arg Gln Ala Pro Gly Leu Leu Trp Asp Ala
         35                  40                  45

Ser His Gln Gln Glu Gln Pro Thr Ser Ser Ser His His Gly Gly Ala
     50                  55                  60

Gly Ala Val Glu Ile Arg Ser Arg His Ser Ser Tyr Pro Ala Gly Thr
 65                  70                  75                  80

Glu Asp Asp Glu Gly Met Gly Glu Glu Pro Ser Pro Phe Arg Gly Arg
                 85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165


<210> SEQ ID NO 33
<211> LENGTH: 1949
<212> TYPE: DNA
<213> ORGANISM: Homo sapiens
<220> FEATURE:
<221> NAME/KEY: CDS
<222> LOCATION: (65)..(700)

<400> SEQUENCE: 33

tgagccaccc gggttgggcc aggatcccgg caggctgatc ccgtcctcca ctgagacctg      60

aaaa atg gct tcg ggg caa ggc cca ggt cct ccc agg cag gag tgc gga      109
     Met Ala Ser Gly Gln Gly Pro Gly Pro Pro Arg Gln Glu Cys Gly
       1               5                  10                  15

gag cct gcc ctg ccc tct gct tct gag gag cag gta gcc cag gac aca      157
Glu Pro Ala Leu Pro Ser Ala Ser Glu Glu Gln Val Ala Gln Asp Thr
                 20                  25                  30

gag gag gtt ttc cgc agc tac gtt ttt tac cgc cat cag cag gaa cag      205
Glu Glu Val Phe Arg Ser Tyr Val Phe Tyr Arg His Gln Gln Glu Gln
             35                  40                  45

gag gct gaa ggg gtg gct gcc cct gcc gac cca gag atg gtc acc tta      253
Glu Ala Glu Gly Val Ala Ala Pro Ala Asp Pro Glu Met Val Thr Leu
         50                  55                  60

cct ctg caa cct agc agc acc atg ggg cag gtg gga cgg cag ctc gcc      301
Pro Leu Gln Pro Ser Ser Thr Met Gly Gln Val Gly Arg Gln Leu Ala
     65                  70                  75
```

```
atc atc ggg gac gac atc aac cga cgc tat gac tca gag ttc cag acc      349
Ile Ile Gly Asp Asp Ile Asn Arg Arg Tyr Asp Ser Glu Phe Gln Thr
 80                  85                  90                  95

atg ttg cag cac ctg cag ccc acg gca gag aat gcc tat gag tac ttc      397
Met Leu Gln His Leu Gln Pro Thr Ala Glu Asn Ala Tyr Glu Tyr Phe
                100                 105                 110

acc aag att gcc acc agc ctg ttt gag agt ggc atc aat tgg ggc cgt      445
Thr Lys Ile Ala Thr Ser Leu Phe Glu Ser Gly Ile Asn Trp Gly Arg
            115                 120                 125

gtg gtg gct ctt ctg ggc ttc ggc tac cgt ctg gcc cta cac gtc tac      493
Val Val Ala Leu Leu Gly Phe Gly Tyr Arg Leu Ala Leu His Val Tyr
        130                 135                 140

cag cat ggc ctg act ggc ttc cta ggc cag gtg acc cgc ttc gtg gtc      541
Gln His Gly Leu Thr Gly Phe Leu Gly Gln Val Thr Arg Phe Val Val
    145                 150                 155

gac ttc atg ctg cat cac tgc att gcc cgg tgg att gca cag agg ggt      589
Asp Phe Met Leu His His Cys Ile Ala Arg Trp Ile Ala Gln Arg Gly
160                 165                 170                 175

ggc tgg gtg gca gcc ctg aac ttg ggc aat ggt ccc atc ctg aac gtg      637
Gly Trp Val Ala Ala Leu Asn Leu Gly Asn Gly Pro Ile Leu Asn Val
                180                 185                 190

ctg gtg gtt ctg ggt gtg gtt ctg ttg ggc cag ttt gtg gta cga aga      685
Leu Val Val Leu Gly Val Val Leu Leu Gly Gln Phe Val Val Arg Arg
            195                 200                 205

ttc ttc aaa tca tga ctcccaaggg tgccctttgg gtcccggttc agacccctgc      740
Phe Phe Lys Ser
        210

ctggacttaa gcgaagtctt tgccttctct gttcccttgc aggggtcccc cctcaagagt    800

acagaagctt tagcaagtgt gcactccagc ttcggagggc cctgcgtgg gggccagtca    860

ggctgcagag gcacctcaac attgcatggt gctagtgggc cctctctctg ggcccagggg    920

ctgtggccgt ctcctccctc agctctctgg gacctcctta gccctgtctg ctaggcgctg    980

gggagactga taacttgggg aggcaagaga ctgggagcca cttctcccca gaaagtgttt   1040

aacggtttta gctttttata atacccttgt gagagcccat tcccaccatt ctacctgagg   1100

ccaggacgtc tggggtgtgg ggattggtgg gtctatgttc cccaggattc agctattctg   1160

gaagatcagc accctaagag atgggactag gacctgagcc tggtcctggc cgtccctaag   1220

catgtgtccc aggagcagga cctactagga gagggggggcc aaggtcctgc tcaactctac   1280

ccctgctccc attcctccct ccggccatac tgcctttgca gttggactct cagggattct   1340

gggcttgggg tgtggggtgg ggtggagtcg cagaccagag ctgtctgaac tcacgtgtca   1400

gaagcctcca agcctgcctc ccaaggtcct ctcagttctc tcccttcctc tctccttata   1460

gacacttgct cccaacccat tcactacagg tgaaggctct caccccatcc ctgggggcct   1520

tgggtgagtg gcctgctaag gctcctcctt gcccagacta cagggcttag gacttggttt   1580

gttatatcag ggaaaaggag tagggagttc atctggaggg ttctaagtgg gagaaggact   1640

atcaacacca ctaggaatcc cagaggtggg atcctccctc atggctctgg cacagtgtaa   1700

tccaggggtg tagatggggg aactgtgaat acttgaactc tgttccccca ccctccatgc   1760

tcctcacctg tctaggtctc ctcagggtgg ggggtgacag tgccttctct attgggcaca   1820

gcctagggtc ttgggggtca ggggggagaa gttcttgatt cagccaaatg cagggagggg   1880

aggcagatgg agcccatagg ccacccccta tcctctgagt gtttggaaat aaactgtgca   1940

atcccctca                                                            1949
```

<210> SEQ ID NO 34

<211> LENGTH: 211
<212> TYPE: PRT
<213> ORGANISM: Homo sapiens

<400> SEQUENCE: 34

```
Met Ala Ser Gly Gln Gly Pro Gly Pro Pro Arg Gln Glu Cys Gly Glu
  1               5                  10                  15

Pro Ala Leu Pro Ser Ala Ser Glu Glu Gln Val Ala Gln Asp Thr Glu
             20                  25                  30

Glu Val Phe Arg Ser Tyr Val Phe Tyr Arg His Gln Gln Glu Gln Glu
         35                  40                  45

Ala Glu Gly Val Ala Ala Pro Ala Asp Pro Glu Met Val Thr Leu Pro
     50                  55                  60

Leu Gln Pro Ser Ser Thr Met Gly Gln Val Gly Arg Gln Leu Ala Ile
 65                  70                  75                  80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210
```

<210> SEQ ID NO 35
<211> LENGTH: 2501
<212> TYPE: DNA
<213> ORGANISM: Homo sapiens
<220> FEATURE:
<221> NAME/KEY: CDS
<222> LOCATION: (225)..(1847)

<400> SEQUENCE: 35

```
ggcaccagtc tctagaaaag aagtcagctc tggttcggag aagcagcggc tggcgtgggc      60

catccgggga atgggcgccc tcgtgaccta gtgttgcggg gcaaaaaggg tcttgccggc     120

ctcgctcgtg caggggcgta tctgggcgcc tgagcgcgca gtgggagcct tgggagccgc     180

cgcagcaggg ggcacacccg gaaccggcct gagcgcccgg gacc atg aac ggg gag      236
                                                 Met Asn Gly Glu
                                                   1

gcc atc tgc agc gcc ctg ccc acc att ccc tac cac aaa ctc gcc gac       284
Ala Ile Cys Ser Ala Leu Pro Thr Ile Pro Tyr His Lys Leu Ala Asp
  5                  10                  15                  20

ctg cgc tac ctg agc cgc ggc gcc tct ggc act gtg tcg tcc gcc cgc       332
Leu Arg Tyr Leu Ser Arg Gly Ala Ser Gly Thr Val Ser Ser Ala Arg
                 25                  30                  35

cac gca gac tgg cgc gtc cag gtg gcc gtg aag cac ctg cac atc cac       380
His Ala Asp Trp Arg Val Gln Val Ala Val Lys His Leu His Ile His
             40                  45                  50
```

```
act ccg ctg ctc gac agt gaa aga aag gat gtc tta aga gaa gct gaa      428
Thr Pro Leu Leu Asp Ser Glu Arg Lys Asp Val Leu Arg Glu Ala Glu
        55                  60                  65

att tta cac aaa gct aga ttt agt tac att ctt cca att ttg gga att      476
Ile Leu His Lys Ala Arg Phe Ser Tyr Ile Leu Pro Ile Leu Gly Ile
    70                  75                  80

tgc aat gag cct gaa ttt ttg gga ata gtt act gaa tac atg cca aat      524
Cys Asn Glu Pro Glu Phe Leu Gly Ile Val Thr Glu Tyr Met Pro Asn
85                  90                  95                  100

gga tca tta aat gaa ctc cta cat agg aaa act gaa tat cct gat gtt      572
Gly Ser Leu Asn Glu Leu Leu His Arg Lys Thr Glu Tyr Pro Asp Val
                105                 110                 115

gct tgg cca ttg aga ttt cgc atc ctg cat gaa att gcc ctt ggt gta      620
Ala Trp Pro Leu Arg Phe Arg Ile Leu His Glu Ile Ala Leu Gly Val
            120                 125                 130

aat tac ctg cac aat atg act cct cct tta ctt cat cat gac ttg aag      668
Asn Tyr Leu His Asn Met Thr Pro Pro Leu Leu His His Asp Leu Lys
        135                 140                 145

act cag aat atc tta ttg gac aat gaa ttt cat gtt aag att gca gat      716
Thr Gln Asn Ile Leu Leu Asp Asn Glu Phe His Val Lys Ile Ala Asp
    150                 155                 160

ttt ggt tta tca aag tgg cgc atg atg tcc ctc tca cag tca cga agt      764
Phe Gly Leu Ser Lys Trp Arg Met Met Ser Leu Ser Gln Ser Arg Ser
165                 170                 175                 180

agc aaa tct gca cca gaa gga ggg aca att atc tat atg cca cct gaa      812
Ser Lys Ser Ala Pro Glu Gly Gly Thr Ile Ile Tyr Met Pro Pro Glu
                185                 190                 195

aac tat gaa cct gga caa aaa tca agg gcc agt atc aag cac gat ata      860
Asn Tyr Glu Pro Gly Gln Lys Ser Arg Ala Ser Ile Lys His Asp Ile
            200                 205                 210

tat agc tat gca gtt atc aca tgg gaa gtg tta tcc aga aaa cag cct      908
Tyr Ser Tyr Ala Val Ile Thr Trp Glu Val Leu Ser Arg Lys Gln Pro
        215                 220                 225

ttt gaa gat gtc acc aat cct ttg cag ata atg tat agt gtg tca caa      956
Phe Glu Asp Val Thr Asn Pro Leu Gln Ile Met Tyr Ser Val Ser Gln
    230                 235                 240

gga cat cga cct gtt att aat gaa gaa agt ttg cca tat gat ata cct     1004
Gly His Arg Pro Val Ile Asn Glu Glu Ser Leu Pro Tyr Asp Ile Pro
245                 250                 255                 260

cac cga gca cgt atg atc tct cta ata gaa agt gga tgg gca caa aat     1052
His Arg Ala Arg Met Ile Ser Leu Ile Glu Ser Gly Trp Ala Gln Asn
                265                 270                 275

cca gat gaa aga cca tct ttc tta aaa tgt tta ata gaa ctt gaa cca     1100
Pro Asp Glu Arg Pro Ser Phe Leu Lys Cys Leu Ile Glu Leu Glu Pro
            280                 285                 290

gtt ttg aga aca ttt gaa gag ata act ttt ctt gaa gct gtt att cag     1148
Val Leu Arg Thr Phe Glu Glu Ile Thr Phe Leu Glu Ala Val Ile Gln
        295                 300                 305

cta aag aaa aca aag tta cag agt gtt tca agt gcc att cac cta tgt     1196
Leu Lys Lys Thr Lys Leu Gln Ser Val Ser Ser Ala Ile His Leu Cys
    310                 315                 320

gac aag aag aaa atg gaa tta tct ctg aac ata cct gta aat cat ggt     1244
Asp Lys Lys Lys Met Glu Leu Ser Leu Asn Ile Pro Val Asn His Gly
325                 330                 335                 340

cca caa gag gaa tca tgt gga tcc tct cag ctc cat gaa aat agt ggt     1292
Pro Gln Glu Glu Ser Cys Gly Ser Ser Gln Leu His Glu Asn Ser Gly
                345                 350                 355

tct cct gaa act tca agg tcc ctg cca gct cct caa gac aat gat ttt     1340
Ser Pro Glu Thr Ser Arg Ser Leu Pro Ala Pro Gln Asp Asn Asp Phe
            360                 365                 370
```

```
tta tct aga aaa gct caa gac tgt tat ttt atg aag ctg cat cac tgt     1388
Leu Ser Arg Lys Ala Gln Asp Cys Tyr Phe Met Lys Leu His His Cys
        375                 380                 385

cct gga aat cac agt tgg gat agc acc att tct ggt tct caa agg gct     1436
Pro Gly Asn His Ser Trp Asp Ser Thr Ile Ser Gly Ser Gln Arg Ala
    390                 395                 400

gca ttc tgt gat cac aag acc act cca tgc tct tca gca ata ata aat     1484
Ala Phe Cys Asp His Lys Thr Thr Pro Cys Ser Ser Ala Ile Ile Asn
405                 410                 415                 420

cca ctc tca act gca gga aac tca gaa cgt ctg cag cct ggt ata gcc     1532
Pro Leu Ser Thr Ala Gly Asn Ser Glu Arg Leu Gln Pro Gly Ile Ala
                425                 430                 435

cag cag tgg atc cag agc aaa agg gaa gac att gtg aac caa atg aca     1580
Gln Gln Trp Ile Gln Ser Lys Arg Glu Asp Ile Val Asn Gln Met Thr
            440                 445                 450

gaa gcc tgc ctt aac cag tcg cta gat gcc ctt ctg tcc agg gac ttg     1628
Glu Ala Cys Leu Asn Gln Ser Leu Asp Ala Leu Leu Ser Arg Asp Leu
        455                 460                 465

atc atg aaa gag gac tat gaa ctt gtt agt acc aag cct aca agg acc     1676
Ile Met Lys Glu Asp Tyr Glu Leu Val Ser Thr Lys Pro Thr Arg Thr
    470                 475                 480

tca aaa gtc aga caa tta cta gac act act gac atc caa gga gaa gaa     1724
Ser Lys Val Arg Gln Leu Leu Asp Thr Thr Asp Ile Gln Gly Glu Glu
485                 490                 495                 500

ttt gcc aaa gtt ata gta caa aaa ttg aaa gat aac aaa caa atg ggt     1772
Phe Ala Lys Val Ile Val Gln Lys Leu Lys Asp Asn Lys Gln Met Gly
                505                 510                 515

ctt cag cct tac ccg gaa ata ctt gtg gtt tct aga tca cca tct tta     1820
Leu Gln Pro Tyr Pro Glu Ile Leu Val Val Ser Arg Ser Pro Ser Leu
            520                 525                 530

aat tta ctt caa aat aaa agc atg taa gtgactgttt ttcaagaaga           1867
Asn Leu Leu Gln Asn Lys Ser Met
        535                 540

aatgtgtttc ataaaaggat atttatatct ctgttgcttt gacttttttt atataaaatc   1927

cgtgagtatt aaagctttat tgaaggttct ttgggtaaat attagtctcc ctccatgaca   1987

ctgcagtatt ttttttaatt aatacaagta aaaagttgaa tttggttgaa tttgctacat   2047

agttcaattt ttatgtctct tttgttaaca gaaaccactt ttaaaggata gtaattattc   2107

ttgtttataa cagtgcctta aggtatgatg tatttctgat ggaagccatt ttcacattca   2167

tgttcttcat ggattatttg ttacttgtct aagatgcaat ttgattttat gaagtatata   2227

ccctttaccc accagagaca gtacagaatc cctgccctaa aatcccaggc ttaattgccc   2287

tacaaagggt tattaattta aaactccatt attaggatta cattttaaag ttttatttat   2347

gaattccctt taaaaatgat atttcaaagg taaaacaata caatataaag aaaaaaataa   2407

atatattaat accggcttcc tgtccccatt tttaacctca gccttcccta ctgtcaccaa   2467

caaccaagct aaataaagtc aacagcctga tgtg                               2501


<210> SEQ ID NO 36
<211> LENGTH: 540
<212> TYPE: PRT
<213> ORGANISM: Homo sapiens

<400> SEQUENCE: 36

Met Asn Gly Glu Ala Ile Cys Ser Ala Leu Pro Thr Ile Pro Tyr His
  1               5                  10                  15

Lys Leu Ala Asp Leu Arg Tyr Leu Ser Arg Gly Ala Ser Gly Thr Val
            20                  25                  30
```

```
Ser Ser Ala Arg His Ala Asp Trp Arg Val Gln Val Ala Val Lys His
        35                  40                  45

Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile Thr Phe Leu Glu
    290                 295                 300

Ala Val Ile Gln Leu Lys Lys Thr Lys Leu Gln Ser Val Ser Ser Ala
305                 310                 315                 320

Ile His Leu Cys Asp Lys Lys Lys Met Glu Leu Ser Leu Asn Ile Pro
                325                 330                 335

Val Asn His Gly Pro Gln Glu Glu Ser Cys Gly Ser Ser Gln Leu His
            340                 345                 350

Glu Asn Ser Gly Ser Pro Glu Thr Ser Arg Ser Leu Pro Ala Pro Gln
        355                 360                 365

Asp Asn Asp Phe Leu Ser Arg Lys Ala Gln Asp Cys Tyr Phe Met Lys
    370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Thr Pro Cys Ser Ser
                405                 410                 415

Ala Ile Ile Asn Pro Leu Ser Thr Ala Gly Asn Ser Glu Arg Leu Gln
            420                 425                 430

Pro Gly Ile Ala Gln Gln Trp Ile Gln Ser Lys Arg Glu Asp Ile Val
        435                 440                 445

Asn Gln Met Thr Glu Ala Cys Leu Asn Gln Ser Leu Asp Ala Leu Leu
```

```
    450                 455                 460

Ser Arg Asp Leu Ile Met Lys Glu Asp Tyr Glu Leu Val Ser Thr Lys
465                 470                 475                 480

Pro Thr Arg Thr Ser Lys Val Arg Gln Leu Leu Asp Thr Thr Asp Ile
                485                 490                 495

Gln Gly Glu Glu Phe Ala Lys Val Ile Val Gln Lys Leu Lys Asp Asn
            500                 505                 510

Lys Gln Met Gly Leu Gln Pro Tyr Pro Glu Ile Leu Val Val Ser Arg
        515                 520                 525

Ser Pro Ser Leu Asn Leu Leu Gln Asn Lys Ser Met
    530                 535                 540


<210> SEQ ID NO 37
<211> LENGTH: 1468
<212> TYPE: DNA
<213> ORGANISM: Cowpox virus
<220> FEATURE:
<221> NAME/KEY: CDS
<222> LOCATION: (295)..(1320)

<400> SEQUENCE: 37

tccatggaag aacgaaagta gtataaaagt aataaaacaa aaaaaagaat ataaaaaatt      60

tatagccact ttctttgagg actgttttcc tgaaggaaat gaacctctgg aattagttag     120

atatatagaa ttagtataca cgctagatta ttctcaaact cctaattatg acagactacg     180

tagactgttt atacaagatt gaaaatatat ttctttttat tgagtggtgg tagttacgga     240

tatctaatat taatattaga ctatctctat cgtcacacaa caaaatcgat tgcc atg       297
                                                            Met
                                                             1

gat atc ttc agg gaa atc gca tct tct atg aaa gga gag aat gta ttc       345
Asp Ile Phe Arg Glu Ile Ala Ser Ser Met Lys Gly Glu Asn Val Phe
            5                   10                  15

att tct cca ccg tca atc tcg tca gta ttg aca ata ctg tat tat gga       393
Ile Ser Pro Pro Ser Ile Ser Ser Val Leu Thr Ile Leu Tyr Tyr Gly
        20                  25                  30

gct aat gga tcc act gct gaa cag cta tca aaa tat gta gaa aag gag       441
Ala Asn Gly Ser Thr Ala Glu Gln Leu Ser Lys Tyr Val Glu Lys Glu
     35                  40                  45

gcg gac aag aat aag gat gat atc tca ttc aag tcc atg aat aaa gta       489
Ala Asp Lys Asn Lys Asp Asp Ile Ser Phe Lys Ser Met Asn Lys Val
 50                  55                  60                  65

tat ggg cga tat tct gca gtg ttt aaa gat tcc ttt ttg aga aaa att       537
Tyr Gly Arg Tyr Ser Ala Val Phe Lys Asp Ser Phe Leu Arg Lys Ile
                70                  75                  80

gga gat aat ttc caa act gtt gac ttc act gat tgt cgc act gta gat       585
Gly Asp Asn Phe Gln Thr Val Asp Phe Thr Asp Cys Arg Thr Val Asp
            85                  90                  95

gcg atc aac aag tgt gtt gat atc ttc act gag ggg aaa att aat cca       633
Ala Ile Asn Lys Cys Val Asp Ile Phe Thr Glu Gly Lys Ile Asn Pro
        100                 105                 110

cta ttg gat gaa cca ttg tct cca gat acc tgt ctc cta gca att agt       681
Leu Leu Asp Glu Pro Leu Ser Pro Asp Thr Cys Leu Leu Ala Ile Ser
    115                 120                 125

gcc gta tac ttt aaa gca aaa tgg ttg atg cca ttt gaa aag gaa ttt       729
Ala Val Tyr Phe Lys Ala Lys Trp Leu Met Pro Phe Glu Lys Glu Phe
130                 135                 140                 145

acc agt gat tat ccc ttt tac gta tct cca acg gaa atg gta gat gta       777
Thr Ser Asp Tyr Pro Phe Tyr Val Ser Pro Thr Glu Met Val Asp Val
                150                 155                 160
```

```
agt atg atg tct atg tac ggc gag gca ttt aat cac gca tct gta aaa      825
Ser Met Met Ser Met Tyr Gly Glu Ala Phe Asn His Ala Ser Val Lys
            165                 170                 175

gaa tca ttc ggc aac ttt tca atc ata gaa ctg cca tat gtt gga gat      873
Glu Ser Phe Gly Asn Phe Ser Ile Ile Glu Leu Pro Tyr Val Gly Asp
        180                 185                 190

act agt atg gtg gta att ctt cca gac aat att gat gga cta gaa tcc      921
Thr Ser Met Val Val Ile Leu Pro Asp Asn Ile Asp Gly Leu Glu Ser
    195                 200                 205

ata gaa caa aat cta aca gat aca aat ttt aag aaa tgg tgt gac tct      969
Ile Glu Gln Asn Leu Thr Asp Thr Asn Phe Lys Lys Trp Cys Asp Ser
210                 215                 220                 225

atg gat gct atg ttt atc gat gtg cac att ccc aag ttt aag gta aca     1017
Met Asp Ala Met Phe Ile Asp Val His Ile Pro Lys Phe Lys Val Thr
                230                 235                 240

ggc tcg tat aat ctg gtg gat gcg cta gta aag ttg gga ctg aca gag     1065
Gly Ser Tyr Asn Leu Val Asp Ala Leu Val Lys Leu Gly Leu Thr Glu
            245                 250                 255

gtg ttc ggt tca act gga gat tat agc aat atg tgt aat tca gat gtg     1113
Val Phe Gly Ser Thr Gly Asp Tyr Ser Asn Met Cys Asn Ser Asp Val
        260                 265                 270

agt gtc gac gct atg atc cac aaa acg tat ata gat gtc aat gaa gag     1161
Ser Val Asp Ala Met Ile His Lys Thr Tyr Ile Asp Val Asn Glu Glu
    275                 280                 285

tat aca gaa gca gct gca gca act tgt gcg ctg gtg gca gac tgt gca     1209
Tyr Thr Glu Ala Ala Ala Ala Thr Cys Ala Leu Val Ala Asp Cys Ala
290                 295                 300                 305

tca aca gtt aca aat gag ttc tgt gca gat cat ccg ttc atc tat gtg     1257
Ser Thr Val Thr Asn Glu Phe Cys Ala Asp His Pro Phe Ile Tyr Val
                310                 315                 320

att agg cat gtc gat ggc aaa att ctt ttc gtt ggt aga tat tgc tct     1305
Ile Arg His Val Asp Gly Lys Ile Leu Phe Val Gly Arg Tyr Cys Ser
            325                 330                 335

cca aca act aat taa atcacattct taatattaga atattagaat attatatagt     1360
Pro Thr Thr Asn
        340

taagattttt actaattggt taaccatttt tttaaaaaaa tagaaaaaaa acatgttata   1420

ttagcgaggg tcgttattct tccaattgca attggtaaga tgacggcc                1468


<210> SEQ ID NO 38
<211> LENGTH: 341
<212> TYPE: PRT
<213> ORGANISM: Cowpox virus

<400> SEQUENCE: 38

Met Asp Ile Phe Arg Glu Ile Ala Ser Ser Met Lys Gly Glu Asn Val
  1               5                  10                  15

Phe Ile Ser Pro Pro Ser Ile Ser Ser Val Leu Thr Ile Leu Tyr Tyr
             20                  25                  30

Gly Ala Asn Gly Ser Thr Ala Glu Gln Leu Ser Lys Tyr Val Glu Lys
         35                  40                  45

Glu Ala Asp Lys Asn Lys Asp Asp Ile Ser Phe Lys Ser Met Asn Lys
     50                  55                  60

Val Tyr Gly Arg Tyr Ser Ala Val Phe Lys Asp Ser Phe Leu Arg Lys
 65                  70                  75                  80

Ile Gly Asp Asn Phe Gln Thr Val Asp Phe Thr Asp Cys Arg Thr Val
                 85                  90                  95

Asp Ala Ile Asn Lys Cys Val Asp Ile Phe Thr Glu Gly Lys Ile Asn
            100                 105                 110
```

```
Pro Leu Leu Asp Glu Pro Leu Ser Pro Asp Thr Cys Leu Leu Ala Ile
        115                 120                 125

Ser Ala Val Tyr Phe Lys Ala Lys Trp Leu Met Pro Phe Glu Lys Glu
    130                 135                 140

Phe Thr Ser Asp Tyr Pro Phe Tyr Val Ser Pro Thr Glu Met Val Asp
145                 150                 155                 160

Val Ser Met Met Ser Met Tyr Gly Glu Ala Phe Asn His Ala Ser Val
                165                 170                 175

Lys Glu Ser Phe Gly Asn Phe Ser Ile Ile Glu Leu Pro Tyr Val Gly
            180                 185                 190

Asp Thr Ser Met Val Val Ile Leu Pro Asp Asn Ile Asp Gly Leu Glu
        195                 200                 205

Ser Ile Glu Gln Asn Leu Thr Asp Thr Asn Phe Lys Lys Trp Cys Asp
    210                 215                 220

Ser Met Asp Ala Met Phe Ile Asp Val His Ile Pro Lys Phe Lys Val
225                 230                 235                 240

Thr Gly Ser Tyr Asn Leu Val Asp Ala Leu Val Lys Leu Gly Leu Thr
                245                 250                 255

Glu Val Phe Gly Ser Thr Gly Asp Tyr Ser Asn Met Cys Asn Ser Asp
            260                 265                 270

Val Ser Val Asp Ala Met Ile His Lys Thr Tyr Ile Asp Val Asn Glu
        275                 280                 285

Glu Tyr Thr Glu Ala Ala Ala Ala Thr Cys Ala Leu Val Ala Asp Cys
    290                 295                 300

Ala Ser Thr Val Thr Asn Glu Phe Cys Ala Asp His Pro Phe Ile Tyr
305                 310                 315                 320

Val Ile Arg His Val Asp Gly Lys Ile Leu Phe Val Gly Arg Tyr Cys
                325                 330                 335

Ser Pro Thr Thr Asn
            340


<210> SEQ ID NO 39
<211> LENGTH: 5212
<212> TYPE: DNA
<213> ORGANISM: Homo sapiens
<220> FEATURE:
<221> NAME/KEY: CDS
<222> LOCATION: (2752)..(4566)

<400> SEQUENCE: 39

ggccaggcga caggtgtcgc ttgaaaagac tgggcttgtc cttgctggtg catgcgtcgt      60

cggcctctgg gcagcaggtt tacaaaggag gaaaacgact tcttctagat tttttttca      120

gtttcttcta taaatcaaaa catctcaaaa tggagaccta aaatccttaa agggacttag     180

tctaatctcg ggaggtagtt ttgtgcatgg gtaaacaaat taagtattaa ctggtgtttt     240

actatccaaa gaatgctaat tttataaaca tgatcgagtt atataaggta taccataatg     300

agtttgattt tgaatttgat ttgtggaaat aaaggaaaag tgattctagc tggggcatat     360

tgttaaagca ttttttcag agttggccag gcagtctcct actggcacat tctcccatta      420

tgtagaatag aaatagtacc tgtgtttggg aaagatttta aaatgagtga cagttatttg     480

gaacaaagag ctaataatca atccactgca aattaaagaa acatgcagat gaaagttttg     540

acacattaaa atacttctac agtgacaaag aaaaatcaag aacaaagctt tttgatatgt     600

gcaacaaatt tagaggaagt aaaaagataa atgtgatgat tggtcaagaa attatccagt     660

tatttacaag gccactgata ttttaaacgt ccaaaagttt gtttaaatgg gctgttaccg     720
```

```
ctgagaatga tgaggatgag aatgatggtt gaaggttaca ttttaggaaa tgaagaaact    780

tagaaaatta atataaagac agtgatgaat acaaagaaga tttttataac aatgtgtaaa    840

atttttggcc agggaaagga atattgaagt tagatacaat tacttacctt tgagggaaat    900

aattgttggt aatgagatgt gatgtttctc ctgccacctg gaaacaaagc attgaagtct    960

gcagttgaaa agcccaacgt ctgtgagatc caggaaacca tgcttgcaaa ccactggtaa   1020

aaaaaaaaaa aaaaaaaaaa aaaaagccac agtgacttgc ttattggtca ttgctagtat   1080

tatcgactca gaacctcttt actaatggct agtaaatcat aattgagaaa ttctgaattt   1140

tgacaaggtc tctgctgttg aaatggtaaa tttattattt tttttgtcat gataaattct   1200

ggttcaaggt atgctatcca tgaaataatt tctgaccaaa actaaattga tgcaatttga   1260

ttatccatct tagcctacag atggcatctg gtaacttttg actgttttaa aaataaatcc   1320

actatcagag tagatttgat gttggcttca gaaacatttt gaaaaacaaa agttcaaaaa   1380

tgttttcagg aggtgataag ttgaataact ctacaatgtt agttctttga gggggacaaa   1440

aaatttaaaa tctttgaaag gtcttatttt acagcccata tctaaattat cttaagaaaa   1500

tttttaacaa agggaatgaa atatatatca tgattctctt tttccaaaag taacctgaat   1560

atagctatga agttcagttt tgttattggt agtttgggca gagtctcttt ttgcagcacc   1620

tgttgtctac cataattaca gaggacattt ccatgttcta gccaagtata ctattagaat   1680

aaaaaaactt aacattgagt tgcttcaaca gcatgaaact gagtccaaaa gaccaaatga   1740

acaaacacat taatctctga ttatttattt taaatagaat atttaattgt gtaagatcta   1800

atagtatcat tatacttaag caatcatatt cctgatgatc tatgggaaat aactattatt   1860

taattaatat tgaaaccagg ttttaagatg tgttagccag tcctgttact agtaaatctc   1920

tttatttgga gagaaatttt agattgtttt gttctcctta ttagaaggat tgtagaaaga   1980

aaaaaatgac taattggaga aaaattgggg atatatcata tttcactgaa ttcaaaatgt   2040

cttcagttgt aaatcttacc attattttac gtacctctaa gaaataaaag tgcttctaat   2100

taaaatatga tgtcattaat tatgaaatac ttcttgataa cagaagtttt aaaatagcca   2160

tcttagaatc agtgaaatat ggtaatgtat tattttcctc ctttgagtta ggtcttgtgc   2220

tttttttccc tggccactaa atttcacaat ttccaaaaag caaaataaac atattctgaa   2280

tatttttgct gtgaaacact tgacagcaga gctttccacc atgaaaagaa gcttcatgag   2340

tcacacatta catctttggg ttgattgaat gccactgaaa cattctagta gcctggagaa   2400

gttgacctac ctgtggagat gcctgccatt aaatggcatc ctgatggctt aatacacatc   2460

actcttctgt gaagggtttt aattttcaac acagcttact ctgtagcatc atgtttacat   2520

tgtatgtata aagattatac aaaggtgcaa ttgtgtattt cttccttaaa atgtatcagt   2580

ataggattta gaatctccat gttgaaactc taaatgcata gaaataaaaa taataaaaaa   2640

tttttcattt tggcttttca gcctagtatt aaaactgata aaagcaaagc catgcacaaa   2700

actacctccc tagagaaagg ctagtccctt ttcttcccca ttcatttcat t atg aac     2757
                                                           Met Asn
                                                           1

ata gta gaa aac agc ata ttc tta tca aat ttg atg aaa agc gcc tac      2805
Ile Val Glu Asn Ser Ile Phe Leu Ser Asn Leu Met Lys Ser Ala Tyr
        5                   10                  15

acg ttt gaa ctg aaa tac gac ttg tca tgt gaa ctg tac cga atg tct      2853
Thr Phe Glu Leu Lys Tyr Asp Leu Ser Cys Glu Leu Tyr Arg Met Ser
    20                  25                  30

acg tat tcc act ttt cct gct ggg gtt cct gtc tca gaa agg agt ctt      2901
```

```
Thr Tyr Ser Thr Phe Pro Ala Gly Val Pro Val Ser Glu Arg Ser Leu
 35                 40                  45                  50

gct cgt gct ggt ttc tat tac act ggt gtg aat gac aag gtc aaa tgc     2949
Ala Arg Ala Gly Phe Tyr Tyr Thr Gly Val Asn Asp Lys Val Lys Cys
                55                  60                  65

ttc tgt tgt ggc ctg atg ctg gat aac tgg aaa aga gga gac agt cct     2997
Phe Cys Cys Gly Leu Met Leu Asp Asn Trp Lys Arg Gly Asp Ser Pro
            70                  75                  80

act gaa aag cat aaa aag ttg tat cct agc tgc aga ttc gtt cag agt     3045
Thr Glu Lys His Lys Lys Leu Tyr Pro Ser Cys Arg Phe Val Gln Ser
        85                  90                  95

cta aat tcc gtt aac aac ttg gaa gct acc tct cag cct act ttt cct     3093
Leu Asn Ser Val Asn Asn Leu Glu Ala Thr Ser Gln Pro Thr Phe Pro
    100                 105                 110

tct tca gta aca aat tcc aca cac tca tta ctt ccg ggt aca gaa aac     3141
Ser Ser Val Thr Asn Ser Thr His Ser Leu Leu Pro Gly Thr Glu Asn
115                 120                 125                 130

agt gga tat ttc cgt ggc tct tat tca aac tct cca tca aat cct gta     3189
Ser Gly Tyr Phe Arg Gly Ser Tyr Ser Asn Ser Pro Ser Asn Pro Val
                135                 140                 145

aac tcc aga gca aat caa gat ttt tct gcc ttg atg aga agt tcc tac     3237
Asn Ser Arg Ala Asn Gln Asp Phe Ser Ala Leu Met Arg Ser Ser Tyr
            150                 155                 160

cac tgt gca atg aat aac gaa aat gcc aga tta ctt act ttt cag aca     3285
His Cys Ala Met Asn Asn Glu Asn Ala Arg Leu Leu Thr Phe Gln Thr
        165                 170                 175

tgg cca ttg act ttt ctg tcg cca aca gat ctg gca aaa gca ggc ttt     3333
Trp Pro Leu Thr Phe Leu Ser Pro Thr Asp Leu Ala Lys Ala Gly Phe
    180                 185                 190

tac tac ata gga cct gga gac aga gtg gct tgc ttt gcc tgt ggt gga     3381
Tyr Tyr Ile Gly Pro Gly Asp Arg Val Ala Cys Phe Ala Cys Gly Gly
195                 200                 205                 210

aaa ttg agc aat tgg gaa ccg aag gat aat gct atg tca gaa cac ctg     3429
Lys Leu Ser Asn Trp Glu Pro Lys Asp Asn Ala Met Ser Glu His Leu
                215                 220                 225

aga cat ttt ccc aaa tgc cca ttt ata gaa aat cag ctt caa gac act     3477
Arg His Phe Pro Lys Cys Pro Phe Ile Glu Asn Gln Leu Gln Asp Thr
            230                 235                 240

tca aga tac aca gtt tct aat ctg agc atg cag aca cat gca gcc cgc     3525
Ser Arg Tyr Thr Val Ser Asn Leu Ser Met Gln Thr His Ala Ala Arg
        245                 250                 255

ttt aaa aca ttc ttt aac tgg ccc tct agt gtt cta gtt aat cct gag     3573
Phe Lys Thr Phe Phe Asn Trp Pro Ser Ser Val Leu Val Asn Pro Glu
    260                 265                 270

cag ctt gca agt gcg ggt ttt tat tat gtg ggt aac agt gat gat gtc     3621
Gln Leu Ala Ser Ala Gly Phe Tyr Tyr Val Gly Asn Ser Asp Asp Val
275                 280                 285                 290

aaa tgc ttt tgc tgt gat ggt gga ctc agg tgt tgg gaa tct gga gat     3669
Lys Cys Phe Cys Cys Asp Gly Gly Leu Arg Cys Trp Glu Ser Gly Asp
                295                 300                 305

gat cca tgg gtt caa cat gcc aag tgg ttt cca agg tgt gag tac ttg     3717
Asp Pro Trp Val Gln His Ala Lys Trp Phe Pro Arg Cys Glu Tyr Leu
            310                 315                 320

ata aga att aaa gga cag gag ttc atc cgt caa gtt caa gcc agt tac     3765
Ile Arg Ile Lys Gly Gln Glu Phe Ile Arg Gln Val Gln Ala Ser Tyr
        325                 330                 335

cct cat cta ctt gaa cag ctg cta tcc aca tca gac agc cca gga gat     3813
Pro His Leu Leu Glu Gln Leu Leu Ser Thr Ser Asp Ser Pro Gly Asp
    340                 345                 350

gaa aat gca gag tca tca att atc cat ttt gaa cct gga gaa gac cat     3861
```

```
Glu Asn Ala Glu Ser Ser Ile Ile His Phe Glu Pro Gly Glu Asp His
355                 360                 365                 370

tca gaa gat gca atc atg atg aat acc cct gtg att aat gct gcc gtg      3909
Ser Glu Asp Ala Ile Met Met Asn Thr Pro Val Ile Asn Ala Ala Val
                375                 380                 385

gaa atg ggc ttt agt aga agc ctg gta aaa cag aca gtt cag aga aaa      3957
Glu Met Gly Phe Ser Arg Ser Leu Val Lys Gln Thr Val Gln Arg Lys
            390                 395                 400

atc cta gca act gga gag aat tat aga cta gtc aat gat ctt gtg tta      4005
Ile Leu Ala Thr Gly Glu Asn Tyr Arg Leu Val Asn Asp Leu Val Leu
        405                 410                 415

gac tta ctc aat gca gaa gat gaa ata agg gaa gag gag aga gaa aga      4053
Asp Leu Leu Asn Ala Glu Asp Glu Ile Arg Glu Glu Glu Arg Glu Arg
    420                 425                 430

gca act gag gaa aaa gaa tca aat gat tta tta tta atc cgg aag aat      4101
Ala Thr Glu Glu Lys Glu Ser Asn Asp Leu Leu Leu Ile Arg Lys Asn
435                 440                 445                 450

aga atg gca ctt ttt caa cat ttg act tgt gta att cca atc ctg gat      4149
Arg Met Ala Leu Phe Gln His Leu Thr Cys Val Ile Pro Ile Leu Asp
                455                 460                 465

agt cta cta act gcc gga att att aat gaa caa gaa cat gat gtt att      4197
Ser Leu Leu Thr Ala Gly Ile Ile Asn Glu Gln Glu His Asp Val Ile
            470                 475                 480

aaa cag aag aca cag acg tct tta caa gca aga gaa ctg att gat acg      4245
Lys Gln Lys Thr Gln Thr Ser Leu Gln Ala Arg Glu Leu Ile Asp Thr
        485                 490                 495

att tta gta aaa gga aat att gca gcc act gta ttc aga aac tct ctg      4293
Ile Leu Val Lys Gly Asn Ile Ala Ala Thr Val Phe Arg Asn Ser Leu
    500                 505                 510

caa gaa gct gaa gct gtg tta tat gag cat tta ttt gtg caa cag gac      4341
Gln Glu Ala Glu Ala Val Leu Tyr Glu His Leu Phe Val Gln Gln Asp
515                 520                 525                 530

ata aaa tat att ccc aca gaa gat gtt tca gat cta cca gtg gaa gaa      4389
Ile Lys Tyr Ile Pro Thr Glu Asp Val Ser Asp Leu Pro Val Glu Glu
                535                 540                 545

caa ttg cgg aga cta caa gaa gaa aga aca tgt aaa gtg tgt atg gac      4437
Gln Leu Arg Arg Leu Gln Glu Glu Arg Thr Cys Lys Val Cys Met Asp
            550                 555                 560

aaa gaa gtg tcc ata gtg ttt att cct tgt ggt cat cta gta gta tgc      4485
Lys Glu Val Ser Ile Val Phe Ile Pro Cys Gly His Leu Val Val Cys
        565                 570                 575

aaa gat tgt gct cct tct tta aga aag tgt cct att tgt agg agt aca      4533
Lys Asp Cys Ala Pro Ser Leu Arg Lys Cys Pro Ile Cys Arg Ser Thr
    580                 585                 590

atc aag ggt aca gtt cgt aca ttt ctt tca tga agaagaacca aaacatcatc    4586
Ile Lys Gly Thr Val Arg Thr Phe Leu Ser
595                 600                 605

taaactttag aattaattta ttaaatgtat tataacttta acttttatcc taatttggtt   4646

tccttaaaat ttttatttat ttacaactca aaaaacattg ttttgtgtaa catatttata   4706

tatgtatcta aaccatatga acatatattt tttagaaact aagagaatga taggcttttg   4766

ttcttatgaa cgaaaaagag gtagcactac aaacacaata ttcaatcaaa atttcagcat   4826

tattgaaatt gtaagtgaag taaaacttaa gatatttgag ttaaccttta agaattttaa   4886

atattttggc attgtactaa taccgggaac atgaagccag gtgtggtggt atgtgcctgt   4946

agtcccaggc tgaggcaaga gaattacttg agcccaggag tttgaatcca tcctgggcag   5006

catactgaga ccctgccttt aaaaacaaac agaacaaaaa caaaacacca gggacacatt   5066

tctctgtctt ttttgatcag tgtcctatac atcgaaggtg tgcatatatg ttgaatgaca   5126
```

```
ttttagggac atggtgtttt tataaagaat tctgtgagaa aaaatttaat aaagcaacaa   5186

aaattactct taaaaaaaaa aaaaaa                                        5212


<210> SEQ ID NO 40
<211> LENGTH: 604
<212> TYPE: PRT
<213> ORGANISM: Homo sapiens

<400> SEQUENCE: 40

Met Asn Ile Val Glu Asn Ser Ile Phe Leu Ser Asn Leu Met Lys Ser
  1               5                  10                  15

Ala Tyr Thr Phe Glu Leu Lys Tyr Asp Leu Ser Cys Glu Leu Tyr Arg
             20                  25                  30

Met Ser Thr Tyr Ser Thr Phe Pro Ala Gly Val Pro Val Ser Glu Arg
         35                  40                  45

Ser Leu Ala Arg Ala Gly Phe Tyr Tyr Thr Gly Val Asn Asp Lys Val
     50                  55                  60

Lys Cys Phe Cys Cys Gly Leu Met Leu Asp Asn Trp Lys Arg Gly Asp
 65                  70                  75                  80

Ser Pro Thr Glu Lys His Lys Lys Leu Tyr Pro Ser Cys Arg Phe Val
                 85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
    290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
```

```
        355                 360                 365

Asp His Ser Glu Asp Ala Ile Met Met Asn Thr Pro Val Ile Asn Ala
    370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
        435                 440                 445

Lys Asn Arg Met Ala Leu Phe Gln His Leu Thr Cys Val Ile Pro Ile
    450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
        515                 520                 525

Gln Asp Ile Lys Tyr Ile Pro Thr Glu Asp Val Ser Asp Leu Pro Val
    530                 535                 540

Glu Glu Gln Leu Arg Arg Leu Gln Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
        595                 600


<210> SEQ ID NO 41
<211> LENGTH: 1034
<212> TYPE: DNA
<213> ORGANISM: Homo sapiens
<220> FEATURE:
<221> NAME/KEY: CDS
<222> LOCATION: (195)..(1034)

<400> SEQUENCE: 41

gacgcttctg ggagtgaggg gaagcggttt acgagtgact tggctggagc ctcaggggcg     60

ggcactggca cggaacacac cctgaggcca gccctggctg cccaggcgga gctgcctctt    120

ctcccgcggg ttggtggacc cgctcagtac ggagttgggg aagctctttc acttcggagg    180

attgctcaac aacc atg ctg ggc atc tgg acc ctc cta cct ctg gtt ctt      230
                Met Leu Gly Ile Trp Thr Leu Leu Pro Leu Val Leu
                1               5                   10

acg tct gtt gct aga tta tcg tcc aaa agt gtt aat gcc caa gtg act      278
Thr Ser Val Ala Arg Leu Ser Ser Lys Ser Val Asn Ala Gln Val Thr
        15                  20                  25

gac atc aac tcc aag gga ttg gaa ttg agg aag act gtt act aca gtt      326
Asp Ile Asn Ser Lys Gly Leu Glu Leu Arg Lys Thr Val Thr Thr Val
    30                  35                  40

gag act cag aac ttg gaa ggc ctg cat cat gat ggc caa ttc tgc cat      374
Glu Thr Gln Asn Leu Glu Gly Leu His His Asp Gly Gln Phe Cys His
45                  50                  55                  60
```

```
aag ccc tgt cct cca ggt gaa agg aaa gct agg gac tgc aca gtc aat      422
Lys Pro Cys Pro Pro Gly Glu Arg Lys Ala Arg Asp Cys Thr Val Asn
                65                  70                  75

ggg gat gaa cca gac tgc gtg ccc tgc caa gaa ggg aag gag tac aca      470
Gly Asp Glu Pro Asp Cys Val Pro Cys Gln Glu Gly Lys Glu Tyr Thr
            80                  85                  90

gac aaa gcc cat ttt tct tcc aaa tgc aga aga tgt aga ttg tgt gat      518
Asp Lys Ala His Phe Ser Ser Lys Cys Arg Arg Cys Arg Leu Cys Asp
        95                  100                 105

gaa gga cat ggc tta gaa gtg gaa ata aac tgc acc cgg acc cag aat      566
Glu Gly His Gly Leu Glu Val Glu Ile Asn Cys Thr Arg Thr Gln Asn
    110                 115                 120

acc aag tgc aga tgt aaa cca aac ttt ttt tgt aac tct act gta tgt      614
Thr Lys Cys Arg Cys Lys Pro Asn Phe Phe Cys Asn Ser Thr Val Cys
125                 130                 135                 140

gaa cac tgt gac cct tgc acc aaa tgt gaa cat gga atc atc aag gaa      662
Glu His Cys Asp Pro Cys Thr Lys Cys Glu His Gly Ile Ile Lys Glu
                145                 150                 155

tgc aca ctc acc agc aac acc aag tgc aaa gag gaa gga tcc aga tct      710
Cys Thr Leu Thr Ser Asn Thr Lys Cys Lys Glu Glu Gly Ser Arg Ser
            160                 165                 170

aac ttg ggg tgg ctt tgt ctt ctt ctt ttg cca att cca cta att gtt      758
Asn Leu Gly Trp Leu Cys Leu Leu Leu Leu Pro Ile Pro Leu Ile Val
        175                 180                 185

tgg gtg aag aga aag gaa gta cag aaa aca tgc aga aag cac aga aag      806
Trp Val Lys Arg Lys Glu Val Gln Lys Thr Cys Arg Lys His Arg Lys
    190                 195                 200

gaa aac caa ggt tct cat gaa tct cca acc tta aat cct gaa aca gtg      854
Glu Asn Gln Gly Ser His Glu Ser Pro Thr Leu Asn Pro Glu Thr Val
205                 210                 215                 220

gca ata aat tta tct gat gtt gac ttg agt aaa tat atc acc act att      902
Ala Ile Asn Leu Ser Asp Val Asp Leu Ser Lys Tyr Ile Thr Thr Ile
                225                 230                 235

gct gga gtc atg aca cta agt caa gtt aaa ggc ttt gtt cga aag aat      950
Ala Gly Val Met Thr Leu Ser Gln Val Lys Gly Phe Val Arg Lys Asn
            240                 245                 250

ggt gtc aat gaa gcc aaa ata gat gag atc aag aat gac aat gtc caa      998
Gly Val Asn Glu Ala Lys Ile Asp Glu Ile Lys Asn Asp Asn Val Gln
        255                 260                 265

gac aca gca gaa cag aaa gtt caa ctg ctt cgt aat                     1034
Asp Thr Ala Glu Gln Lys Val Gln Leu Leu Arg Asn
    270                 275                 280


<210> SEQ ID NO 42
<211> LENGTH: 280
<212> TYPE: PRT
<213> ORGANISM: Homo sapiens

<400> SEQUENCE: 42

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
```

```
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn
        275                 280
```

```
<210> SEQ ID NO 43
<211> LENGTH: 2056
<212> TYPE: DNA
<213> ORGANISM: Homo sapiens
<220> FEATURE:
<221> NAME/KEY: CDS
<222> LOCATION: (413)..(1750)

<400> SEQUENCE: 43

cgagtctcaa ctaaaaggga ctcccggagc taggggtggg gactcggcct cacacagtga     60

gtgccggcta ttggactttt gtccagtgac agctgagaca acaaggacca cgggaggagg    120

tgtaggagag aagcgccgcg aacagcgatc gcccagcacc aagtccgctt ccaggctttc    180

ggtttctttg cctccatctt gggtgcgcct tcccggcgtc taggggagcg aaggctgagg    240

tggcagcggc aggagagtcc ggccgcgaca ggacgaactc cccactgga aaggattctg    300

aaagaaatga agtcagccct cagaaatgaa gttgactgcc tgctggcttt ctgttgactg    360

gcccggagct gtactgcaag acccttgtga gcttccctag tctaagagta gg atg tct    418
                                                          Met Ser
                                                           1

gct gaa gtc atc cat cag gtt gaa gaa gca ctt gat aca gat gag aag      466
Ala Glu Val Ile His Gln Val Glu Glu Ala Leu Asp Thr Asp Glu Lys
        5                  10                  15

gag atg ctg ctc ttt ttg tgc cgg gat gtt gct ata gat gtg gtt cca      514
Glu Met Leu Leu Phe Leu Cys Arg Asp Val Ala Ile Asp Val Val Pro
    20                  25                  30

cct aat gtc agg gac ctt ctg gat att tta cgg gaa aga ggt aag ctg      562
Pro Asn Val Arg Asp Leu Leu Asp Ile Leu Arg Glu Arg Gly Lys Leu
 35                  40                  45                  50

tct gtc ggg gac ttg gct gaa ctg ctc tac aga gtg agg cga ttt gac      610
Ser Val Gly Asp Leu Ala Glu Leu Leu Tyr Arg Val Arg Arg Phe Asp
                55                  60                  65
```

```
ctg ctc aaa cgt atc ttg aag atg gac aga aaa gct gtg gag acc cac      658
Leu Leu Lys Arg Ile Leu Lys Met Asp Arg Lys Ala Val Glu Thr His
            70                  75                  80

ctg ctc agg aac cct cac ctt gtt tcg gac tat aga gtg ctg atg gca      706
Leu Leu Arg Asn Pro His Leu Val Ser Asp Tyr Arg Val Leu Met Ala
        85                  90                  95

gag att ggt gag gat ttg gat aaa tct gat gtg tcc tca tta att ttc      754
Glu Ile Gly Glu Asp Leu Asp Lys Ser Asp Val Ser Ser Leu Ile Phe
    100                 105                 110

ctc atg aag gat tac atg ggc cga ggc aag ata agc aag gag aag agt      802
Leu Met Lys Asp Tyr Met Gly Arg Gly Lys Ile Ser Lys Glu Lys Ser
115                 120                 125                 130

ttc ttg gac ctt gtg gtt gag ttg gag aaa cta aat ctg gtt gcc cca      850
Phe Leu Asp Leu Val Val Glu Leu Glu Lys Leu Asn Leu Val Ala Pro
            135                 140                 145

gat caa ctg gat tta tta gaa aaa tgc cta aag aac atc cac aga ata      898
Asp Gln Leu Asp Leu Leu Glu Lys Cys Leu Lys Asn Ile His Arg Ile
            150                 155                 160

gac ctg aag aca aaa atc cag aag tac aag cag tct gtt caa gga gca      946
Asp Leu Lys Thr Lys Ile Gln Lys Tyr Lys Gln Ser Val Gln Gly Ala
        165                 170                 175

ggg aca agt tac agg aat gtt ctc caa gca gca atc caa aag agt ctc      994
Gly Thr Ser Tyr Arg Asn Val Leu Gln Ala Ala Ile Gln Lys Ser Leu
    180                 185                 190

aag gat cct tca aat aac ttc agg agc ata cct gaa gag aga tac aag     1042
Lys Asp Pro Ser Asn Asn Phe Arg Ser Ile Pro Glu Glu Arg Tyr Lys
195                 200                 205                 210

atg aag agc aag ccc cta gga atc tgc ctg ata atc gat tgc att ggc     1090
Met Lys Ser Lys Pro Leu Gly Ile Cys Leu Ile Ile Asp Cys Ile Gly
            215                 220                 225

aat gag aca gag ctt ctt cga gac acc ttc act tcc ctg ggc tat gaa     1138
Asn Glu Thr Glu Leu Leu Arg Asp Thr Phe Thr Ser Leu Gly Tyr Glu
            230                 235                 240

gtc cag aaa ttc ttg cat ctc agt atg cat ggt ata tcc cag att ctt     1186
Val Gln Lys Phe Leu His Leu Ser Met His Gly Ile Ser Gln Ile Leu
        245                 250                 255

ggc caa ttt gcc tgt atg ccc gag cac cga gac tac gac agc ttt gtg     1234
Gly Gln Phe Ala Cys Met Pro Glu His Arg Asp Tyr Asp Ser Phe Val
    260                 265                 270

tgt gtc ctg gtg agc cga gga ggc tcc cag agt gtg tat ggt gtg gat     1282
Cys Val Leu Val Ser Arg Gly Gly Ser Gln Ser Val Tyr Gly Val Asp
275                 280                 285                 290

cag act cac tca ggg ctc ccc ctg cat cac atc agg agg atg ttc atg     1330
Gln Thr His Ser Gly Leu Pro Leu His His Ile Arg Arg Met Phe Met
            295                 300                 305

gga gat tca tgc cct tat cta gca ggg aag cca aag atg ttt ttt att     1378
Gly Asp Ser Cys Pro Tyr Leu Ala Gly Lys Pro Lys Met Phe Phe Ile
            310                 315                 320

cag aac tat gtg gtg tca gag ggc cag ctg gag gac agc agc ctc ttg     1426
Gln Asn Tyr Val Val Ser Glu Gly Gln Leu Glu Asp Ser Ser Leu Leu
        325                 330                 335

gag gtg gat ggg cca gcg atg aag aat gtg gaa ttc aag gct cag aag     1474
Glu Val Asp Gly Pro Ala Met Lys Asn Val Glu Phe Lys Ala Gln Lys
    340                 345                 350

cga ggg ctg tgc aca gtt cac cga gaa gct gac ttc ttc tgg agc ctg     1522
Arg Gly Leu Cys Thr Val His Arg Glu Ala Asp Phe Phe Trp Ser Leu
355                 360                 365                 370

tgt act gcg gac atg tcc ctg ctg gag cag tct cac agc tca ccg tcc     1570
Cys Thr Ala Asp Met Ser Leu Leu Glu Gln Ser His Ser Ser Pro Ser
            375                 380                 385
```

```
ctg tac ctg cag tgc ctc tcc cag aaa ctg aga caa gaa aga aaa cgc     1618
Leu Tyr Leu Gln Cys Leu Ser Gln Lys Leu Arg Gln Glu Arg Lys Arg
            390                 395                 400

cca ctc ctg gat ctt cac att gaa ctc aat ggc tac atg tat gat tgg     1666
Pro Leu Leu Asp Leu His Ile Glu Leu Asn Gly Tyr Met Tyr Asp Trp
        405                 410                 415

aac agc aga gtt tct gcc aag gag aaa tat tat gtt tgg ctg cag cac     1714
Asn Ser Arg Val Ser Ala Lys Glu Lys Tyr Tyr Val Trp Leu Gln His
    420                 425                 430

act ctg aga aag aaa ctt atc ctc tcc tac aca taa gaaaccaaaa          1760
Thr Leu Arg Lys Lys Leu Ile Leu Ser Tyr Thr
435                 440                 445

ggctgggcgt agtggctcac acctgtaatc ccagcacttt gggaggccaa ggagggcaga   1820

tcacttcagg tcaggagttc gagaccagcc tggccaacat ggtaaacgct gtccctagta   1880

aaaatacaaa aattagctgg gtgtgggtgt gggtacctgt attcccagtt acttgggagg   1940

ctgaggtggg aggatctttt gaacccagga gttcagggtc atagcatgct gtgattgtgc   2000

ctacgaatag ccactgcata ccaacctggg caatatagca agatcccatc tcttta       2056


<210> SEQ ID NO 44
<211> LENGTH: 445
<212> TYPE: PRT
<213> ORGANISM: Homo sapiens

<400> SEQUENCE: 44

Met Ser Ala Glu Val Ile His Gln Val Glu Glu Ala Leu Asp Thr Asp
  1               5                  10                  15

Glu Lys Glu Met Leu Leu Phe Leu Cys Arg Asp Val Ala Ile Asp Val
             20                  25                  30

Val Pro Pro Asn Val Arg Asp Leu Leu Asp Ile Leu Arg Glu Arg Gly
         35                  40                  45

Lys Leu Ser Val Gly Asp Leu Ala Glu Leu Leu Tyr Arg Val Arg Arg
     50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                 85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Ser Ile Pro Glu Glu Arg
        195                 200                 205

Tyr Lys Met Lys Ser Lys Pro Leu Gly Ile Cys Leu Ile Ile Asp Cys
    210                 215                 220

Ile Gly Asn Glu Thr Glu Leu Leu Arg Asp Thr Phe Thr Ser Leu Gly
225                 230                 235                 240
```

```
Tyr Glu Val Gln Lys Phe Leu His Leu Ser Met His Gly Ile Ser Gln
                245                 250                 255

Ile Leu Gly Gln Phe Ala Cys Met Pro Glu His Arg Asp Tyr Asp Ser
            260                 265                 270

Phe Val Cys Val Leu Val Ser Arg Gly Gly Ser Gln Ser Val Tyr Gly
        275                 280                 285

Val Asp Gln Thr His Ser Gly Leu Pro Leu His His Ile Arg Arg Met
    290                 295                 300

Phe Met Gly Asp Ser Cys Pro Tyr Leu Ala Gly Lys Pro Lys Met Phe
305                 310                 315                 320

Phe Ile Gln Asn Tyr Val Val Ser Glu Gly Gln Leu Glu Asp Ser Ser
                325                 330                 335

Leu Leu Glu Val Asp Gly Pro Ala Met Lys Asn Val Glu Phe Lys Ala
            340                 345                 350

Gln Lys Arg Gly Leu Cys Thr Val His Arg Glu Ala Asp Phe Phe Trp
        355                 360                 365

Ser Leu Cys Thr Ala Asp Met Ser Leu Leu Glu Gln Ser His Ser Ser
    370                 375                 380

Pro Ser Leu Tyr Leu Gln Cys Leu Ser Gln Lys Leu Arg Gln Glu Arg
385                 390                 395                 400

Lys Arg Pro Leu Leu Asp Leu His Ile Glu Leu Asn Gly Tyr Met Tyr
                405                 410                 415

Asp Trp Asn Ser Arg Val Ser Ala Lys Glu Lys Tyr Tyr Val Trp Leu
            420                 425                 430

Gln His Thr Leu Arg Lys Lys Leu Ile Leu Ser Tyr Thr
        435                 440                 445


<210> SEQ ID NO 45
<211> LENGTH: 5086
<212> TYPE: DNA
<213> ORGANISM: Homo sapiens
<220> FEATURE:
<221> NAME/KEY: CDS
<222> LOCATION: (1459)..(2178)

<400> SEQUENCE: 45

gcgcccgccc ctccgcgccg cctgcccgcc cgcccgccgc gctcccgccc gccgctctcc      60

gtggccccgc cgcgctgccg ccgccgccgc tgccagcgaa ggtgccgggg ctccgggccc     120

tccctgccgg cggccgtcag cgctcggagc gaactgcgcg acgggaggtc cgggaggcga     180

ccgtagtcgc gccgccgcgc aggaccagga ggaggagaaa gggtgcgcag cccggaggcg     240

gggtgcgccg gtggggtgca gcggaagagg gggtccaggg gggagaactt cgtagcagtc     300

atcctttta ggaaaagagg gaaaaaataa aaccctcccc caccacctcc ttctccccac     360

ccctcgccgc accacacaca gcgcgggctt ctagcgctcg gcaccggcgg gccaggcgcg     420

tcctgccttc atttatccag cagcttttcg gaaaatgcat ttgctgttcg gagtttaatc     480

agaagacgat tcctgcctcc gtccccggct ccttcatcgt cccatctccc ctgtctctct     540

cctggggagg cgtgaagcgg tcccgtggat agagattcat gcctgtgtcc gcgcgtgtgt     600

gcgcgcgtat aaattgccga gaaggggaaa acatcacagg acttctgcga ataccggact     660

gaaaattgta attcatctgc cgccgccgct gccaaaaaaa aactcgagct cttgagatct     720

ccggttggga ttcctgcgga ttgacatttc tgtgaagcag aagtctggga atcgatctgg     780

aaatcctcct aatttttact ccctctcccc ccgactcctg attcattggg aagtttcaaa     840

tcagctataa ctggagagtg ctgaagattg atgggatcgt tgccttatgc atttgttttg     900
```

```
gttttacaaa aaggaaactt gacagaggat catgctgtac ttaaaaaata caagtaagtc    960

tcgcacagga aattggttta atgtaacttt caatggaaac ctttgagatt ttttacttaa   1020

agtgcattcg agtaaattta atttccaggc agcttaatac attgttttta gccgtgttac   1080

ttgtagtgtg tatgccctgc tttcactcag tgtgtacagg gaaacgcacc tgattttttta  1140

cttattagtt tgttttttct ttaacctttc agcatcacag aggaagtaga ctgatattaa   1200

caatacttac taataataac gtgcctcatg aaataaagat ccgaaaggaa ttggaataaa   1260

aatttcctgc gtctcatgcc aagagggaaa caccagaatc aagtgttccg cgtgattgaa   1320

gacacccccct cgtccaagaa tgcaaagcac atccaataaa atagctggat tataactcct  1380

cttctttctc tgggggccgt ggggtgggag ctggggcgag aggtgccgtt ggcccccgtt   1440

gcttttcctc tgggaagg atg gcg cac gct ggg aga acg ggg tac gac aac     1491
                    Met Ala His Ala Gly Arg Thr Gly Tyr Asp Asn
                      1               5                  10

cgg gag ata gtg atg aag tac atc cat tat aag ctg tcg cag agg ggc     1539
Arg Glu Ile Val Met Lys Tyr Ile His Tyr Lys Leu Ser Gln Arg Gly
            15                  20                  25

tac gag tgg gat gcg gga gat gtg ggc gcc gcg ccc ccg ggg gcc gcc     1587
Tyr Glu Trp Asp Ala Gly Asp Val Gly Ala Ala Pro Pro Gly Ala Ala
        30                  35                  40

ccc gca ccg ggc atc ttc tcc tcc cag ccc ggg cac acg ccc cat cca     1635
Pro Ala Pro Gly Ile Phe Ser Ser Gln Pro Gly His Thr Pro His Pro
    45                  50                  55

gcc gca tcc cgc gac ccg gtc gcc agg acc tcg ccg ctg cag acc ccg     1683
Ala Ala Ser Arg Asp Pro Val Ala Arg Thr Ser Pro Leu Gln Thr Pro
 60                  65                  70                  75

gct gcc ccc ggc gcc gcc gcg ggg cct gcg ctc agc ccg gtg cca cct     1731
Ala Ala Pro Gly Ala Ala Ala Gly Pro Ala Leu Ser Pro Val Pro Pro
                80                  85                  90

gtg gtc cac ctg gcc ctc cgc caa gcc ggc gac gac ttc tcc cgc cgc     1779
Val Val His Leu Ala Leu Arg Gln Ala Gly Asp Asp Phe Ser Arg Arg
            95                 100                 105

tac cgc ggc gac ttc gcc gag atg tcc agc cag ctg cac ctg acg ccc     1827
Tyr Arg Gly Asp Phe Ala Glu Met Ser Ser Gln Leu His Leu Thr Pro
        110                 115                 120

ttc acc gcg cgg gga cgc ttt gcc acg gtg gtg gag gag ctc ttc agg     1875
Phe Thr Ala Arg Gly Arg Phe Ala Thr Val Val Glu Glu Leu Phe Arg
    125                 130                 135

gac ggg gtg aac tgg ggg agg att gtg gcc ttc ttt gag ttc ggt ggg     1923
Asp Gly Val Asn Trp Gly Arg Ile Val Ala Phe Phe Glu Phe Gly Gly
140                 145                 150                 155

gtc atg tgt gtg gag agc gtc aac cgg gag atg tcg ccc ctg gtg gac     1971
Val Met Cys Val Glu Ser Val Asn Arg Glu Met Ser Pro Leu Val Asp
                160                 165                 170

aac atc gcc ctg tgg atg act gag tac ctg aac cgg cac ctg cac acc     2019
Asn Ile Ala Leu Trp Met Thr Glu Tyr Leu Asn Arg His Leu His Thr
            175                 180                 185

tgg atc cag gat aac gga ggc tgg gat gcc ttt gtg gaa ctg tac ggc     2067
Trp Ile Gln Asp Asn Gly Gly Trp Asp Ala Phe Val Glu Leu Tyr Gly
        190                 195                 200

ccc agc atg cgg cct ctg ttt gat ttc tcc tgg ctg tct ctg aag act     2115
Pro Ser Met Arg Pro Leu Phe Asp Phe Ser Trp Leu Ser Leu Lys Thr
    205                 210                 215

ctg ctc agt ttg gcc ctg gtg gga gct tgc atc acc ctg ggt gcc tat     2163
Leu Leu Ser Leu Ala Leu Val Gly Ala Cys Ile Thr Leu Gly Ala Tyr
220                 225                 230                 235

ctg agc cac aag tga agtcaacatg cctgccccaa acaaatatgc aaaaggttca     2218
Leu Ser His Lys
```

```
                240

ctaaagcagt agaaataata tgcattgtca gtgatgtacc atgaaacaaa gctgcaggct   2278
gtttaagaaa aaataacaca catataaaca tcacacacac agacagacac acacacacac   2338
aacaattaac agtcttcagg caaaacgtcg aatcagctat ttactgccaa agggaaatat   2398
catttatttt ttacattatt aagaaaaaag atttatttat ttaagacagt cccatcaaaa   2458
ctccgtcttt ggaaatccga ccactaattg ccaaacaccg cttcgtgtgg ctccacctgg   2518
atgttctgtg cctgtaaaca tagattcgct ttccatgttg ttggccggat caccatctga   2578
agagcagacg gatggaaaaa ggacctgatc attggggaag ctggctttct ggctgctgga   2638
ggctggggag aaggtgttca ttcacttgca tttctttgcc ctgggggcgt gatattaaca   2698
gagggagggt tcccgtgggg ggaagtccat gcctccctgg cctgaagaag agactctttg   2758
catatgactc acatgatgca tacctggtgg gaggaaaaga gttgggaact tcagatggac   2818
ctagtaccca ctgagatttc cacgccgaag gacagcgatg ggaaaaatgc ccttaaatca   2878
taggaaagta ttttttaag ctaccaattg tgccgagaaa agcattttag caatttatac   2938
aatatcatcc agtaccttaa accctgattg tgtatattca tatattttgg atacgcaccc   2998
cccaactccc aatactggct ctgtctgagt aagaaacaga atcctctgga acttgaggaa   3058
gtgaacattt cggtgacttc cgatcaggaa ggctagagtt acccagagca tcaggccgcc   3118
acaagtgcct gcttttagga gaccgaagtc cgcagaacct acctgtgtcc cagcttggag   3178
gcctggtcct ggaactgagc cgggccctca ctggcctcct ccagggatga tcaacagggt   3238
agtgtggtct ccgaatgtct ggaagctgat ggatggagct cagaattcca ctgtcaagaa   3298
agagcagtag aggggtgtgg ctgggcctgt caccctgggg ccctccaggt aggcccgttt   3358
tcacgtggag cataggagcc acgacccttc ttaagacatg tatcactgta gagggaagga   3418
acagaggccc tgggccttcc tatcagaagg acatggtgaa ggctgggaac gtgaggagag   3478
gcaatggcca cggcccattt tggctgtagc acatggcacg ttggctgtgt ggccttggcc   3538
acctgtgagt ttaaagcaag gctttaaatg actttggaga gggtcacaaa tcctaaaaga   3598
agcattgaag tgaggtgtca tggattaatt gacccctgtc tatggaatta catgtaaaac   3658
attatcttgt cactgtagtt tggttttatt tgaaaacctg acaaaaaaaa agttccaggt   3718
gtggaatatg gggttatct gtacatcctg gggcattaaa aaaaaatcaa tggtggggaa   3778
ctataaagaa gtaacaaaag aagtgacatc ttcagcaaat aaactaggaa attttttttt   3838
cttccagttt agaatcagcc ttgaaacatt gatggaataa ctctgtggca ttattgcatt   3898
atataccatt tatctgtatt aactttggaa tgtactctgt tcaatgttta atgctgtggt   3958
tgatatttcg aaagctgctt taaaaaaata catgcatctc agcgtttttt tgtttttaat   4018
tgtatttagt tatggcctat acactatttg tgagcaaagg tgatcgtttt ctgtttgaga   4078
tttttatctc ttgattcttc aaaagcattc tgagaaggtg agataagccc tgagtctcag   4138
ctacctaaga aaaacctgga tgtcactggc cactgaggag ctttgtttca accaagtcat   4198
gtgcatttcc acgtcaacag aattgtttat tgtgacagtt atatctgttg tccctttgac   4258
cttgtttctt gaaggtttcc tcgtccctgg gcaattccgc atttaattca tggtattcag   4318
gattacatgc atgtttggtt aaacccatga gattcattca gttaaaaatc cagatggcga   4378
atgaccagca gattcaaatc tatggtggtt tgacctttag agagttgctt tacgtggcct   4438
gtttcaacac agacccaccc agagccctcc tgccctcctt ccgcgggggc tttctcatgg   4498
ctgtccttca gggtcttcct gaaatgcagt ggtcgttacg ctccaccaag aaagcaggaa   4558
```

```
acctgtggta tgaagccaga cctccccggc gggcctcagg gaacagaatg atcagacctt   4618

tgaatgattc taatttttaa gcaaaatatt attttatgaa aggtttacat tgtcaaagtg   4678

atgaatatgg aatatccaat cctgtgctgc tatcctgcca aaatcatttt aatggagtca   4738

gtttgcagta tgctccacgt ggtaagatcc tccaagctgc tttagaagta acaatgaaga   4798

acgtggacgt ttttaatata aagcctgttt tgtcttttgt tgttgttcaa acgggattca   4858

cagagtattt gaaaaatgta tatatattaa gaggtcacgg gggctaattg ctagctggct   4918

gccttttgct gtggggtttt gttacctggt tttaataaca gtaaatgtgc ccagcctctt   4978

ggccccagaa ctgtacagta ttgtggctgc acttgctcta agagtagttg atgttgcatt   5038

ttccttattg ttaaaaacat gttagaagca atgaatgtat ataaaagc                5086
```

```
<210> SEQ ID NO 46
<211> LENGTH: 239
<212> TYPE: PRT
<213> ORGANISM: Homo sapiens

<400> SEQUENCE: 46

Met Ala His Ala Gly Arg Thr Gly Tyr Asp Asn Arg Glu Ile Val Met
  1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Ala
                 85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235
```

```
<210> SEQ ID NO 47
<211> LENGTH: 926
<212> TYPE: DNA
<213> ORGANISM: Homo sapiens
<220> FEATURE:
<221> NAME/KEY: CDS
<222> LOCATION: (135)..(836)
```

```
<400> SEQUENCE: 47

gaatctcttt ctctcccttc agaatcttat cttggctttg gatcttagaa gagaatcact      60

aaccagagac gagactcagt gagtgagcag gtgttttgga caatggactg gttgagccca     120

tccctattat aaaa atg tct cag agc aac cgg gag ctg gtg gtt gac ttt       170
                Met Ser Gln Ser Asn Arg Glu Leu Val Val Asp Phe
                1               5                   10

ctc tcc tac aag ctt tcc cag aaa gga tac agc tgg agt cag ttt agt       218
Leu Ser Tyr Lys Leu Ser Gln Lys Gly Tyr Ser Trp Ser Gln Phe Ser
        15                  20                  25

gat gtg gaa gag aac agg act gag gcc cca gaa ggg act gaa tcg gag       266
Asp Val Glu Glu Asn Arg Thr Glu Ala Pro Glu Gly Thr Glu Ser Glu
    30                  35                  40

atg gag acc ccc agt gcc atc aat ggc aac cca tcc tgg cac ctg gca       314
Met Glu Thr Pro Ser Ala Ile Asn Gly Asn Pro Ser Trp His Leu Ala
45                  50                  55                  60

gac agc ccc gcg gtg aat gga gcc act gcg cac agc agc agt ttg gat       362
Asp Ser Pro Ala Val Asn Gly Ala Thr Ala His Ser Ser Ser Leu Asp
                65                  70                  75

gcc cgg gag gtg atc ccc atg gca gca gta aag caa gcg ctg agg gag       410
Ala Arg Glu Val Ile Pro Met Ala Ala Val Lys Gln Ala Leu Arg Glu
            80                  85                  90

gca ggc gac gag ttt gaa ctg cgg tac cgg cgg gca ttc agt gac ctg       458
Ala Gly Asp Glu Phe Glu Leu Arg Tyr Arg Arg Ala Phe Ser Asp Leu
        95                  100                 105

aca tcc cag ctc cac atc acc cca ggg aca gca tat cag agc ttt gaa       506
Thr Ser Gln Leu His Ile Thr Pro Gly Thr Ala Tyr Gln Ser Phe Glu
    110                 115                 120

cag gta gtg aat gaa ctc ttc cgg gat ggg gta aac tgg ggt cgc att       554
Gln Val Val Asn Glu Leu Phe Arg Asp Gly Val Asn Trp Gly Arg Ile
125                 130                 135                 140

gtg gcc ttt ttc tcc ttc ggc ggg gca ctg tgc gtg gaa agc gta gac       602
Val Ala Phe Phe Ser Phe Gly Gly Ala Leu Cys Val Glu Ser Val Asp
                145                 150                 155

aag gag atg cag gta ttg gtg agt cgg atc gca gct tgg atg gcc act       650
Lys Glu Met Gln Val Leu Val Ser Arg Ile Ala Ala Trp Met Ala Thr
            160                 165                 170

tac ctg aat gac cac cta gag cct tgg atc cag gag aac ggc ggc tgg       698
Tyr Leu Asn Asp His Leu Glu Pro Trp Ile Gln Glu Asn Gly Gly Trp
        175                 180                 185

gat act ttt gtg gaa ctc tat ggg aac aat gca gca gcc gag agc cga       746
Asp Thr Phe Val Glu Leu Tyr Gly Asn Asn Ala Ala Ala Glu Ser Arg
    190                 195                 200

aag ggc cag gaa cgc ttc aac cgc tgg ttc ctg acg ggc atg act gtg       794
Lys Gly Gln Glu Arg Phe Asn Arg Trp Phe Leu Thr Gly Met Thr Val
205                 210                 215                 220

gcc ggc gtg gtt ctg ctg ggc tca ctc ttc agt cgg aaa tga               836
Ala Gly Val Val Leu Leu Gly Ser Leu Phe Ser Arg Lys
                225                 230

ccagacactg accatccact ctaccctccc acccccttct ctgctccacc acatcctccg     896

tccagccgcc attgccacca ggagaacccg                                      926


<210> SEQ ID NO 48
<211> LENGTH: 233
<212> TYPE: PRT
<213> ORGANISM: Homo sapiens

<400> SEQUENCE: 48

Met Ser Gln Ser Asn Arg Glu Leu Val Val Asp Phe Leu Ser Tyr Lys
1               5                   10                  15
```

```
Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Ala His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

```
<210> SEQ ID NO 49
<211> LENGTH: 4006
<212> TYPE: DNA
<213> ORGANISM: human adenovirus type 9
<220> FEATURE:
<221> NAME/KEY: CDS
<222> LOCATION: (1569)..(2117)

<400> SEQUENCE: 49

ctatctatat aatataccccc acaaagtaaa caaaagttaa tatgcaaatg agcttttgaa     60

ttttaacggt ttcgggcgga gccaacgctg attggacgag agaagacgat gcaaatgacg    120

tcacgactgc acggctaacg gtcgccgcgg aggcgtggcc tagcccggaa gcaagtcgcg    180

gggctgatga cgtataaaaa agcggacttt agacccggaa acggccgatt ttcccgcgcc    240

acgcccggat atgaggtaat tctgggcgga tgcaagtgaa attaggtcat tttggcgcga    300

aaactgaatg aggaagtgaa aagcgaaaaa taccggtccc tcccagggcg gaatatttac    360

cgagggccga gagactttga ccgattacgt gggggtttcg attgcggtgt ttttttcgcg    420

aatttccgcg tccgtgtcaa agtccggtgt ttatgtcaca gatcagctga tccgcaggta    480

tttaaaccag tcgagtccgt caagaggcca ctcttgagtg ccagcgagta gagatttctc    540

tgagctccgc tcccagagac cgagaaaaat gagacacctg cgcctcctgc cttcaactgt    600

gcccggtgag ctggctgtgc ttatgctgga ggactttgtg gatacagtat tggaggacga    660

actgcatcca agtccgttcg agctgggacc cacacttcag gatctctatg atctggaggt    720

agatgcccat gatgacgacc ctaacgagga ggctgtgaat ttaatatttc cagaatctat    780
```

-continued

```
gattcttcag gctgacatag ccaacgaatc tactccactt catacaccga ctctgtcacc    840

catacctgaa ttggaagagg aggacgaact agacctccgg tgttatgagg aaggttttcc    900

tcccagcgat tcagaggatg aacggggtga gcagaccatg gctctgatct cagactatgc    960

ttgtgtgatt gtggaggagc aagatgtgat tgaaaaatct actgagccag tacaaggctg   1020

taggaactgc cagtaccacc gggataagtc cggagatgtg aacgcctcct gcgctttgtg   1080

ctatatgaaa cagactttca gctttattta cagtaagtgg agtgaatgtg agagaggctg   1140

agtgcttaac acataactgt aatgcttgaa cagctgtgct aagtgtggtt tattttgtta   1200

ctaggtccgg tgtcagagga tgagttatca ccctcagaag aagaccaccc gtctccccct   1260

gagctgtcag gcgaaacgcc cctgcaagtg ttcagaccca ccccagtcag acccagtggc   1320

gagaggcgag cggctgttga caaaattgag gacttgttgc aggacatggg tggggatgaa   1380

cctttggacc tgagcttgaa acgccccagg aactagacgc acgtgcgctt agtcatgtgt   1440

aaataaagtt gtacaataaa agtctatgtg acgcatgcaa ggtgtggttt atgactcatg   1500

ggcggggctt agtcctatat aagtggcaac acctgggcac ttgggcacag accttcaggg   1560

agttcctg atg gat gtg tgg act atc ctt gca gac ttt agc aag aca cgc    1610
         Met Asp Val Trp Thr Ile Leu Ala Asp Phe Ser Lys Thr Arg
           1               5                  10

cgg ctt gta gag gat agt tca gac ggg tgc tcc ggg ttc tgg aga cac     1658
Arg Leu Val Glu Asp Ser Ser Asp Gly Cys Ser Gly Phe Trp Arg His
 15                  20                  25                  30

tgg ttt gga act cct cta tct cgc ctg gtg tac aca gtt aag aag gat     1706
Trp Phe Gly Thr Pro Leu Ser Arg Leu Val Tyr Thr Val Lys Lys Asp
                 35                  40                  45

tat aaa gag gaa ttt gaa aat att ttt gct gac tgc tct ggc ctg cta     1754
Tyr Lys Glu Glu Phe Glu Asn Ile Phe Ala Asp Cys Ser Gly Leu Leu
             50                  55                  60

gat tct ctg aat ctt ggc cac cag tcc ctt ttc cag gaa agg gta ctc     1802
Asp Ser Leu Asn Leu Gly His Gln Ser Leu Phe Gln Glu Arg Val Leu
         65                  70                  75

cac agc ctt gat ttt tcc agc cca ggg cgc act aca gcc ggg gtt gct     1850
His Ser Leu Asp Phe Ser Ser Pro Gly Arg Thr Thr Ala Gly Val Ala
     80                  85                  90

ttt gtg gtt ttt ctg gtt gac aaa tgg agc cag gac acc caa ctg agc     1898
Phe Val Val Phe Leu Val Asp Lys Trp Ser Gln Asp Thr Gln Leu Ser
 95                 100                 105                 110

agg ggc tac atc ctg gac ttc gca gcc atg cac ctg tgg agg gcc tgg     1946
Arg Gly Tyr Ile Leu Asp Phe Ala Ala Met His Leu Trp Arg Ala Trp
                115                 120                 125

atc agg cag cgg gga cag aga atc ttg aat tac tgg ctt cta cag cca     1994
Ile Arg Gln Arg Gly Gln Arg Ile Leu Asn Tyr Trp Leu Leu Gln Pro
            130                 135                 140

gca gct ccg ggt ctt ctt cgt cta cac aga caa aca tcc atg ttg gag     2042
Ala Ala Pro Gly Leu Leu Arg Leu His Arg Gln Thr Ser Met Leu Glu
        145                 150                 155

gaa gaa atg agg cag gcc atg gac gag aac ccg agg agc ggc ctg gac     2090
Glu Glu Met Arg Gln Ala Met Asp Glu Asn Pro Arg Ser Gly Leu Asp
    160                 165                 170

cct ccg tcg gaa gag gag ctg gat tga atcaggtatc cagcctgtac           2137
Pro Pro Ser Glu Glu Glu Leu Asp
175                 180

ccagagctta gcaaggtgct gacatccatg gccaggggag ttaagaggga gaggagcgat   2197

gggggtaata ccgggatgat gaccgagctg acggccagcc tgatgaatcg gaaacgccca   2257

gagcgcctta cctggtacga gctacagcag gagtgcaggg atgagttggg cctgatgcag   2317
```

```
gataaatatg gcctggagca gataaaaacc cattggttga acccagatga ggattgggag   2377

gaggctatta agaagtatgc caagatagcc ctgcgcccag attgcaagta catagtgacc   2437

aagaccgtga atatcagaca tgcctgctac atctcgggga acggggcaga ggtggtcatc   2497

gataccctgg acaaggccgc cttcaggtgt tgcatgatgg gaatgagagc aggagtgatg   2557

aatatgaatt ccatgatctt catgaacatg aagttcaatg gagagaagtt taatggggtg   2617

ctgttcatgg ccaacagcca gatgaccctg catggctgca gtttcttcgg cttcaacaat   2677

atgtgcgcag aggtctgggg cgcttccaag atcaggggat gtaagtttta tggctgctgg   2737

atgggcgtgg tcggaagacc agagagcgag atgtctgtga agcagtgtgt gtttgagaaa   2797

tgctacctgg gagtctctac cgagggcaat gctagagtga gacactgctc ttccctggag   2857

acgggctgct tctgcctggt gaagggcaca gcctctctga agcataacat ggtgaagggc   2917

tgcacggatg agcgcatgta caacatgctg acctgcgatt cgggggtctg ccatatcctg   2977

aagaacatcc atgtgacctc ccaccccaga aagaagtggc cagtgtttga gaataacctg   3037

ctgatcaagt gccatatgca cctgggagcc agaaggggca ccttccagcc gtaccagtgc   3097

aactttagcc agaccaagct gctgttggag aacgatgcct tctccagggt gaacctgaac   3157

ggcatctttg acatggatgt ctcggtgtac aagatcctga gatacgatga gaccaagtcc   3217

agggtgcgcg cttgcgagtg cggggggcaga cacaccagga tgcagccagt ggccctggat   3277

gtgaccgagg agctgagacc agaccacctg gtgatggcct gtaccgggac cgagttcagc   3337

tccagtgggg aggacacaga ttagaggtag gtcgagtgag tagtgggcgt ggctaaggtg   3397

actataaagg cgggtgtctt acgagggtct tttgcttttt ctgcagacat catgaacggg   3457

acgggcgggg ccttcgaagg ggcgcttttt agcccttatt tgacaacccg cctgccggga   3517

tgggccggag ttcgtcagaa tgtgatggga tcgacggtgg atgggcgccc agtgcttcca   3577

gcaaattcct cgaccatgac ctacgcgacc gtggggagct cgtcgctcga cagcaccgcc   3637

gcagccgcgg cagccgcagc tgccatgaca gcgacgagac tggcctcgag ctacatgccc   3697

agcagcggca gcagcccctc tgtgcccagt tccatcatcg ccgaggagaa actgctggcc   3757

ctgctggccg agctggaagc cctgagccgc cagctggccg ccctgaccca gcaggtgtcc   3817

gacgtccgcg agcagcaaca gcagcaaaat aaatgattca ataaacacag attctgattc   3877

aaacagcaaa gcatctttat tattatttat tttttcgcgc gcggtaggcc ctggtccacc   3937

tctcccgatc attgagagtg cggtggattt tttccaggac ccggtagagg tgggattgga   3997

tgttgaggt                                                           4006
```

```
<210> SEQ ID NO 50
<211> LENGTH: 182
<212> TYPE: PRT
<213> ORGANISM: human adenovirus type 9

<400> SEQUENCE: 50

Met Asp Val Trp Thr Ile Leu Ala Asp Phe Ser Lys Thr Arg Arg Leu
1               5                   10                  15

Val Glu Asp Ser Ser Asp Gly Cys Ser Gly Phe Trp Arg His Trp Phe
            20                  25                  30

Gly Thr Pro Leu Ser Arg Leu Val Tyr Thr Val Lys Lys Asp Tyr Lys
        35                  40                  45

Glu Glu Phe Glu Asn Ile Phe Ala Asp Cys Ser Gly Leu Leu Asp Ser
    50                  55                  60

Leu Asn Leu Gly His Gln Ser Leu Phe Gln Glu Arg Val Leu His Ser
65                  70                  75                  80
```

-continued

```
Leu Asp Phe Ser Ser Pro Gly Arg Thr Thr Ala Gly Val Ala Phe Val
                 85                  90                  95

Val Phe Leu Val Asp Lys Trp Ser Gln Asp Thr Gln Leu Ser Arg Gly
            100                 105                 110

Tyr Ile Leu Asp Phe Ala Ala Met His Leu Trp Arg Ala Trp Ile Arg
        115                 120                 125

Gln Arg Gly Gln Arg Ile Leu Asn Tyr Trp Leu Leu Gln Pro Ala Ala
    130                 135                 140

Pro Gly Leu Leu Arg Leu His Arg Gln Thr Ser Met Leu Glu Glu Glu
145                 150                 155                 160

Met Arg Gln Ala Met Asp Glu Asn Pro Arg Ser Gly Leu Asp Pro Pro
                165                 170                 175

Ser Glu Glu Glu Leu Asp
            180
```